United States Patent
Lücking et al.

(10) Patent No.: US 9,499,492 B2
(45) Date of Patent: Nov. 22, 2016

(54) 4-(ORTHO)-FLUOROPHENYL-5-FLUOROPYRIMIDIN-2-YL AMINES CONTAINING A SULFOXIMINE GROUP

(71) Applicant: BAYER PHARMA AKTIENGESELLSCHAFT, Berlin (DE)

(72) Inventors: Ulrich Lücking, Berlin (DE); Dirk Kosemund, Berlin (DE); Rolf Bohlmann, Berlin (DE); Arne Scholz, Berlin (DE); Philip Lienau, Berlin (DE); Gerhard Siemeister, Berlin (DE); Ulf Bömer, Glienicke (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 14/443,180

(22) PCT Filed: Nov. 11, 2013

(86) PCT No.: PCT/EP2013/073480
§ 371 (c)(1),
(2) Date: May 15, 2015

(87) PCT Pub. No.: WO2014/076028
PCT Pub. Date: May 22, 2014

(65) Prior Publication Data
US 2015/0291537 A1    Oct. 15, 2015

(30) Foreign Application Priority Data
Nov. 15, 2012    (EP) .................................... 12192862

(51) Int. Cl.
| | | |
|---|---|---|
| *C07D 239/42* | (2006.01) | |
| *A61K 31/505* | (2006.01) | |
| *A61K 31/506* | (2006.01) | |
| *C07D 405/04* | (2006.01) | |

(52) U.S. Cl.
CPC ........... *C07D 239/42* (2013.01); *A61K 31/505* (2013.01); *A61K 31/506* (2013.01); *C07D 405/04* (2013.01)

(58) Field of Classification Search
CPC . C07D 405/04; C07D 239/42; A61K 31/506
USPC .......................................... 544/330; 514/275
See application file for complete search history.

(56) References Cited

U.S. PATENT DOCUMENTS
9,133,171 B2 *   9/2015   Lucking ............... C07D 405/04

FOREIGN PATENT DOCUMENTS
WO    WO 2013/037894    *    3/2013

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, 20th Edition, vol. 1, pp. 1004-1101 O, 1996.*
Douglas, Jr., Introduction to Viral Diseases, Cecil Textbook of Medicine, 20th Edition, vol. 2, pp. 1739-1747, 1996.*

* cited by examiner

*Primary Examiner* — Deepak Rao

(57) ABSTRACT

The present invention relates to 4-(ortho)-fluorophenyl-5-fluoropyrimidin-2-yl amine derivatives containing a sulfoximine group of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

14 Claims, No Drawings

4-(ORTHO)-FLUOROPHENYL-5-FLUOROPYRIMIDIN-2-YL AMINES CONTAINING A SULFOXIMINE GROUP

The present invention relates to 4-(ortho)-fluorophenyl-5-fluoropyrimidin-2-yl amine derivatives containing a sulfoximine group of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNApolymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 9, 1697, 2010). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol Cell 29, 588, 2008). The remaining half of P-TEFb exists in an active complex containing the bromodomain protein Brd4 (Yang et al., Mol Cell 19, 535, 2005). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol Mol Biol Rev 70, 646, 2006). Furthermore, the activity of P-TEFb is regulated by posttranslational modifications including phosphorylation/de-phosphorylation, ubiquitination, and acetylation (reviewed in Cho et al., Cell Cycle 9, 1697, 2010).

Deregulated activity of CDK9 kinase activity of the P-TEFb heterodimer is associated with a variety of human pathological settings such as hyper-proliferative diseases (e.g. cancer), virally induced infectious diseases or cardiovascular diseases:

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance Inhibition of P-TEFb kinase activity was shown to reduce transcriptional activity of RNA polymerase II leading to a decline of short-lived anti-apoptotic proteins, especially Mcl-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol Sci 29, 302, 2008).

Many viruses rely on the transcriptional machinery of the host cell for the transcription of their own genome. In case of HIV-1, RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 replction at kinase inhibitor concentrations that are not cytotoxic to the host cells (reviewed in Wang & Fischer, Trends Pharmacol Sci 29, 302, 2008). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene, 25, 1775, 2006), and the human T-lymphotropic virus type 1 (HTLV-1), where the transcriptional activator Tax recruits P-TEFb (Zhou et al., J Virol. 80, 4781, 2006).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 6, 1856, 2007).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDKs (e.g. CDK1/cyclin B, CDK2/cyclin A, CDK2/cyclinE, CDK4/cyclinD, CDK6/cyclinD) and of CDK9, is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are required.

CDK inhibitors in general as well as CDK9 inhibitors are described in a number of different publications: WO2008129070 and WO2008129071 both describe 2,4 disubstituted aminopyrimidines as CDK inhibitors in general. It is also asserted that some of these compounds may act as selective CDK9 inhibitors (WO2008129070) and as CDK5 inhibitors (WO2008129071), respectively, but no specific CDK9 $IC_{50}$ (WO2008129070) or CDK5 $IC_{50}$ (WO2008129071) data is presented. These compounds do not contain a fluoro atom in 5-position of the pyrimidine core.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

WO2005026129 discloses 4,6 disubstituted aminopyrimidines and demonstrates that these compounds show an inhibitory effect on the protein kinase activity of various protein kinases, in particular CDK2, CDK4, and CDK9.

WO2011116951 discloses substituted triazine derivatives as selective CDK9 inhibitors.

WO2012117048 discloses disubstituted triazine derivatives as selective CDK9 inhibitors.

WO2012117059 discloses disubstituted pyridine derivatives as selective CDK9 inhibitors.

WO2012143399 discloses substituted 4-aryl-N-phenyl-1, 3,5-triazin-2-amines as selective CDK9 inhibitors.

EP1218360 B1, which corresponds to US2004116388A1, U.S. Pat. No. 7,074,789B2 and WO2001025220A1, describes triazine derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

WO2011026917 discloses carboxamides derived from substituted 4-phenylpyridine-2-amines as inhibitors of CDK9.

WO2012066065 discloses phenyl-heteroaryl amines as inhibitors of CDK9. A selectivity towards CDK9 over other CDK isoforms is preferred, however disclosure of CDK-inhibition data is confined to CDK 9. No bicyclic ring systems are disclosed attached to the C4 position of the pyrimidine core. Within the group attached to C4 of the pyrimidine core, alkoxy phenyls can be regarded as encompassed, but there is no suggestion for a specific substitution pattern characterised by a fluoro atom attached to C5 of the pyrimidine ring, and an aniline at C2 of the pyrimidine, featuring a substituted sulfonyl-methylene group in meta position. Compounds shown in the examples typically feature a substituted cycloalkyl group as $R^1$ but no phenyl.

WO2012066070 discloses 3-(aminoaryl)-pyridine compounds as inhibitors of CDK9. The biaryl core mandatorily consists of two heteroaromatic rings.

WO2012101062 discloses substituted bi-heteroaryl compounds featuring a 2-aminopyridine core as inhibitors of CDK9. The biaryl core mandatorily consists of two heteroaromatic rings.

WO2012101063 discloses carboxamides derived from substituted 4-(heteroaryl)-pyridine-2-amines as inhibitors of CDK9.

WO 2012101064 discloses N-acyl pyrimidine biaryl compounds as inhibitors of CDK9.

WO 2012101065 discloses pyrimidine biaryl compounds as inhibitors of CDK9. The biaryl core mandatorily consists of two heteroaromatic rings.

WO 2012101066 discloses pyrimidine biaryl compounds as inhibitors of CDK9. Substitution $R^1$ of the amino group attached to the heteroaromatic core is confined to non-aromatic groups but does not cover substituted phenyls. Furthermore, the biaryl core mandatorily consists of two heteroaromatic rings.

WO 2013037896 discloses disubstituted 5-fluoropyrimidines as selective inhibitors of CDK9.

WO 2013037894, published after the priority date of the present application, describes disubstituted 5-fluoropyrimidine derivatives containing a sulfoximine group as selective inhibitors of CDK9. The document discloses (rac)-ethyl[(3-{[4-(2,4-difluorophenyl)-5-fluoropyrimidin-2-yl]amino}benzyl)(methyl)oxido-$\lambda^6$-sulfanylidene]carbamate as Intermediate compound 55.2 but not as an active compound inhibiting CDK9.

Wang et al. (Chemistry & Biology 17, 1111-1121, 2010) describe 2-anilino-4-(thiazol-5-yl)pyrimidine transcriptional CDK inhibitors, which show anticancer activity in animal models.

WO2004009562 discloses substituted triazine kinase inhibitors. For selected compounds CDK1 and CDK4 test data, but no CDK9 data is presented.

WO2004072063 describes heteroaryl (pyrimidine, triazine) substituted pyrroles as inhibitors of protein kinases such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to U.S. Pat. No. 7,618, 968B2, U.S. Pat. No. 7,291,616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2005037800 discloses sulfoximine substituted anilino-pyrimidines as inhibitors of VEGFR and CDK kinases, in particular VEGFR2, CDK1 and CDK2, having no aromatic ring directly bonded to the pyrimidine ring and having the sulfoximine group directly bonded to the aniline group. No CDK9 data are disclosed.

WO2008025556 describes carbamoyl sulfoximides having a pyrimidine core, which are useful as kinase inhibitors. No CDK9 data is presented. No molecules are exemplified, which possess a fluoropyrimidine core.

WO2002066481 describes pyrimidine derivatives as cyclin dependent kinase inhibitors. CDK9 is not mentioned and no CDK9 data is presented.

WO2008109943 concerns phenyl aminopyri(mi)dine compounds and their use as kinase inhibitors, in particular as JAK2 kinase inhibitors. The specific examples mainly focus on compounds having a pyrimidine core.

WO2009032861 describes substituted pyrimidinyl amines as JNK kinase inhibitors. The specific examples mainly focus on compounds having a pyrimidine core.

WO2011046970 concerns amino-pyrimidine compounds as inhibitors of TBKL and/or IKK epsilon. The specific examples mainly focus on compounds having a pyrimidine core.

WO2012142329 concerns amino-pyrimidine compounds as inhibitors of TBKL and/or IKK epsilon.

WO2012139499 discloses urea substituted anilino-pyrimidines as inhibitors of various protein kinases.

Despite the fact that various inhibitors of CDKs are known, there remains a need for selective CDK9 inhibitors to be used for the treatment of diseases such as hyperproliferative diseases, viral diseases, and/or diseases of the heart, which offer one or more advantages over the compounds known from prior art, such as:
  improved activity and/or efficacy
  beneficial kinase selectivity profile according to the respective therapeutic need
  improved side effect profile, such as fewer undesired side effects, lower intensity of side effects, or reduced (cyto)toxicity
  improved physicochemical properties, such as solubility in water and body fluids
  improved pharmacokinetic properties, allowing e.g. for dose reduction or an easier dosing scheme
  easier drug substance manufacturing e.g. by shorter synthetic routes or easier purification.

A particular object of the invention is to provide CDK9 kinase inhibitors which show an increased potency to inhibit CDK9 activity (demonstrated by a lower $IC_{50}$ value for CDK9/Cyclin T1) compared to the compounds known from prior art.

Another object of the invention is to provide CDK9 kinase inhibitors which, compared to the compounds known from prior art, show an increased selectivity for CDK9/Cyclin T1 as compared to CDK2/Cyclin E.

Another object of the invention is to provide CDK9 kinase inhibitors which show an increased potency to inhibit CDK9 activity at high ATP concentrations compared to the compounds known from prior art.

Another object of the invention is to provide CDK9 kinase inhibitors, which show an improved anti-proliferative activity in tumor cell lines such as HeLa compared to the compounds known from prior art.

Another object of the invention is to provide CDK9 kinase inhibitors, which show an improved metabolic stability in relevant in vitro systems such as rat hepatocyte incubations, and an extended terminal half-life upon administration in vivo, e.g. intravenous administration in rats.

Further, it is also an object of the present invention to provide CDK9 kinase inhibitors, which, compared to the compounds known from prior art, are highly selective for CDK9/Cyclin T1 as compared to CDK2/Cyclin E, and/or which show an increased potency to inhibit CDK9 activity and/or which show an improved anti-proliferative activity in tumor cell lines such as HeLa and/or which show an increased potency to inhibit CDK9 activity at high ATP concentrations, and/or feature an improved metabolic stability in relevant in vitro systems such as rat hepatocyte incubations, and an extended terminal half-life upon administration in vivo, e.g. intravenous administration in rats, compared to the compounds known from prior art.

The selectivity CDK9/CDK2 is preferred to be greater than 15, more preferred greater than 25, even more preferred greater than 40, particularly preferred greater than 60 and most preferred greater than 100.

The present invention relates to compounds of general formula (I)

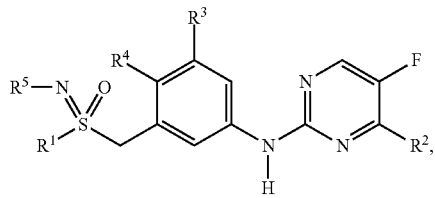

wherein
$R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
  wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —$OP(O)(OH)_2$, —$C(O)OH$, —$C(O)NH_2$;
$R^2$ represents the group

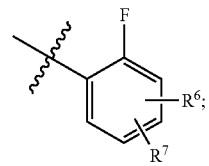

$R^3$, $R^4$ represent, independently from each other, a group selected from a hydrogen atom, halogen atom, cyano, —$SF_5$, $C_1$-$C_3$-alkyl-, $C_1$-$C_3$-alkoxy-, hydroxy, halo-$C_1$-$C_3$-alkyl-, $C_1$-$C_3$-fluoroalkoxy-;
$R^5$ represents a group selected from a hydrogen atom, cyano, —$C(O)R^8$, —$C(O)OR^8$, —$S(O)_2R^8$, —$C(O)NR^9R^{10}$, —$P(O)(OR^{11})_2$, —$CH_2OP(OR^{11})_2$, $C_1$-$C_6$-alkyl-, $C_3$-$C_7$-cycloalkyl-, heterocyclyl-, phenyl, heteroaryl,
  wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;
$R^8$ represents a group selected from $C_1$-$C_6$-alkyl-, $C_3$-$C_7$-cycloalkyl-, heterocyclyl-, phenyl, benzyl or heteroaryl,
  wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
$R^9$, $R^{10}$ represent, independently from each other, a group selected from hydrogen, $C_1$-$C_6$-alkyl-, $C_3$-$C_7$-cycloalkyl-, heterocyclyl-, phenyl, benzyl or heteroaryl,
  wherein said $C_1$-$C_6$-alkyl, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^9$ and $R^{10}$, together with the nitrogen atom they are attached to, form a cyclic amine;

$R^{11}$ represents a group selected from hydrogen, $C_1$-$C_4$-alkyl or benzyl, and the enantiomers, diastereomers, salts, solvates or salts of solvates thereof, with the proviso that the compound is not (rac)-ethyl[(3-{[4-(2,4-difluorophenyl)-5-fluoropyrimidin-2-yl]amino}benzyl)(methyl)oxido-$\lambda^6$-sulfanylidene]carbamate.

The present invention relates to compounds of general formula (I)

wherein $R^1$ represents a group selected from $C_1$-$C_6$-alkyl-, $C_3$-$C_7$-cycloalkyl-, heterocyclyl-, phenyl, heteroraryl, phenyl-$C_1$-$C_3$-alkyl- or heteroaryl-$C_1$-$C_3$-alkyl-, wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$;

$R^2$ represents the group

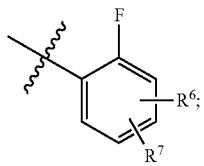

$R^3$, $R^4$ represent, independently from each other, a group selected from a hydrogen atom, halogen atom, cyano, —$SF_5$, $C_1$-$C_3$-alkyl-, $C_1$-$C_3$-alkoxy-, hydroxy, halo-$C_1$-$C_3$-alkyl-, $C_1$-$C_3$-fluoroalkoxy-;

$R^5$ represents a group selected from a hydrogen atom, cyano, —C(O)$R^8$, —C(O)O$R^8$, —S(O)$_2R^8$, —C(O)N$R^9R^{10}$, —P(O)(OR)$_2$, —CH$_2$OP(OR)$_2$, $C_1$-$C_6$-alkyl-, $C_3$-$C_7$-cycloalkyl-, heterocyclyl-, phenyl, heteroaryl, wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^8$ represents a group selected from $C_1$-$C_6$-alkyl-, $C_3$-$C_7$-cycloalkyl-, heterocyclyl-, phenyl, benzyl or heteroaryl, wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^9$, $R^{10}$ represent, independently from each other, a group selected from hydrogen, $C_1$-$C_6$-alkyl-, $C_3$-$C_7$-cycloalkyl-, heterocyclyl-, phenyl, benzyl or heteroaryl, wherein said $C_1$-$C_6$-alkyl, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^9$ and $R^{10}$, together with the nitrogen atom they are attached to, form a cyclic amine;

and the enantiomers, diastereomers, salts, solvates or salts of solvates thereof.

Compounds according to the invention are the compounds of the formula (I) and the salts, solvates and solvates of the salts thereof, the compounds of the hereinafter recited formula which are encompassed by formula (I) and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol. Additionally, the compounds according to the invention may form salts with a quarternary ammonium ion obtainable e.g. by quarternisation of a basic nitrogen containing group with agents like lower alkylhalides such as methyl-, ethyl-, propyl-, and butylchlorides, -bromides and -iodides; dialkylsulfates like dimethyl-, diethyl-, dibutyl- and diamylsulfates, long chain halides such as decyl-, lauryl-, myristyl- and stearylchlorides, -bromides and -iodides, aralkylhalides like benzyl- and phenethylbromides and others. Examples of suitable quarternary ammonium ions are tetramethylammonium, tetraethylammonium, tetra(n-propyl)ammonium, tetra(n-butyl)ammonium, or N-benzyl-N,N,N-trimethylammonium.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

Furthermore, the present invention includes all possible crystalline forms, or polymorphs, of the compounds of the present invention, either as single polymorphs, or as a mixture of more than one polymorphs, in any ratio.

Accordingly, the present invention includes all possible salts, polymorphs, metabolites, hydrates, solvates, prodrugs (e.g.: esters) thereof, and diastereoisomeric forms of the compounds of the present invention as single salt, polymorph, metabolite, hydrate, solvate, prodrug (e.g.: esters) thereof, or diastereoisomeric form, or as mixture of more than one salt, polymorph, metabolite, hydrate, solvate, prodrug (e.g.: esters) thereof, or diastereoisomeric form in any ratio.

For the purposes of the present invention, the substituents have the following meaning, unless otherwise specified:

The term "halogen", "halogen atom" or "halo" represents fluorine, chlorine, bromine and iodine, particularly chlorine or fluorine, preferably fluorine.

The term "alkyl" represents a linear or branched alkyl radical having the number of carbon atoms specifically indicated, e.g. $C_1$-$C_{10}$ one, two, three, four, five, six, seven, eight, nine or ten carbon atoms, e.g. methyl, ethyl, n-propyl, isopropyl, n-butyl, isobutyl, sec-butyl, tert-butyl, pentyl, isopentyl, hexyl, heptyl, octyl, nonyl-, decyl-, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. If the number of carbon atoms is not specifically indicated the term "alkyl" represents a linear or branched alkyl radical having, as a rule, 1 to 9, particularly 1 to 6, preferably 1 to 4 carbon atoms. Particularly, the alkyl group has 1, 2, 3, 4, 5 or 6 carbon atoms ("$C_1$-$C_6$-alkyl"), e.g. methyl, ethyl, n-propyl-, isopropyl, n-butyl, tert-butyl, pentyl, isopentyl, hexyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. Preferably, the alkyl group has 1, 2 or 3 carbon atoms ("$C_1$-$C_3$-alkyl"), methyl, ethyl, n-propyl or isopropyl.

The term "$C_3$-$C_7$-cycloalkyl" is to be understood as preferably meaning a saturated, monovalent, monocyclic hydrocarbon ring which contains 3, 4, 5, 6 or 7 carbon atoms. Said $C_3$-$C_7$-cycloalkyl group is for example, a monocyclic hydrocarbon ring, e.g. a cyclopropyl, cyclobutyl, cyclopentyl, cyclohexyl or cycloheptyl group. Said cycloalkyl ring is non-aromatic but can optionally contain one or more double bonds e.g. cycloalkenyl, such as a cyclopropenyl, cyclobutenyl, cyclopentenyl, cyclohexenyl or cycloheptenyl group, wherein the bond between said ring with the rest of the molecule may be to any carbon atom of said ring, be it saturated or unsaturated. Particularly, said cycloalkyl group is a $C_4$-$C_6$-cycloalkyl, a $C_5$-$C_6$-cycloalkyl or a cyclohexyl group.

The term "$C_3$-$C_5$-cycloalkyl" is to be understood as preferably meaning a saturated, monovalent, monocyclic hydrocarbon ring which contains 3, 4 or 5 carbon atoms. In particular said $C_3$-$C_5$-cycloalkyl group is a monocyclic hydrocarbon ring such as a cyclopropyl, cyclobutyl or cyclopentyl group. Preferably said "$C_3$-$C_5$-cycloalkyl" group is a cyclopropyl group.

The term "$C_3$-$C_6$-cycloalkyl" is to be understood as preferably meaning a saturated, monovalent, monocyclic hydrocarbon ring which contains 3, 4, 5 or 6 carbon atoms. In particular said $C_3$-$C_6$-cycloalkyl group is a monocyclic hydrocarbon ring such as a cyclopropyl, cyclobutyl, cyclopentyl or cyclohexyl group.

The term "heterocyclyl" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl" is to be understood as meaning a "4- to 10-membered heterocyclic ring".

The term "a 4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen. A $C_3$-$C_9$-heterocyclyl is to be understood as meaning a heterocyclyl which contains at least 3, 4, 5, 6, 7, 8 or 9 carbon atoms and additionally at least one heteroatom as ring atoms. Accordingly in case of one heteroatom the ring is 4- to 10-membered, in case of two heteroatoms the ring is 5- to 11-membered and in case of three heteroatoms the ring is 6- to 12-membered.

Said heterocyclic ring is for example, a monocyclic heterocyclic ring such as an oxetanyl, azetidinyl, tetrahydrofuranyl, pyrrolidinyl, 1,3-dioxolanyl, imidazolidinyl, pyrazolidinyl, oxazolidinyl, isoxazolidinyl, 1,4-dioxanyl, pyrrolinyl, tetrahydropyranyl, piperidinyl, morpholinyl, 1,3-dithianyl, thiomorpholinyl, piperazinyl, or chinuclidinyl group. Optionally, said heterocyclic ring can contain one or more double bonds, e.g. 4H-pyranyl, 2H-pyranyl, 2,5-dihydro-1H-pyrrolyl, 1,3-dioxolyl, 4H-1,3,4-thiadiazinyl, 2,5-dihydrofuranyl, 2,3-dihydrofuranyl, 2,5-dihydrothienyl, 2,3-dihydrothienyl, 4,5-dihydrooxazolyl, 4,5-dihydroisoxazolyl, or 4H-1,4-thiazinyl group, or, it may be benzo fused.

Particularly a $C_3$-$C_7$-heterocyclyl is to be understood as meaning a heterocyclyl which contains at least 3, 4, 5, 6, or 7 carbon atoms and additionally at least one heteroatom as ring atoms. Accordingly in case of one heteroatom the ring is 4- to 8-membered, in case of two heteroatoms the ring is 5- to 9-membered and in case of three heteroatoms the ring is 6- to 10-membered.

Particularly a $C_3$-$C_6$-heterocyclyl is to be understood as meaning a heterocyclyl which contains at least 3, 4, 5 or 6 carbon atoms and additionally at least one heteroatom as ring atoms. Accordingly in case of one heteroatom the ring is 4- to 7-membered, in case of two heteroatoms the ring is 5- to 8-membered and in case of three heteroatoms the ring is 6- to 9-membered.

Particularly, the term "heterocyclyl" is to be understood as being a heterocyclic ring which contains 3, 4 or 5 carbon atoms, and 1, 2 or 3 of the above-mentioned heteroatom-containing groups (a "4- to 8-membered heterocyclic ring"), more particularly said ring can contain 4 or 5 carbon atoms, and 1, 2 or 3 of the above-mentioned heteroatom-containing groups (a "5- to 8-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the above-mentioned heteroatom-containing groups, preferably 4 carbon atoms and 2 of the above-mentioned heteroatom-containing groups.

The term "$C_1$-$C_6$-alkoxy-" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentyloxy, iso-pentyloxy, n-hexyloxy group, or an isomer thereof. Particularly, the "$C_1$-$C_6$-alkoxy-" group is a "$C_1$-$C_4$-alkoxy-", a "$C_1$-$C_3$-alkoxy-", a methoxy, ethoxy, or propoxy group, preferably a methoxy, ethoxy or propoxy group. Further preferred is a "$C_1$-$C_2$-alkoxy-" group, particularly a methoxy or ethoxy group.

The term "$C_1$-$C_3$-fluoroalkoxy-" is to be understood as preferably meaning a linear or branched, saturated, monovalent, $C_1$-$C_3$-alkoxy-group, as defined supra, in which one or more of the hydrogen atoms is replaced, identically or differently, by one or more fluoro atoms. Said $C_1$-$C_3$-fluoroalkoxy-group is, for example a 1,1-difluoromethoxy-, a 1,1,1-trifluoromethoxy-, a 2-fluoroethoxy-, a 3-fluoropropoxy-, a 2,2,2-trifluoroethoxy-, a 3,3,3-trifluoropropoxy- particularly a "$C_1$-$C_2$-fluoroalkoxy-" group.

The term "alkylamino-" is to be understood as preferably meaning an alkylamino group with one linear or branched alkyl group as defined supra. ($C_1$-$C_3$)-alkylamino- for example means a monoalkylamino group with 1, 2 oder 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, iso-propylamino-, tert.-butylamino-, n-pentylamino- or n-hexylamino-.

The term "dialkylamino-" is to be understood as preferably meaning an alkylamino group having two linear or branched alkyl groups as defined supra, which are independent from each other. ($C_1$-$C_3$)-dialkylamino- for example represents a dialkylamino group with two alkyl groups each of them having 1 to 3 carbon atoms per alkyl group. The term "dialkylamino-" comprises for example: N,N-Dimethylamino-, N,N-Diethylamino-, N-Ethyl-N-methylamino-, N-Methyl-N-n-propylamino-, N-Isopropyl-N-n-propylamino-, N-t-Butyl-N-methylamino-, N-Ethyl-N-n-pentylamino-und N-n-Hexyl-N-methylamino-.

The term "cyclic amine" is to be understood as preferably meaning a cyclic amine group. Preferably, a cyclic amine means a saturated, monocyclic group with 4 to 10, preferably 4 to 7 ring atoms of which at least one ring atom is a nitrogen atom. Suitable cyclic amines are especially azetidine, pyrrolidine, piperidine, piperazine, 1-methylpiperazine, morpholine, thiomorpholine, which could be optionally substituted by one or two methyl groups.

The term "halo-$C_1$-$C_3$-alkyl-" is to be understood as preferably meaning a linear or branched, saturated, monovalent hydrocarbon group in which the term "$C_1$-$C_3$-alkyl" is defined supra, and in which one or more hydrogen atoms is replaced by a halogen atom, identically or differently, i.e. one halogen atom being independent from another. Particularly, said halogen atom is fluorine. Preferred halo-$C_1$-$C_3$-alkyl- group is a fluoro-$C_1$-$C_3$-alkyl- group or, synonymously used, a $C_1$-$C_3$-fluoroalkyl group, such as for example —$CF_3$, —$CHF_2$, —$CH_2F$, —$CF_2CF_3$, or —$CH_2CF_3$, preferably it is —$CF_3$.

The term "phenyl-$C_1$-$C_3$-alkyl-" is to be understood as preferably meaning a phenyl group, in which one of the hydrogen atoms is replaced by a $C_1$-$C_3$-alkyl group, as defined supra, that links the phenyl-$C_1$-$C_3$-alkyl-group to the molecule. Particularly, the "phenyl-$C_1$-$C_3$-alkyl-" is a phenyl-$C_1$-$C_2$-alkyl-, preferably it is a benzyl- group.

The term "heteroaryl" is to be understood as preferably meaning a monovalent, aromatic ring system having 5, 6, 7, 8, 9, 10, 11, 12, 13 or 14 ring atoms (a "5- to 14-membered heteroaryl" group), particularly 5 (a "5-membered heteroaryl") or 6 (a "6-membered heteroaryl") or 9 (a "9-membered heteroaryl") or 10 ring atoms (a "10-membered heteroaryl"), and which contains at least one heteroatom which may be identical or different, said heteroatom being such as oxygen, nitrogen or sulfur, and can be monocyclic, bicyclic, or tricyclic, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc. Preferably, heteroaryl is selected from monocyclic heteroaryl, 5-membered heteroaryl or 6-membered heteroaryl.

The term "5-membered heteroaryl" is understood as preferably meaning a monovalent, aromatic ring system having 5 ring atoms and which contains at least one heteroatom which may be identical or different, said heteroatom being such as oxygen, nitrogen or sulfur. Particularly, "5-membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl.

The term "6-membered heteroaryl" is understood as preferably meaning a monovalent, aromatic ring system having 6 ring atoms and which contains at least one heteroatom which may be identical or different, said heteroatom being such as oxygen, nitrogen or sulfur. Particularly, "6-membered heteroaryl" is selected from pyridyl, pyridazinyl, pyrimidinyl, pyrazinyl, triazinyl.

The term "heteroaryl-$C_1$-$C_3$-alkyl-" is to be understood as preferably meaning a heteroaryl, a 5-membered heteroaryl or a 6-membered heteroaryl group, each as defined supra, in which one of the hydrogen atoms is replaced by a $C_1$-$C_3$-alkyl group, as defined supra, that links the heteroaryl-$C_1$-$C_3$-alkyl- group to the molecule. Particularly, the "heteroaryl-$C_1$-$C_3$-alkyl-" is a heteroaryl-$C_1$-$C_2$-alkyl-, a pyridinyl-$C_1$-$C_3$-alkyl-, a pyridinylmethyl-, a pyridinylethyl-, a pyridinylpropyl-, -a pyrimidinyl-$C_1$-$C_3$-alkyl-, a pyrimidinylmethyl-, a pyrimidinylethyl-, a pyrimidinylpropyl-, preferably a pyridinylmethyl- or a pyridinylethyl- or a pyrimidinylethyl- or a pyrimidinylpropyl- group.

The term "$C_1$-$C_{10}$", as used throughout this text, e.g. in the context of the definition of "$C_1$-$C_{10}$-alkyl" is to be understood as meaning an alkyl group having a finite number of carbon atoms of 1 to 10, i.e. 1, 2, 3, 4, 5, 6, 7, 8, 9 or 10 carbon atoms. It is to be understood further that said term "$C_1$-$C_{10}$" is to be interpreted as any sub-range comprised therein, e.g. $C_1$-$C_{10}$, $C_1$-$C_9$, $C_1$-$C_8$, $C_1$-$C_7$, $C_1$-$C_6$ $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, $C_9$-$C_{10}$.

Similarly, as used herein, the term "$C_1$-$C_6$", as used throughout this text, e.g. in the context of the definition of "$C_1$-$C_6$-alkyl", "$C_1$-$C_6$-alkoxy" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$ $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_3$", as used throughout this text, e.g. in the context of the definition of "$C_1$-$C_3$-alkyl", "$C_1$-$C_3$-alkoxy" or "$C_1$-$C_3$-fluoroalkoxy" is to be understood as meaning an alkyl group having a finite number of carbon atoms of 1 to 3, i.e. 1, 2 or 3 carbon atoms. It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_3$-$C_5$, $C_3$-$C_4$, $C_4$-$C_6$, $C_4$-$C_5$, $C_5$-$C_6$. Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$, $C_5$-$C_6$, $C_6$-$C_7$.

A symbol ⁄ at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene) sulfonyloxy, (4-nitro-benzene) sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

Where the plural form of the word compounds, salts, hydrates, solvates and the like, is used herein, this is taken to mean also a single compound, salt, isomer, hydrate, solvate or the like.

In another embodiment, the present invention concerns compounds of general formula (I),

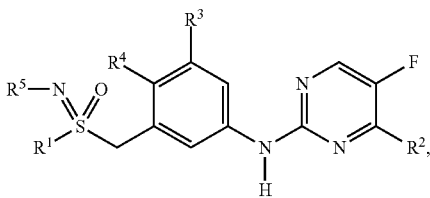

(I)

wherein
$R^1$ represents a group selected from $C_1$-$C_6$-alkyl-, $C_3$-$C_7$-cycloalkyl, phenyl, or phenyl-$C_1$-$C_3$-alkyl-, wherein said group is optionally substituted with one or two or three substituents, identically or differently, selected from the group of hydroxy, cyano, halogen, halo-$C_1$-$C_3$-alkyl-, $C_1$-$C_3$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$;

$R^2$ represents the group

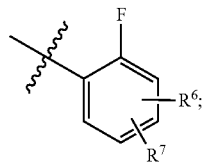

$R^3$, $R^4$ represent, independently from each other, a group selected from a hydrogen atom, halogen atom, —SF$_5$, $C_1$-$C_3$-alkyl-, $C_1$-$C_3$-alkoxy-, halo-$C_1$-$C_3$-alkyl-, $C_1$-$C_3$-fluoroalkoxy-;

$R^5$ represents a group selected from a hydrogen atom, cyano, —C(O)R$^8$, —S(O)$_2$R$^8$, —C(O)NR$^9$R$^{10}$, —P(O)(OR$^{11}$)$_2$, —CH$_2$OP(OR$^{11}$)$_2$, $C_1$-$C_3$-alkyl-, $C_3$-$C_5$-cycloalkyl-, phenyl,
wherein said $C_1$-$C_3$-alkyl, $C_3$-$C_5$-cycloalkyl- or phenyl group is optionally substituted with one or two substituents, identically or differently, selected from hydroxy, —NH$_2$, alkylamino-, dialkylamino-, cyclic amines;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^8$ represents a group selected from $C_1$-$C_3$-alkyl-, $C_3$-$C_5$-cycloalkyl-, heterocyclyl-, phenyl or benzyl,
wherein said group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^9$, $R^{10}$ represent, independently from each other, a group selected from hydrogen, $C_1$-$C_3$-alkyl-, $C_3$-$C_5$-cycloalkyl-, heterocyclyl-, phenyl or benzyl,
wherein said $C_1$-$C_3$-alkyl-, $C_3$-$C_5$-cycloalkyl-, heterocyclyl-, phenyl or benzyl group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-; or $R^9$ and $R^{10}$, together with the nitrogen atom they are attached to, form a cyclic amine;

$R^{11}$ represents a group selected from hydrogen or $C_1$-$C_4$-alkyl,
and the enantiomers, diastereomers, salts, solvates or salts of solvates thereof.

In another embodiment the present invention concerns compounds of general formula (I),
wherein
$R^1$ represents a group selected from $C_1$-$C_6$-alkyl-, $C_3$-$C_7$-cycloalkyl, phenyl, or phenyl-$C_1$-$C_3$-alkyl-,
wherein said group is optionally substituted with one or two or three substituents, identically or differently, selected from the group of hydroxy, cyano, halogen, halo-$C_1$-$C_3$-alkyl-, $C_1$-$C_3$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$;

$R^2$ represents the group

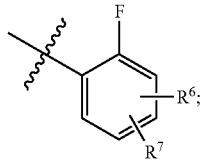

$R^3$, $R^4$ represent, independently from each other, a group selected from a hydrogen atom, halogen atom, $C_1$-$C_3$-alkyl-, $C_1$-$C_3$-alkoxy-, halo-$C_1$-$C_3$-alkyl-, $C_1$-$C_3$-fluoroalkoxy-;

$R^5$ represents a group selected from a hydrogen atom, cyano, —C(O)R$^8$, —C(O)OR$^8$, —S(O)$_2$R$^8$, —C(O)NR$^9$R$^{10}$, —P(O)(OR)$_2$, —CH$_2$OP(OR)$_2$, $C_1$-$C_3$-alkyl-, $C_3$-$C_5$-cycloalkyl-, phenyl,
wherein said $C_1$-$C_3$-alkyl, $C_3$-$C_5$-cycloalkyl- or phenyl group is optionally substituted with one or two substituents, identically or differently, selected from hydroxy, —NH$_2$, alkylamino-, dialkylamino-, cyclic amines;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^8$ represents a group selected from $C_1$-$C_3$-alkyl-, $C_3$-$C_5$-cycloalkyl-, heterocyclyl-, phenyl or benzyl,
wherein said group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^9$, $R^{10}$ represent, independently from each other, a group selected from hydrogen, $C_1$-$C_3$-alkyl-, $C_3$-$C_5$-cycloalkyl-, heterocyclyl-, phenyl or benzyl,
wherein said $C_1$-$C_3$-alkyl-, $C_3$-$C_5$-cycloalkyl-, heterocyclyl-, phenyl or benzyl group is optionally substituted with one, two or three substituents, identically or differently, selected from halogen, hydroxy, $C_1$-$C_3$-alkyl-, $C_1$-$C_3$-alkoxy-, —NH$_2$, alkylamino-, acetylamino-, N-methyl-N-acetylamino-, cyclic amines, halo-$C_1$-$C_3$-alkyl-, $C_1$-$C_3$-fluoroalkoxy-; or $R^9$ and $R^{10}$, together with the nitrogen atom they are attached to, form a cyclic amine;

and the enantiomers, diastereomers, salts, solvates or salts of solvates thereof.

In a preferred embodiment the present invention concerns compounds of general formula (I), wherein $R^1$ represents a group selected from $C_1$-$C_6$-alkyl-,
wherein said group is optionally substituted with one substituent selected from the group of $C_1$-$C_3$-alkoxy, —$NH_2$, alkylamino, dialkylamino, cyclic amines, hydroxy, —OP(O)(OH)$_2$;

$R^2$ represents the group

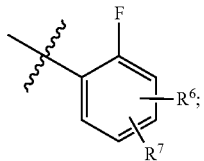

$R^3$ represents a group selected from a hydrogen atom, halogen atom, —$SF_5$, $C_1$-$C_3$-alkyl, $C_1$-$C_3$-alkoxy, or halo-$C_1$-$C_3$-alkyl-;

$R^4$ represents a hydrogen atom or a fluoro atom;

$R^5$ represents a group selected from a hydrogen atom, cyano, —C(O)NR$^9$R$^{10}$, —P(O)(OR$^{11}$)$_2$, —CH$_2$OP(OR$^{11}$)$_2$ or $C_1$-$C_3$-alkyl,
wherein said $C_1$-$C_3$-alkyl group is optionally substituted with one substituent, selected from —$NH_2$, alkylamino-, dialkylamino-, or cyclic amines;

$R^6$, $R^7$ represent, independently from each other, a group selected from a hydrogen atom, fluoro atom, $C_1$-$C_3$-alkyl-;

$R^9$, $R^{10}$ represent, independently from each other, a group selected from hydrogen, $C_1$-$C_3$-alkyl-, $C_3$-$C_5$-cycloalkyl-, or benzyl,
wherein said $C_1$-$C_3$-alkyl-, $C_3$-$C_5$-cycloalkyl- or benzyl group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-, or $R^9$ and $R^{10}$, together with the nitrogen atom they are attached to, form a cyclic amine;

$R^{11}$ represents a group selected from hydrogen or $C_1$-$C_2$-alkyl, and the enantiomers, diastereomers, salts, solvates or salts of solvates thereof.

In a preferred embodiment the present invention concerns compounds of general formula (I), wherein $R^1$ represents a group selected from $C_1$-$C_6$-alkyl-,
wherein said group is optionally substituted with one substituent selected from the group of $C_1$-$C_3$-alkoxy, —$NH_2$, alkylamino, dialkylamino, cyclic amines, hydroxy, —OP(O)(OH)$_2$;

$R^2$ represents the group

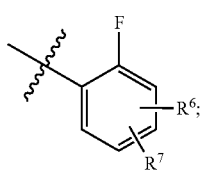

$R^3$ represents a group selected from a hydrogen atom, halogen atom, $C_1$-$C_3$-alkyl, $C_1$-$C_3$-alkoxy, or halo-$C_1$-$C_3$-alkyl-;

$R^4$ represents a hydrogen atom or a fluoro atom;

$R^5$ represents a group selected from a hydrogen atom, cyano, —C(O)OR$^8$, —C(O)NR$^9$R$^{10}$, —P(O)(OR)$_2$, —CH$_2$OP(OR)$_2$ or $C_1$-$C_3$-alkyl,
wherein said $C_1$-$C_3$-alkyl group is optionally substituted with one substituent, selected from —$NH_2$, alkylamino-, dialkylamino-, or cyclic amines;

$R^6$, $R^7$ represent, independently from each other, a group selected from a hydrogen atom, fluoro atom, $C_1$-$C_3$-alkyl-;

$R^8$ represents a group selected from $C_1$-$C_3$-alkyl-, $C_3$-$C_5$-cycloalkyl-, or benzyl,
wherein said group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-;

$R^9$, $R^{10}$ represent, independently from each other, a group selected from hydrogen, $C_1$-$C_3$-alkyl-, $C_3$-$C_5$-cycloalkyl-, or benzyl,
wherein said group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-, or $R^9$ and $R^{10}$, together with the nitrogen atom they are attached to, form a cyclic amine;

and the enantiomers, diastereomers, salts, solvates or salts of solvates thereof.

In another preferred embodiment the present invention concerns compounds of general formula (I),
wherein $R^1$ represents a $C_1$-$C_3$-alkyl group;
wherein said group is optionally substituted with one substituent selected from the group of $C_1$-$C_3$-alkoxy, —$NH_2$, alkylamino-, dialkylamino-, or cyclic amines;

$R^2$ represents the group

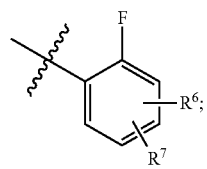

$R^3$ represents a group selected from a halogen atom or a —$SF_5$, $C_1$-$C_3$-alkyl- or fluoro-$C_1$-$C_3$-alkyl group;

$R^4$ represents a hydrogen atom;

$R^5$ represents a group selected from a hydrogen atom, cyano, —C(O)NR$^9$R$^{10}$;

$R^6$, $R^7$ represent, independently from each other, a group selected from a hydrogen atom or a fluoro atom;

$R^9$, $R^{10}$ represent, independently from each other, a group selected from hydrogen or $C_1$-$C_2$-alkyl-;

and the enantiomers, diastereomers, salts, solvates or salts of solvates thereof.

In another preferred embodiment the present invention concerns compounds of general formula (I),
wherein $R^1$ represents a $C_1$-$C_3$-alkyl group;
wherein said group is optionally one substituent selected from the group of $C_1$-$C_3$-alkoxy, —$NH_2$, alkylamino-, dialkylamino-, or cyclic amines;

$R^2$ represents the group

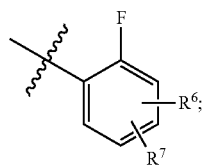

$R^3$ represents a group selected from a halogen atom or a $C_1$-$C_3$-alkyl- or $C_1$-$C_3$-fluoroalkyl group;
$R^4$ represents a hydrogen atom;
$R^5$ represents a group selected from a hydrogen atom, cyano, —C(O)NR$^9$R$^{10}$;
$R^6$, $R^7$ represent, independently from each other, a group selected from a hydrogen atom or a fluoro atom;
$R^9$, $R^{10}$ represent, independently from each other, a group selected from hydrogen or $C_1$-$C_2$-alkyl-;
and the enantiomers, diastereomers, salts, solvates or salts of solvates thereof.

In another preferred embodiment the present invention concerns compounds of general formula (I), wherein
$R^1$ represents a methyl, 2-aminoethyl or 2-methoxyethyl group;
$R^2$ represents a 2,4-difluorophenyl group;
$R^3$ represents a group selected from hydrogen, fluoro, chloro, bromo, —SF$_5$, methyl, methoxy or trifluoromethyl;
$R^4$ represents a hydrogen atom;
$R^5$ represents a group selected from a hydrogen atom, cyano, —C(O)NH$_2$;
and the enantiomers, diastereomers, salts, solvates or salts of solvates thereof.

In another preferred embodiment the present invention concerns compounds of general formula (I), wherein
$R^1$ represents a methyl or 2-methoxyethyl group;
$R^2$ represents a 2,4-difluorophenyl group;
$R^3$ represents a group selected from hydrogen, fluoro, chloro, bromo, methyl, methoxy or trifluoromethyl;
$R^4$ represents a hydrogen atom;
$R^5$ represents a group selected from a hydrogen atom, cyano, —C(O)OC$_2$H$_5$, —C(O)NH$_2$;
and the enantiomers, diastereomers, salts, solvates or salts of solvates thereof.

In a particularly preferred embodiment the present invention concerns compounds of general formula (I), wherein
$R^1$ represents a methyl, 2-aminoethyl or 2-methoxyethyl group;
$R^2$ represents a 2,4-difluorophenyl group;
$R^3$ represents a group selected from fluoro, chloro, bromo, —SF$_5$, methyl or trifluoromethyl;
$R^4$ represents a hydrogen atom;
$R^5$ represents a group selected from a hydrogen atom, cyano, —C(O)NH$_2$;
and the enantiomers, diastereomers, salts, solvates or salts of solvates thereof.

In a particularly preferred embodiment the present invention concerns compounds of general formula (I), wherein
$R^1$ represents a methyl or 2-methoxyethyl group;
$R^2$ represents a 2,4-difluorophenyl group;
$R^3$ represents a group selected from fluoro, chloro, bromo, methyl or trifluoromethyl;
$R^4$ represents a hydrogen atom;
$R^5$ represents a group selected from a hydrogen atom, cyano, —C(O)NH$_2$;
and the enantiomers, diastereomers, salts, solvates or salts of solvates thereof.

In another particularly preferred embodiment the present invention concerns compounds of general formula (I), wherein
$R^1$ represents a methyl group;
$R^2$ represents a 2,4-difluorophenyl group;
$R^3$ represents a —SF$_5$ or trifluoromethyl group;
$R^4$ represents a hydrogen atom;
$R^5$ represents a group selected from a hydrogen atom, cyano, —C(O)NH$_2$;
and the enantiomers, diastereomers, salts, solvates or salts of solvates thereof.

In another particularly preferred embodiment the present invention concerns compounds of general formula (I), wherein
$R^1$ represents a methyl group;
$R^2$ represents a 2,4-difluorophenyl group;
$R^3$ represents a trifluoromethyl group;
$R^4$ represents a hydrogen atom;
$R^5$ represents a group selected from a hydrogen atom, cyano, —C(O)NH$_2$;
and the enantiomers, diastereomers, salts, solvates or salts of solvates thereof.

In another embodiment the present invention concerns compounds of general formula (5), which constitutes a subgroup of the compounds of general formula (I)

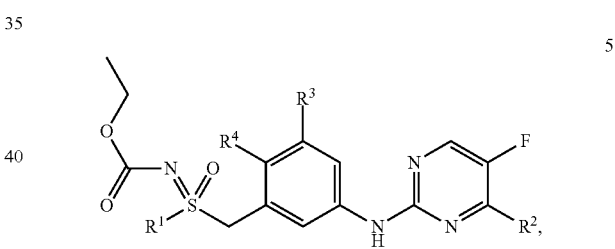

and in which $R^1$, $R^2$, $R^3$ and $R^4$ are as defined for the compounds of general formula (I) of the present invention according to general formula (I).

The compounds of general formula (5) can be used also as intermediates for the preparation of compounds of general formula (I) with a $R^5$ group different from —C(O)OC$_2$H$_5$.

In another embodiment the present invention concerns compounds of general formula (6), which constitutes a subgroup of the compounds of general formula (I)

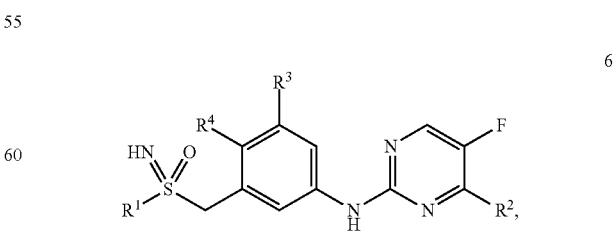

and in which $R^1$, $R^2$, $R^3$ and $R^4$ are as defined for the compounds of general formula (I) of the present invention according to general formula (I).

The compounds of general formula (6) can be used also as intermediates for the preparation of compounds of general formula (I) with a $R^5$ group different from hydrogen.

In another embodiment the present invention concerns compounds of general formula (16), which constitutes a subgroup of the compounds of general formula (I)

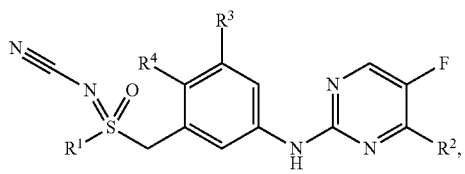

and in which $R^1$, $R^2$, $R^3$ and $R^4$ are as defined for the compounds of the present invention according to general formula (I).

The compounds of general formula (16) can be used also as intermediates for the preparation of compounds of general formula (I) with a $R^5$ group different from cyano.

In another embodiment the invention relates to compounds of formula (I), in which $R^1$ represents a $C_1$-$C_6$-alkyl-, a $C_3$-$C_7$-cycloalkyl-, a heterocyclyl-, a phenyl, a heteroaryl, a phenyl-$C_1$-$C_3$-alkyl- or a heteroaryl-$C_1$-$C_3$-alkyl- group,
  wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$.

In another embodiment the invention relates to compounds of formula (I), in which $R^1$ represents a $C_1$-$C_3$-alkyl-, a $C_3$-$C_5$-cycloalkyl-, a 4- to 7-membered heterocyclic ring, a phenyl, a heteroaryl, a phenyl-$C_1$-$C_2$-alkyl- or a heteroaryl-$C_1$-$C_2$-alkyl- group,
  wherein said group is optionally substituted with one or two or three substituents, identically or differently, selected from the group of hydroxy, cyano, halogen, halo-$C_1$-$C_2$-alkyl-, $C_1$-$C_3$-alkoxy-, $C_1$-$C_2$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$.

In another embodiment the invention relates to compounds of formula (I), in which $R^1$ represents a group selected from $C_1$-$C_6$-alkyl-, $C_3$-$C_7$-cycloalkyl, phenyl, or phenyl-$C_1$-$C_3$-alkyl-,
  wherein said group is optionally substituted with one or two or three substituents, identically or differently, selected from the group of hydroxy, cyano, halogen, halo-$C_1$-$C_3$-alkyl-, $C_1$-$C_3$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$.

In another embodiment the invention relates to compounds of formula (I), in which $R^1$ represents a phenyl or a heteroaryl group,
  wherein said group is optionally substituted with one or two or three substituents, identically or differently, selected from the group of hydroxy, cyano, halogen, halo-$C_1$-$C_2$-alkyl-, $C_1$-$C_3$-alkoxy-, $C_1$-$C_2$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$.

In another embodiment the invention relates to compounds of formula (I), in which $R^1$ represents a group selected from $C_1$-$C_6$-alkyl-, $C_3$-$C_7$-cycloalkyl, phenyl, or phenyl-$C_1$-$C_3$-alkyl-,
  wherein said group is optionally substituted with one or two or three substituents, identically or differently, selected from the group of hydroxy, cyano, halogen, halo-$C_1$-$C_3$-alkyl-, $C_1$-$C_3$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$.

In another embodiment the invention relates to compounds of formula (I), in which $R^1$ represents a group selected from $C_1$-$C_6$-alkyl-, $C_3$-$C_7$-cycloalkyl or phenyl-$C_1$-$C_3$-alkyl-,
  wherein said group is optionally substituted with one or two or three substituents, identically or differently, selected from the group of hydroxy or $C_1$-$C_6$-alkoxy.

In another embodiment the invention relates to compounds of formula (I), in which $R^1$ represents a group selected from $C_1$-$C_4$-alkyl-, $C_3$-$C_6$-cycloalkyl or phenyl-$C_1$-$C_2$-alkyl-,
  wherein said group is optionally substituted with one or two or three substituents, identically or differently, selected from the group of hydroxy or $C_1$-$C_3$-alkoxy.

In a preferred embodiment the invention relates to compounds of formula (I), in which $R^1$ represents a group selected from $C_1$-$C_6$-alkyl-,
  wherein said group is optionally substituted with one substituent selected from the group of $C_1$-$C_3$-alkoxy, —$NH_2$, alkylamino-, dialkylamino-, cyclic amines, hydroxy, —OP(O)(OH)$_2$.

In another preferred embodiment the invention relates to compounds of formula (I), in which $R^1$ represents a group selected from methyl, ethyl, isopropyl, cyclopropyl, tert-butyl, cyclopentyl, cyclohexyl or phenyl;
  wherein said group is optionally substituted with one substituent selected from the group of hydroxyl, methoxy, —OP(O)(OH)$_2$.

In another preferred embodiment the invention relates to compounds of formula (I), in which $R^1$ represents a $C_1$-$C_3$-alkyl group,
  wherein said group is optionally substituted with one substituent selected from the group of $C_1$-$C_3$-alkoxy, —$NH_2$, alkylamino-, dialkylamino-, or cyclic amines.

In another preferred embodiment the invention relates to compounds of formula (I), in which $R^1$ represents a group selected from $C_1$-$C_6$-alkyl-,
  wherein said group is optionally substituted with one substituent selected from the group of —$NH_2$, hydroxy, —OP(O)(OH)$_2$.

In another preferred embodiment the invention relates to compounds of formula (I), in which $R^1$ represents a $C_1$-$C_3$-alkyl group.

In a particularly preferred embodiment the invention relates to compounds of formula (I), in which $R^1$ represents a methyl or 2-methoxyethyl group.

In a particularly preferred embodiment the invention relates to compounds of formula (I), in which $R^1$ represents a methyl, 2-aminoethyl or 2-methoxyethyl group.

In a particularly preferred embodiment the invention relates to compounds of formula (I), in which $R^1$ represents a methyl group.

In a particularly preferred embodiment the invention relates to compounds of formula (I), in which $R^1$ represents a 2-methoxyethyl group.

In a particularly preferred embodiment the invention relates to compounds of formula (I), in which $R^1$ represents a 2-aminoethyl group.

In another embodiment the invention relates to compounds of formula (I), in which $R^2$ represents the group

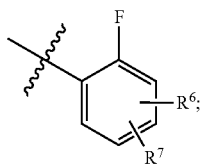

with $R^6$ and $R^7$ representing, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In a preferred embodiment the invention relates to compounds of formula (I), in which $R^2$ represents the group

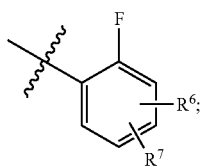

with $R^6$ and $R^7$ representing, independently from each other, a group selected from a hydrogen atom, fluoro atom, $C_1$-$C_3$ alkyl.

In another preferred embodiment the invention relates to compounds of formula (I), in which $R^2$ represents the group

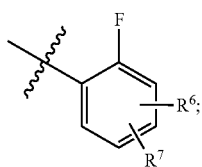

with $R^6$ and $R^7$ representing, independently from each other, a group selected from a hydrogen atom or a fluoro atom.

In a particularly preferred embodiment the invention relates to compounds of formula (I), in which $R^2$ represents a 2,4-difluorophenyl group.

In another embodiment the invention relates to compounds of formula (I), in which $R^3$ and $R^4$ represent, independently from each other, a group selected from a hydrogen atom, halogen atom, cyano, —$SF_5$, $C_1$-$C_3$-alkyl-, $C_1$-$C_3$-alkoxy-, hydroxy, halo-$C_1$-$C_3$-alkyl-, $C_1$-$C_3$-fluoroalkoxy-.

In another embodiment the invention relates to compounds of formula (I), in which $R^3$ and $R^4$, represent, independently from each other, a group selected from a hydrogen atom, halogen atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$ and $R^4$, represent, independently from each other, a group selected from a hydrogen atom, halogen atom, —$SF_5$, $C_1$-$C_3$-alkyl-, $C_1$-$C_3$-alkoxy-, halo-$C_1$-$C_3$-alkyl-, $C_1$-$C_3$-fluoroalkoxy-.

In a preferred embodiment the invention relates to compounds of formula (I), in which $R^3$ represents a group selected from a hydrogen atom, halogen atom, $C_1$-$C_3$-alkyl, $C_1$-$C_3$-alkoxy, or halo-$C_1$-$C_3$-alkyl-, and in which $R^4$ represents a hydrogen atom or a fluoro atom.

In a preferred embodiment the invention relates to compounds of formula (I), in which $R^3$ represents a group selected from a hydrogen atom, halogen atom, —$SF_5$, $C_1$-$C_3$-alkyl, $C_1$-$C_3$-alkoxy, or halo-$C_1$-$C_3$-alkyl-, and in which $R^4$ represents a hydrogen atom or a fluoro atom.

In another preferred embodiment the invention relates to compounds of formula (I), in which $R^3$ represents a group selected from a halogen atom, $C_1$-$C_3$-alkyl-, or $C_1$-$C_3$-fluoroalkyl-, and in which $R^4$ represents a hydrogen atom.

In another preferred embodiment the invention relates to compounds of formula (I), in which $R^3$ represents a group selected from a halogen atom, —$SF_5$, $C_1$-$C_3$-alkyl-, or fluoro-$C_1$-$C_3$-alkyl-, and in which $R^4$ represents a hydrogen atom.

In another preferred embodiment the invention relates to compounds of formula (I), in which $R^3$ represents a group selected from hydrogen, fluoro, chloro, bromo, methyl, methoxy or trifluoromethyl, and in which $R^4$ represents a hydrogen atom.

In another preferred embodiment the invention relates to compounds of formula (I), in which $R^3$ represents a group selected from hydrogen, fluoro, chloro, bromo, —$SF_5$, methyl, methoxy or trifluoromethyl, and in which $R^4$ represents a hydrogen atom.

In a particularly preferred embodiment the invention relates to compounds of formula (I), in which $R^3$ represents a group selected from fluoro, chloro, bromo, methyl or trifluoromethyl, and in which $R^4$ represents a hydrogen atom.

In a particularly preferred embodiment the invention relates to compounds of formula (I), in which $R^3$ represents a group selected from fluoro, chloro, bromo, —$SF_5$, methyl or trifluoromethyl, and in which $R^4$ represents a hydrogen atom.

In another particularly preferred embodiment the invention relates to compounds of formula (I), in which $R^3$ represents a trifluoromethyl group, and in which $R^4$ represents a hydrogen atom.

In another particularly preferred embodiment the invention relates to compounds of formula (I), in which $R^3$ represents a —$SF_5$ or trifluoromethyl group, and in which $R^4$ represents a hydrogen atom.

In another particularly preferred embodiment the invention relates to compounds of formula (I), in which $R^3$ represents a —$SF_5$ group, and in which $R^4$ represents a hydrogen atom.

In another embodiment the invention relates to compounds of formula (I), in which $R^3$ represents, a group selected from a hydrogen atom, halogen atom, cyano, —$SF_5$, $C_1$-$C_3$-alkyl-, $C_1$-$C_3$-alkoxy-, hydroxy, halo-$C_1$-$C_3$-alkyl-, $C_1$-$C_3$-fluoroalkoxy-.

In another embodiment the invention relates to compounds of formula (I), in which $R^3$ represents a group selected from a hydrogen atom, halogen atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$ represents a group selected from a hydrogen atom, halogen atom, —$SF_5$, $C_1$-$C_3$-alkyl-, $C_1$-$C_3$-alkoxy-, halo-$C_1$-$C_3$-alkyl-, $C_1$-$C_3$-fluoroalkoxy-.

In a preferred embodiment the invention relates to compounds of formula (I), in which $R^3$ represents a group selected from a hydrogen atom, halogen atom, $C_1$-$C_3$-alkyl-, $C_1$-$C_3$-alkoxy-, or halo-$C_1$-$C_3$-alkyl.

In a preferred embodiment the invention relates to compounds of formula (I), in which $R^3$ represents a group selected from a hydrogen atom, halogen atom, —$SF_5$, $C_1$-$C_3$-alkyl-, $C_1$-$C_3$-alkoxy-, or halo-$C_1$-$C_3$-alkyl.

In another preferred embodiment the invention relates to compounds of formula (I), in which $R^3$ represents a halogen atom.

In another preferred embodiment the invention relates to compounds of formula (I), in which $R^3$ represents a $C_1$-$C_3$-alkyl group.

In another preferred embodiment the invention relates to compounds of formula (I), in which $R^3$ represents a halo-$C_1$-$C_3$-alkyl group.

In another preferred embodiment the invention relates to compounds of formula (I), in which $R^3$ represents a —$SF_5$ group.

In another preferred embodiment the invention relates to compounds of formula (I), in which $R^3$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another preferred embodiment the invention relates to compounds of formula (I), in which $R^3$ represents a group selected from a halogen atom, $C_1$-$C_3$-alkyl-, or $C_1$-$C_3$-fluoroalkyl-.

In another preferred embodiment the invention relates to compounds of formula (I), in which $R^3$ represents a group selected from a halogen atom, —$SF_5$, $C_1$-$C_3$-alkyl-, or fluoro-$C_1$-$C_3$-alkyl-.

In another preferred embodiment the invention relates to compounds of formula (I), in which $R^3$ represents a group selected from hydrogen, fluoro, chloro, bromo, methyl, methoxy or trifluoromethyl.

In another preferred embodiment the invention relates to compounds of formula (I), in which $R^3$ represents a group selected from hydrogen, fluoro, chloro, bromo, —$SF_5$, methyl, methoxy or trifluoromethyl.

In another preferred embodiment the invention relates to compounds of formula (I), in which $R^3$ represents a group selected from fluoro, chloro, bromo, —$SF_5$, methyl, methoxy or trifluoromethyl.

In another preferred embodiment the invention relates to compounds of formula (I), in which $R^3$ represents a fluoro atom.

In another preferred embodiment the invention relates to compounds of formula (I), in which $R^3$ represents a chloro atom.

In another preferred embodiment the invention relates to compounds of formula (I), in which $R^3$ represents a bromo atom.

In another preferred embodiment the invention relates to compounds of formula (I), in which $R^3$ represents a methyl group.

In another preferred embodiment the invention relates to compounds of formula (I), in which $R^3$ represents a methoxy group.

In a particularly preferred embodiment the invention relates to compounds of formula (I), in which $R^3$ represents a group selected from fluoro, chloro, bromo, methyl or trifluoromethyl.

In a particularly preferred embodiment the invention relates to compounds of formula (I), in which $R^3$ represents a group selected from fluoro, chloro, bromo, —$SF_5$, methyl or trifluoromethyl.

In another particularly preferred embodiment the invention relates to compounds of formula (I), in which $R^3$ represents a trifluoromethyl group.

In another embodiment the invention relates to compounds of formula (I), in which $R^4$ represents a group selected from a hydrogen atom, halogen atom, cyano, —$SF_5$, $C_1$-$C_3$-alkyl-, $C_1$-$C_3$-alkoxy-, hydroxy, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, halogen atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, halogen atom, —$SF_5$, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom or a halogen atom.

In a preferred embodiment the invention relates to compounds of formula (I), in which $R^4$ represents a group selected from a hydrogen atom or a fluoro atom.

In another preferred embodiment the invention relates to compounds of formula (I), in which $R^4$ represents a fluoro atom.

In a particularly preferred embodiment the invention relates to compounds of formula (I), in which $R^4$ represents a hydrogen atom.

In another embodiment the invention relates to compounds of formula (I), in which $R^5$ represents a group selected from a hydrogen atom, cyano, —C(O)$R^8$, —C(O)O$R^8$, —S(O)$_2R^8$, —C(O)N$R^9R^{10}$, —P(O)(O$R)_2$, —$CH_2$OP(O$R)_2$, $C_1$-$C_6$-alkyl-, $C_3$-$C_7$-cycloalkyl-, heterocyclyl-, phenyl, heteroaryl, wherein said $C_1$-$C_6$-alkyl-, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^5$ represents a group selected from a hydrogen atom, cyano, —C(O)$R^8$, —S(O)$_2R^8$, —C(O)N$R^9R^{10}$, —P(O)(O$R^{11})_2$, —$CH_2$OP(O$R^{11})_2$, $C_1$-$C_6$-alkyl-, $C_3$-$C_7$-cycloalkyl-, heterocyclyl-, phenyl, heteroaryl, wherein said $C_1$-$C_6$-alkyl-, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^5$ represents a group selected from a hydrogen atom, cyano, —C(O)$R^8$, —C(O)O$R^8$, —S(O)$_2R^8$, —C(O)N$R^9R^{10}$, —P(O)(O$R)_2$, —$CH_2$OP(O$R)_2$, $C_1$-$C_3$-alkyl-, $C_3$-$C_5$-cycloalkyl-, phenyl, wherein said $C_1$-$C_3$-alkyl-, $C_3$-$C_5$-cycloalkyl- or phenyl group is optionally substituted with one or two substituents, identically or differently, selected from hydroxy, —$NH_2$, alkylamino-, dialkylamino-, cyclic amines.

In another embodiment the invention relates to compounds of formula (I), in which $R^5$ represents a group selected from a hydrogen atom, cyano, —C(O)$R^8$, —S(O)$_2R^8$, —C(O)N$R^9R^{10}$, —P(O)(O$R^{11}$)$_2$, —$CH_2$OP(O$R^{11}$)$_2$, $C_1$-$C_3$-alkyl-, $C_3$-$C_5$-cycloalkyl-, phenyl,
wherein said $C_1$-$C_3$-alkyl-, $C_3$-$C_5$-cycloalkyl- or phenyl group is optionally substituted with one or two substituents, identically or differently, selected from hydroxy, —$NH_2$, alkylamino-, dialkylamino-, cyclic amines.

In another embodiment the invention relates to compounds of formula (I), in which $R^5$ represents a group selected from a hydrogen atom, cyano, —C(O)$R^8$, —C(O)O$R^8$, —S(O)$_2R^8$, —C(O)N$R^9R^{10}$, —P(O)(OR)$_2$, —$CH_2$OP(OR)$_2$, methyl-.

In another embodiment the invention relates to compounds of formula (I), in which $R^5$ represents a group selected from a hydrogen atom, cyano, —C(O)$R^8$, —S(O)$_2R^8$, —C(O)N$R^9R^{10}$, —P(O)(O$R^{11}$)$_2$, —$CH_2$OP(O$R^{11}$)$_2$, methyl-.

In another embodiment the invention relates to compounds of formula (I), in which $R^5$ represents a group selected from cyano, —C(O)$R^8$, —C(O)O$R^8$, —S(O)$_2R^8$, —C(O)N$R^9R^{10}$, —P(O)(OR)$_2$, —$CH_2$OP(OR)$_2$, methyl-.

In another embodiment the invention relates to compounds of formula (I), in which $R^5$ represents a group selected from cyano, —C(O)$R^8$, —S(O)$_2R^8$, —C(O)N$R^9R^{10}$, —P(O)(O$R^{11}$)$_2$, —$CH_2$OP(O$R^{11}$)$_2$, methyl-.

In a preferred embodiment the invention relates to compounds of formula (I), in which $R^5$ represents a group selected from a hydrogen atom, cyano, —C(O)O$R^8$, —C(O)N$R^9R^{10}$, —P(O)(OR)$_2$, —$CH_2$OP(OR)$_2$, or $C_1$-$C_3$-alkyl-,
wherein said $C_1$-$C_3$-alkyl group is optionally substituted with one substituent, selected from —$NH_2$, alkylamino-, dialkylamino-, or cyclic amines.

In a preferred embodiment the invention relates to compounds of formula (I), in which $R^5$ represents a group selected from a hydrogen atom, cyano, —C(O)N$R^9R^{10}$, —P(O)(O$R^{11}$)$_2$, —$CH_2$OP(O$R^{11}$)$_2$, or $C_1$-$C_3$-alkyl-,
wherein said $C_1$-$C_3$-alkyl group is optionally substituted with one substituent, selected from —$NH_2$, alkylamino-, dialkylamino-, or cyclic amines.

In another preferred embodiment the invention relates to compounds of formula (I), in which $R^5$ represents a group selected from a hydrogen atom, cyano or —C(O)N$R^9R^{10}$.

In another preferred embodiment the invention relates to compounds of formula (I), in which $R^5$ represents a —C(O)N$R^9R^{10}$ group.

In a particularly preferred embodiment the invention relates to compounds of formula (I), in which $R^5$ represents a group selected from a hydrogen atom, cyano, —C(O)O$C_2H_5$, —C(O)$NH_2$.

In another particularly preferred embodiment the invention relates to compounds of formula (I), in which $R^5$ represents a group selected from a hydrogen atom, cyano, —C(O)$NH_2$.

In another particularly preferred embodiment the invention relates to compounds of formula (I), in which $R^5$ represents a hydrogen atom.

In another particularly preferred embodiment the invention relates to compounds of formula (I), in which $R^5$ represents a cyano group.

In another particularly preferred embodiment the invention relates to compounds of formula (I), in which $R^5$ represents a —C(O)$NH_2$ group.

In another embodiment the invention relates to compounds of formula (I), in which $R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^6$ and $R^7$ represent, independently from each other, a group selected from a hydrogen or fluoro atom or $C_1$-$C_3$-alkoxy-.

In a preferred embodiment the invention relates to compounds of formula (I), in which $R^6$ and $R^7$ represent, independently from each other, a group selected from a hydrogen atom, fluoro atom, $C_1$-$C_3$ alkyl-.

In another preferred embodiment the invention relates to compounds of formula (I), in which $R^6$ and $R^7$ represent, independently from each other, a group selected from a hydrogen atom or a fluoro atom.

In another preferred embodiment the invention relates to compounds of formula (I), in which $R^6$ represents a fluoro atom and $R^7$ represents a hydrogen atom.

In a particularly preferred embodiment the invention relates to compounds of formula (I), in which $R^6$ is in para position to the 5-fluoro pyrimidine and represents a fluoro atom and $R^7$ represents a hydrogen atom.

In another embodiment the invention relates to compounds of formula (I), in which $R^6$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^6$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^6$ represents a group selected from a hydrogen atom, fluoro atom, chloro atom.

In a preferred embodiment the invention relates to compounds of formula (I), in which $R^6$ represents a group selected from a hydrogen atom, fluoro atom, $C_1$-$C_3$ alkyl-.

In another preferred embodiment the invention relates to compounds of formula (I), in which $R^6$ represents a group selected from a hydrogen atom or a fluoro atom.

In another preferred embodiment the invention relates to compounds of formula (I), in which $R^6$ represents a hydrogen atom.

In another preferred embodiment the invention relates to compounds of formula (I), in which $R^6$ represents a fluoro atom.

In a particularly preferred embodiment the invention relates to compounds of formula (I), in which $R^6$ is in para position to the 5-fluoro pyrimidine and represents a fluoro atom.

In another embodiment the invention relates to compounds of formula (I), in which $R^7$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^7$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^7$ represents a group selected from a hydrogen atom, fluoro atom, chloro atom.

In a preferred embodiment the invention relates to compounds of formula (I), in which $R^7$ represents a group selected from a hydrogen atom, fluoro atom, $C_1$-$C_3$ alkyl-.

In another preferred embodiment the invention relates to compounds of formula (I), in which $R^7$ represents a group selected from a hydrogen atom or a fluoro atom.

In another preferred embodiment the invention relates to compounds of formula (I), in which $R^7$ represents a fluoro atom.

In another preferred embodiment the invention relates to compounds of formula (I), in which $R^7$ is in para position to the 5-fluoro pyrimidine and represents a fluoro atom.

In a particularly preferred embodiment the invention relates to compounds of formula (I), in which $R^7$ represents a hydrogen atom.

In another embodiment the invention relates to compounds of formula (I), in which $R^8$ represents a group selected from $C_1$-$C_6$-alkyl-, $C_3$-$C_7$-cycloalkyl-, heterocyclyl-, phenyl, benzyl or heteroaryl,
  wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^8$ represents a group selected from $C_1$-$C_6$-alkyl-.

In another embodiment the invention relates to compounds of formula (I), in which $R^8$ represents a group selected from $C_1$-$C_5$-alkyl-, $C_3$-$C_6$-cycloalkyl-, heterocyclyl-, phenyl, benzyl or heteroaryl
  wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^8$ represents a group selected from $C_1$-$C_3$-alkyl-, $C_3$-$C_5$-cycloalkyl-, heterocyclyl-, phenyl or benzyl,
  wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^8$ represents a group selected from $C_1$-$C_3$-alkyl-, $C_3$-$C_5$-cycloalkyl-, or benzyl,
  wherein said group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-.

In another preferred embodiment the invention relates to compounds of formula (I), in which $R^8$ represents a $C_1$-$C_3$-alkyl- group,
  wherein said group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-.

In another preferred embodiment the invention relates to compounds of formula (I), in which $R^8$ represents a $C_3$-$C_5$-cycloalkyl- group,
  wherein said group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-.

In another preferred embodiment the invention relates to compounds of formula (I), in which $R^8$ represents a benzyl group,
  wherein said group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-.

In another preferred embodiment the invention relates to compounds of formula (I), in which $R^8$ represents a group selected from $C_1$-$C_3$-alkyl- which is optionally substituted with $C_1$-$C_3$-alkoxy.

In a preferred embodiment the invention relates to compounds of formula (I), in which $R^8$ represents a $C_1$-$C_3$-alkyl group.

In a particularly preferred embodiment the invention relates to compounds of formula (I), in which $R^8$ represents an ethyl group.

In another embodiment the invention relates to compounds of formula (I), in which $R^9$, $R^{10}$ represent, independently from each other, a group selected from hydrogen, $C_1$-$C_6$-alkyl-, $C_3$-$C_7$-cycloalkyl-, heterocyclyl-, phenyl, benzyl or heteroaryl,
  wherein said $C_1$-$C_6$-alkyl-, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or
$R^9$ and $R^{10}$, together with the nitrogen atom they are attached to, form a cyclic amine.

In another embodiment the invention relates to compounds of formula (I), in which $R^9$ and $R^{10}$ represent, independently from each other, a group selected from hydrogen, $C_1$-$C_5$-alkyl-, $C_3$-$C_6$-cycloalkyl-, heterocyclyl-, phenyl or heteroaryl,
  wherein said $C_1$-$C_5$-alkyl, $C_3$-$C_6$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^9$, $R^{10}$ represent, independently from each other, a group selected from hydrogen, $C_1$-$C_3$-alkyl-, $C_3$-$C_5$-cycloalkyl-, heterocyclyl-, phenyl or benzyl,
  wherein said $C_1$-$C_3$-alkyl, $C_3$-$C_5$-cycloalkyl-, heterocyclyl-, phenyl or benzyl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-; or
$R^9$ and $R^{10}$, together with the nitrogen atom they are attached to, form a cyclic amine.

In a preferred embodiment the invention relates to compounds of formula (I), in which $R^9$ and $R^{10}$ represent, independently from each other, a group selected from hydrogen, $C_1$-$C_3$-alkyl-, $C_3$-$C_5$-cycloalkyl-, or benzyl,
  wherein said group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-; or
$R^9$ and $R^{10}$, together with the nitrogen atom they are attached to, form a cyclic amine.

In another preferred embodiment the invention relates to compounds of formula (I), in which $R^9$ and $R^{10}$ represent, independently from each other, hydrogen or a $C_1$-$C_6$-alkyl-.

In another preferred embodiment the invention relates to compounds of formula (I), in which $R^9$ and $R^{10}$ represent, independently from each other, hydrogen or a $C_1$-$C_2$-alkyl-.

In a particularly preferred embodiment the invention relates to compounds of formula (I), in which $R^9$ and $R^{10}$ represent hydrogen.

In another embodiment the invention relates to compounds of formula (I), in which $R^9$ represents a group selected from hydrogen, $C_1$-$C_6$-alkyl-, $C_3$-$C_7$-cycloalkyl-, heterocyclyl-, phenyl, benzyl or heteroaryl,
  wherein said $C_1$-$C_6$-alkyl, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^9$ represents a group selected from hydrogen, $C_1$-$C_3$-alkyl-, $C_3$-$C_5$-cycloalkyl-, or benzyl,
  wherein said group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-.

In another preferred embodiment the invention relates to compounds of formula (I), in which $R^9$ represents hydrogen or a $C_1$-$C_6$-alkyl-.

In another preferred embodiment the invention relates to compounds of formula (I), in which $R^9$ represents hydrogen or a $C_1$-$C_2$-alkyl-.

In a particularly preferred embodiment the invention relates to compounds of formula (I), in which $R^9$ represents hydrogen.

In another embodiment the invention relates to compounds of formula (I), in which $R^{10}$ represents a group selected from hydrogen, $C_1$-$C_6$-alkyl-, $C_3$-$C_7$-cycloalkyl-, heterocyclyl-, phenyl, benzyl or heteroaryl,
  wherein said $C_1$-$C_6$-alkyl, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^{10}$ represents a group selected from hydrogen, $C_1$-$C_3$-alkyl-, $C_3$-$C_5$-cycloalkyl-, or benzyl,
  wherein said group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-.

In another preferred embodiment the invention relates to compounds of formula (I), in which $R^{10}$ represents hydrogen or a $C_1$-$C_6$-alkyl-.

In another preferred embodiment the invention relates to compounds of formula (I), in which $R^{10}$ represents hydrogen or a $C_1$-$C_2$-alkyl-.

In a particularly preferred embodiment the invention relates to compounds of formula (I), in which $R^{10}$ represents hydrogen.

In another embodiment the invention relates to compounds of formula (I), in which $R^{11}$ represents a group selected from hydrogen, $C_1$-$C_4$-alkyl or benzyl.

In another preferred embodiment the invention relates to compounds of formula (I), in which $R^{11}$ represents a group selected from hydrogen or $C_1$-$C_4$-alkyl.

In a preferred embodiment the invention relates to compounds of formula (I), in which $R^{11}$ represents a group selected from hydrogen or $C_1$-$C_2$-alkyl.

It is to be understood that the present invention relates to any sub-combination within any embodiment of the present invention of compounds of formula (I), supra.

In another preferred embodiment the invention relates to a specific stereoisomer of compounds of the formula (I) featuring a lower $IC_{50}$ vs CDK9 as compared to other stereoisomers of the respective compound, determined according to Method 1a described in the Materials and Methods section below.

In another preferred embodiment the invention relates to a specific stereoisomer of compounds of the formula (I) featuring a lower $IC_{50}$ vs CDK9 at high ATP concentration as compared to other stereoisomers of the respective compound, determined according to Method 1b described in the Materials and Methods section below.

In another preferred embodiment the invention relates to a specific stereoisomer of compounds of the formula (I) featuring a higher selectivity in favor of CDK9 over CDK2 as compared to other stereoisomers of the respective compound, determined according to Methods 1a (CDK9) and 2 (CDK2) described in the Materials and Methods section below.

In another preferred embodiment the invention relates to a specific stereoisomer of compounds of the formula (I) featuring a higher anti-proliferative activity in tumor cell lines such as HeLa as compared to other stereoisomers of the respective compound, determined according to Method 3 described in the Materials and Methods section below.

In another preferred embodiment the invention relates to a specific stereoisomer of compounds of the formula (I) featuring a higher metabolic stability in vitro in rat hepatocytes as compared to other stereoisomers of the respective compound, determined according to Method 5 described in the Materials and Methods section below.

In another preferred embodiment the invention relates to a specific stereoisomer of compounds of the formula (I) featuring a longer terminal half-life upon intravenous administration in rats in vivo, as compared to other stereoisomers of the respective compound, determined according to Method 6 described in the Materials and Methods section below.

More particularly still, the present invention covers compounds of formula (I) which are disclosed in the Example section of this text, infra.

Very specially preferred are combinations of two or more of the abovementioned preferred embodiments.

In particular, preferred subjects of the present invention are the compounds selected from:

(rac)-{[3-{[4-(2,4-Difluorophenyl)-5-fluoropyrimidin-2-yl]amino}-5-(trifluoromethyl)benzyl](methyl)oxido-$\lambda^6$-sulfanylidene}cyanamide;

{[3-{[4-(2,4-Difluorophenyl)-5-fluoropyrimidin-2-yl]amino}-5-(trifluoromethyl)benzyl](methyl)oxido-$\lambda^6$-sulfanylidene}cyanamide, enantiomer 1;

{[3-{[4-(2,4-Difluorophenyl)-5-fluoropyrimidin-2-yl]amino}-5-(trifluoromethyl)benzyl](methyl)oxido-$\lambda^6$-sulfanylidene}cyanamide, enantiomer 2;

(rac)-4-(2,4-Difluorophenyl)-5-fluoro-N-{3-[(S-methylsulfonimidoyl)methyl]-5-(trifluoromethyl)phenyl}pyrimidin-2-amine;

4-(2,4-Difluorophenyl)-5-fluoro-N-{3-[(S-methylsulfonimidoyl)methyl]-5-(trifluoromethyl)phenyl}pyrimidin-2-amine, enantiomer 1;

4-(2,4-Difluorophenyl)-5-fluoro-N-{3-[(S-methylsulfonimidoyl)methyl]-5-(trifluoromethyl)phenyl}pyrimidin-2-amine, enantiomer 2;

(rac)-1-{[3-{[4-(2,4-Difluorophenyl)-5-fluoropyrimidin-2-yl]amino}-5-(trifluoromethyl)benzyl](methyl)oxido-$\lambda^6$-sulfanylidene}urea;

(rac)-Ethyl[(3-{[4-(2,4-difluorophenyl)-5-fluoropyrimidin-2-yl]amino}benzyl)(methyl)oxido-$\lambda^6$-sulfanylidene]carbamate;

(rac)-4-(2,4-Difluorophenyl)-5-fluoro-N-{3-[(S-methylsulfonimidoyl)methyl]phenyl}pyrimidin-2-amine;

(rac)-[(3-{[4-(2,4-Difluorophenyl)-5-fluoropyrimidin-2-yl]amino}-5-fluorobenzyl)(methyl)oxido-$\lambda^6$-sulfanylidene]cyanamide;

(rac)-4-(2,4-Difluorophenyl)-5-fluoro-N-{3-fluoro-5-[(S-methylsulfonimidoyl)methyl]phenyl}pyrimidin-2-amine;

4-(2,4-Difluorophenyl)-5-fluoro-N-{3-fluoro-5-[(S-methylsulfonimidoyl)methyl]phenyl}pyrimidin-2-amine; enantiomer 1;

4-(2,4-Difluorophenyl)-5-fluoro-N-{3-fluoro-5-[(S-methylsulfonimidoyl)methyl]phenyl}pyrimidin-2-amine; enantiomer 2;

(rac)-[(3-Chloro-5-{[4-(2,4-difluorophenyl)-5-fluoropyrimidin-2-yl]amino}benzyl)(methyl)oxido-$\lambda^6$-sulfanylidene]cyanamide;

(rac)-N-{3-chloro-5-[(S-methylsulfonimidoyl)methyl]phenyl}-4-(2,4-difluorophenyl)-5-fluoropyrimidin-2-amine;

(rac)-[(3-{[4-(2,4-Difluorophenyl)-5-fluoropyrimidin-2-yl]amino}-5-methylbenzyl)(methyl)oxido-$\lambda^6$-sulfanylidene]cyanamide;

(rac)-4-(2,4-Difluorophenyl)-5-fluoro-N-{3-methyl-5-[(S-methylsulfonimidoyl)methyl]phenyl}pyrimidin-2-amine;

(rac)-[(3-Bromo-5-{[4-(2,4-difluorophenyl)-5-fluoropyrimidin-2-yl]amino}benzyl)(methyl)oxido-$\lambda^6$-sulfanylidene]cyanamide;

(rac)-N-{3-Bromo-5-[(S-methylsulfonimidoyl)methyl]phenyl}-4-(2,4-difluorophenyl)-5-fluoropyrimidin-2-amine;

(rac)-[(3-{[4-(2,4-Difluorophenyl)-5-fluoropyrimidin-2-yl]amino}-5-methoxybenzyl)(methyl)oxido-$\lambda^6$-sulfanylidene]cyanamide;

(rac)-4-(2,4-Difluorophenyl)-5-fluoro-N-{3-methoxy-5-[(S-methylsulfonimidoyl)methyl]phenyl}pyrimidin-2-amine;

(rac)-{[3-{[4-(2,4-Difluorophenyl)-5-fluoropyrimidin-2-yl]amino}-5-(trifluoromethyl)benzyl](2-methoxyethyl)oxido-$\lambda^6$-sulfanylidene}cyanamide;

1-{[3-{[4-(2,4-Difluorophenyl)-5-fluoropyrimidin-2-yl]amino}-5-(trifluoromethyl)benzyl](methyl)oxido-$\lambda^6$-sulfanylidene}urea; enantiomer 1;

1-{[3-{[4-(2,4-Difluorophenyl)-5-fluoropyrimidin-2-yl]amino}-5-(trifluoromethyl)benzyl](methyl)oxido-$\lambda^6$-sulfanylidene}urea; enantiomer 2;

(rac)-N-[3-{[S-(2-Aminoethyl)sulfonimidoyl]methyl}-5-(trifluoromethyl)phenyl]-4-(2,4-difluorophenyl)-5-fluoropyrimidin-2-amine trifluoroacetate;

N-[3-{[S-(2-Aminoethyl)sulfonimidoyl]methyl}-5-(trifluoromethyl)phenyl]-4-(2,4-difluorophenyl)-5-fluoropyrimidin-2-amine; enantiomer 1;

N-[3-{[S-(2-Aminoethyl)sulfonimidoyl]methyl}-5-(trifluoromethyl)phenyl]-4-(2,4-difluorophenyl)-5-fluoropyrimidin-2-amine; enantiomer 2;

(rac)-{[3-{[4-(2,4-Difluorophenyl)-5-fluoropyrimidin-2-yl]amino}-5-(pentafluoro-$\lambda^6$-sulfanyl)benzyl](methyl)oxido-$\lambda^6$-sulfanylidene}cyanamide;

{[3-{[4-(2,4-Difluorophenyl)-5-fluoropyrimidin-2-yl]amino}-5-(pentafluoro-$\lambda^6$-sulfanyl)benzyl](methyl)oxido-$\lambda^6$-sulfanylidene}cyanamide; enantiomer 1;

{[3-{[4-(2,4-Difluorophenyl)-5-fluoropyrimidin-2-yl]amino}-5-(pentafluoro-$\lambda^6$-sulfanyl)benzyl](methyl)oxido-$\lambda^6$-sulfanylidene}cyanamide; enantiomer 2;

4-(2,4-Difluorophenyl)-5-fluoro-N-{3-[(S-methylsulfonimidoyl)methyl]-5-(pentafluoro-$\lambda^6$-sulfanyl)phenyl}pyrimidin-2-amine; enantiomer 1;

4-(2,4-Difluorophenyl)-5-fluoro-N-{3-[(S-methylsulfonimidoyl)methyl]-5-(pentafluoro-$\lambda^6$-sulfanyl)phenyl}pyrimidin-2-amine; enantiomer 2;

1-{[3-{[4-(2,4-Difluorophenyl)-5-fluoropyrimidin-2-yl]amino}-5-(pentafluoro-$\lambda^6$-sulfanyl)benzyl](methyl)oxido-$\lambda^6$-sulfanylidene}urea; enantiomer 1;

1-{[3-{[4-(2,4-Difluorophenyl)-5-fluoropyrimidin-2-yl]amino}-5-(pentafluoro-$\lambda^6$-sulfanyl)benzyl](methyl)oxido-$\lambda^6$-sulfanylidene}urea; enantiomer 2;

[(3-{[4-(2,4-Difluorophenyl)-5-fluoro-pyrimidin-2-yl]amino}-5-methylbenzyl)-(methyl)oxido-$\lambda^6$-sulfanylidene]cyanamide; enantiomer 1;

[(3-{[4-(2,4-Difluorophenyl)-5-fluoro-pyrimidin-2-yl]amino}-5-methylbenzyl)-(methyl)oxido-$\lambda^6$-sulfanylidene]cyanamide; enantiomer 2;

4-(2,4-Difluorophenyl)-5-fluoro-N-{3-methyl-5-[(S-methylsulfonimidoyl)methyl]-phenyl}pyrimidin-2-amine; enantiomer 1;

4-(2,4-Difluorophenyl)-5-fluoro-N-{3-methyl-5-[(S-methylsulfonimidoyl)methyl]-phenyl}pyrimidin-2-amine; enantiomer 2;

[(3-Bromo-5-{[4-(2,4-difluorophenyl)-5-fluoropyrimidin-2-yl]amino}benzyl)(methyl)oxido-$\lambda^6$-sulfanylidene]cyanamide; enantiomer 1;

[(3-Bromo-5-{[4-(2,4-difluorophenyl)-5-fluoropyrimidin-2-yl]amino}benzyl)(methyl)oxido-$\lambda^6$-sulfanylidene]cyanamide; enantiomer 2;

N-{3-Bromo-5-[(S-methylsulfonimidoyl)methyl]phenyl}-4-(2,4-difluorophenyl)-5-fluoropyrimidin-2-amine; enantiomer 1;

N-{3-Bromo-5-[(S-methylsulfonimidoyl)methyl]phenyl}-4-(2,4-difluorophenyl)-5-fluoropyrimidin-2-amine; enantiomer 2, and the enantiomers, diastereomers, salts, solvates or salts of solvates thereof.

The above mentioned definitions of radicals which have been detailed in general terms or in preferred ranges also apply to the end products of the formula (I) and, analogously, to the starting materials or intermediates required in each case for the preparation.

The invention furthermore relates to a process for the preparation of the compounds of formula (I) according to the invention, in which N-unprotected sulfoximines of formula (6) are reacted to give N-functionalized sulfoximines of formula (I), according to the invention, in which $R^5$ is not a hydrogen atom,

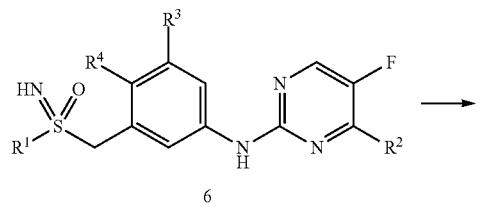

in which method the nitrogen of the sulfoximine group of compounds of formula (6), wherein $R^1$, $R^2$, $R^3$ and $R^4$ are as defined for the compound of general formula (I) according to the invention, is functionalized according to methods known in the art, thus providing a compound of general formula (I) according to the invention, in which $R^5$ is not hydrogen, and the resulting compounds are optionally, if appropriate, converted with the corresponding (i) solvents and/or (ii) bases or acids to the solvates, salts and/or solvates of the salts thereof.

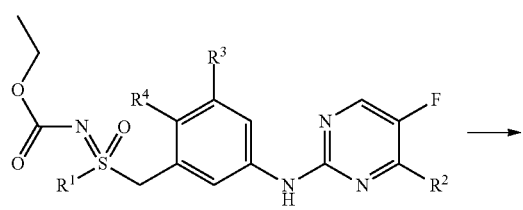

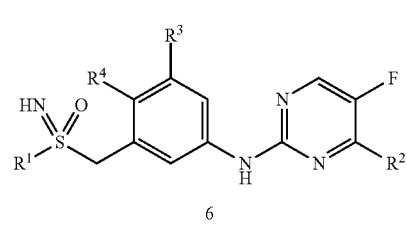

The invention therefore furthermore relates to a method for the preparation of the compounds of formula (I) according to the present invention, in which $R^5$ is a hydrogen atom (identical to the N-unprotected sulfoximines of formula (6) shown above), according to the invention, in which method the —C(O)O-ethyl group of an N-protected compound of formula (5), in which $R^1$, $R^2$, $R^3$ and $R^4$ are as defined for the compound of general formula (I) according to the present invention, is deprotected according to methods known in the art, e.g. by reacting said compound of the formula (5) with an alkoxide base, such as sodium ethoxide, in an alcoholic solvent, such as ethanol, at a temperature between 20° C. and the boiling point of the respective alcoholic solvent (see for example: U. Lücking et al, WO 2005/037800), thus providing a compound of general formula (I) according to the invention, in which $R^5$ is a hydrogen atom, and the resulting compounds (the N-unprotected sulfoximines of formula (6) shown above) are optionally, if appropriate, reacted with the corresponding (i) solvents and/or (ii) bases or acids to the solvates, salts and/or solvates of the salts thereof.

The present invention further concerns compounds of general formula (5)

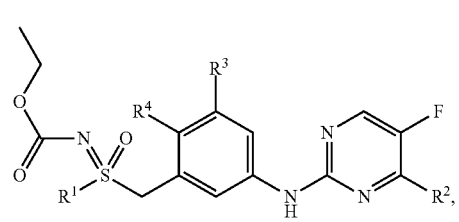

in which $R^1$, $R^2$, $R^3$ and $R^4$ are as defined for the compounds of general formula (I) of the present invention according to general formula (I), and the enantiomers, diastereomers, salts, solvates or salts of solvates thereof.

The present invention further relates to compounds of general formula (6)

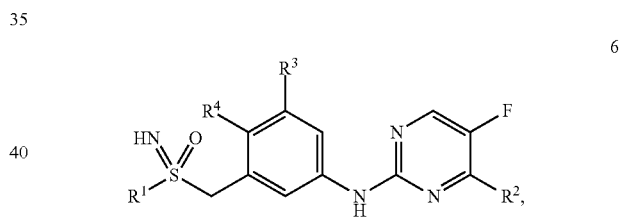

in which $R^1$, $R^2$, $R^3$ and $R^4$ are as defined for the compounds of general formula (I) of the present invention according to general formula (I), and the enantiomers, diastereomers, salts, solvates or salts of solvates thereof.

The invention furthermore relates to a method for the preparation of the compounds of general formula (I) according to the present invention, in which $R^5$ is —C(O)O-Ethyl (identical to the N-protected sulfoximines of formula (5) shown above), in which method a compound of formula (3),

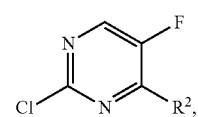

in which $R^2$ is as defined for the compound of general formula (I) according to the invention, is reacted with a compound of formula (4)

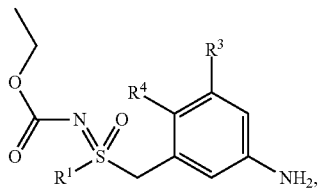

4 in which $R^1$, $R^3$ and $R^4$ are as defined for the compound of general formula (I) according to the invention, thus providing a compound of general formula (I) according to the invention, in which $R^5$ is —C(O)O-Ethyl, and the resulting compounds (see N-protected sulfoximines of formula (5) shown above) are optionally, if appropriate, converted with the corresponding (i) solvents and/or (ii) bases or acids to the solvates, salts and/or solvates of the salts thereof.

The invention furthermore relates to a method for the preparation of the compounds of formula (I) according to the present invention, in which $R^5$ is a cyano group (identical to the N-cyanosulfoximines of formula (16))

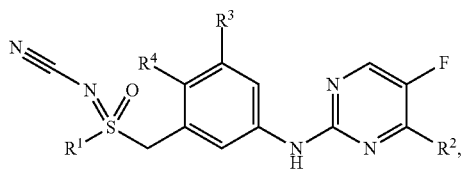

16 wherein compounds of formula (15)

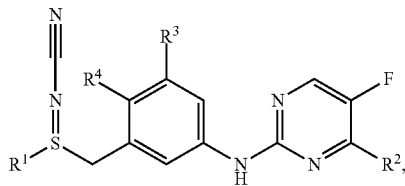

15 in which $R^1$, $R^2$, $R^3$ and $R^4$ are as defined for the compound of formula (I) according to the present invention, are oxidized using an alkali salt of permanganic acid in an aliphatic ketone of the formula $C_1$-$C_2$-alkyl-C(=O)—$C_1$-$C_2$-alkyl, to provide compounds of general formula (I) according to the invention, in which $R^5$ is a cyano group, and the resulting compounds (the N-cyanosulfoximines of formula (16) as shown above) are optionally, if appropriate, reacted with the corresponding (i) solvents and/or (ii) bases or acids to the solvates, salts and/or solvates of the salts thereof.

The present invention relates to compounds of general formula (16)

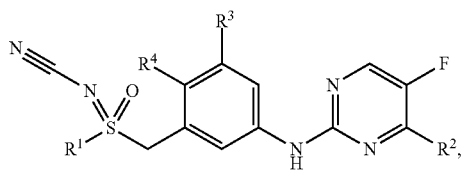

16 in which $R^1$, $R^2$, $R^3$ and $R^4$ are as defined for the compounds of the present invention according to general formula (I), and the enantiomers, diastereomers, salts, solvates or salts of solvates thereof.

The invention furthermore relates to a method for the preparation of the compounds of formula (15) according to the present invention

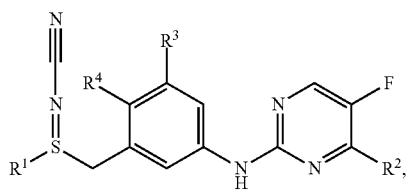

15 in which method compounds of formula (14)

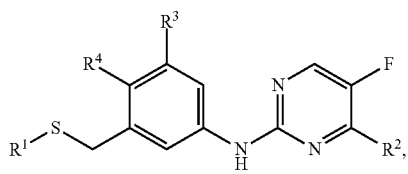

14 in which $R^1$, $R^2$, $R^3$ and $R^4$ are as defined for the compound of formula (I) according to the present invention, are reacted with cyanamide in the presence of iodobenzene diacetate in a halogenated aliphatic hydrocarbon as a solvent, or by reaction with sodium hydrogencyanamide in the presence of 1,3-dibromo-5,5-dimethylhydantoin in an aliphatic alcohol of the formula $C_1$-$C_4$-alkyl-OH as a solvent, thus providing compounds of formula (15) and the resulting compounds are optionally, if appropriate, reacted with the corresponding (i) solvents and/or (ii) bases or acids to the solvates, salts and/or solvates of the salts thereof.

The present invention further concerns compounds of general formula (15)

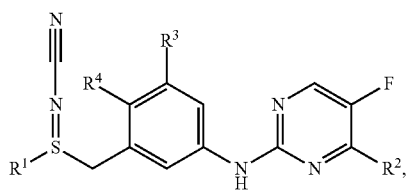

15 in which $R^1$, $R^2$, $R^3$ and $R^4$ are as defined for the compounds of general formula (I) of the present invention according to general formula (I), and the enantiomers, diastereomers, salts, solvates or salts of solvates thereof.

The invention furthermore relates to a method for the preparation of the compounds of formula (I) according to the present invention, in which $R^5$ is a hydrogen atom (identical to the sulfoximines of formula (6))

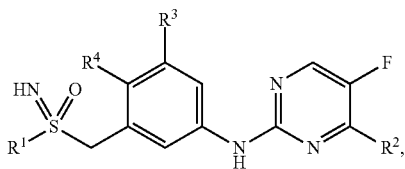

in which method compounds of formula (22)

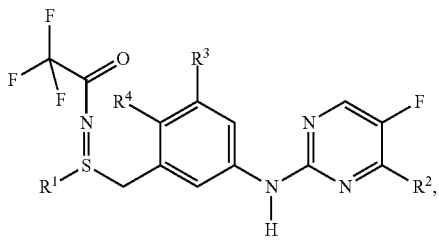

in which $R^1$, $R^2$, $R^3$, and $R^4$ are as defined for the compound of the formula (I) according to the present invention, are oxidised with an alkali salt of permanganic acid in an aliphatic ketone of the formula $C_1$-$C_2$—C(O)—$C_1$-$C_2$-alkyl as a solvent,
followed, if the trifluoroacetyl group present in the compounds of formula (22) has not been cleaved off during abovementioned oxidation process, by the removal of said trifluoroacetyl group by treatment of the resulting intermediate with a suitable base in an alcoholic solvent, to give compounds of the formula (I), in which $R^5$ is hydrogen,
and in which method the resulting compounds (the sulfoximines of formula (6)) are optionally, if appropriate, converted with the corresponding (i) solvents and/or (ii) bases or acids to the solvates, salts and/or solvates of the salts thereof.

The invention furthermore relates to a method for the preparation of the compounds of formula (22) according to the present invention

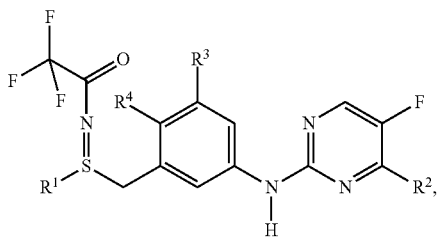

in which method compounds of formula (14)

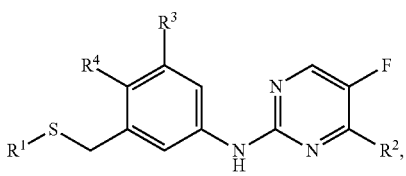

in which $R^1$, $R^2$, $R^3$ and $R^4$ are as defined for the compound of formula (I) according to the present invention, are reacted with trifluoroacetamide in the presence of 1,3-dibromo-5,5-dimethylhydantoin in a cyclic ether as a solvent, thus providing compounds of formula (22) and the resulting compounds are optionally, if appropriate, reacted with the corresponding (i) solvents and/or (ii) bases or acids to the solvates, salts and/or solvates of the salts thereof.

The present invention further concerns compounds of general formula (22)

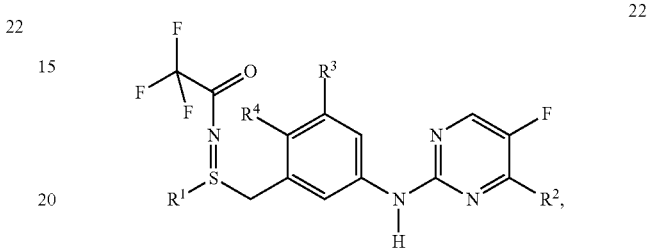

in which $R^1$, $R^2$, $R^3$ and $R^4$ are as defined for the compounds of general formula (I) of the present invention according to general formula (I),
and the enantiomers, diastereomers, salts, solvates or salts of solvates thereof.

The compounds according to the invention show a valuable pharmacological and pharmacokinetic spectrum of action which could not have been predicted.

They are therefore suitable for use as medicaments for the treatment and/or prophylaxis of disorders in humans and animals.

Within the scope of the present invention, the term "treatment" includes prophylaxis.

The pharmaceutical activity of the compounds according to the invention can be explained by their action as inhibitors of CDK9. Thus, the compounds according to the general formula (I) as well as the enantiomers, diastereomers, salts, solvates and salts of solvates thereof are used as inhibitors for CDK9.

Furthermore, the compounds according to the invention show a particularly high potency (demonstrated by a low $IC_{50}$ value in the CDK9/CycT1 assay) for inhibiting CDK9 activity.

In context of the present invention, the $IC_{50}$ value with respect to CDK9 can be determined by the methods described in the method section below. Preferably, it is determined according to Method 1a. ("CDK9/CycT1 kinase assay") described in the Materials and Method section below.

Surprisingly it turned out that the compounds according to the general formula (I) as well as the enantiomers, diastereomers, salts, solvates and salts of solvates thereof selectively inhibit CDK9 in comparison to other cyclin-dependent protein kinases, preferably in comparison to CDK2. Thus, the compounds according to the general formula (I) as well as the enantiomers, diastereomers, salts, solvates and salts of solvates thereof are preferably used as selective inhibitors for CDK9.

Compounds of the present invention according to general formula (I) show a significantly stronger CDK9 than CDK2 inhibition.

In context of the present invention, the $IC_{50}$ value with respect to CDK2 can be determined by the methods described in the method section below. Preferably, it is determined according to Method 2. ("CDK2/CycE kinase assay") described in the Materials and Method section below.

Further, as compared to the CDK9 inhibitors described in the prior art, preferred compounds of the present invention according to general formula (I) show a surprisingly high potency for inhibiting CDK9 activity at high ATP concentrations, which is demonstrated by their low $IC_{50}$ value in the CDK9/CycT1 high ATP kinase assay. Thus, these compounds have a lower probability to be competed out of the ATP-binding pocket of CDK9/CycT1 kinase due to the high intracellular ATP concentration (R. Copeland et al., Nature Reviews Drug Discovery 2006, 5, 730-739). According to this property the compounds of the present invention are particularly able to inhibit CDK9/CycT1 within cells for a longer period of time as compared to classical ATP competitive kinase inhibitors. This increases the anti-tumor cell efficacy at pharmacokinetic clearance-mediated declining serum concentrations of the inhibitor after dosing of a patient or an animal.

In context of the present invention, the $IC_{50}$ value with respect to CDK9 at high ATP concentrations can be determined by the methods described in the method section below. Preferably, it is determined according to Method 1b ("CDK9/CycT1 high ATP kinase assay") as described in the Materials and Method section below.

Further, preferred compounds of the present invention according to formula (I) show an improved anti-proliferative activity in tumor cell lines such as HeLa compared to the CDK9 inhibitors described in the prior art. In context of the present invention, the anti-proliferative activity in tumor cell lines such as HeLa is preferably determined according to Method 3. ("Proliferation Assay") as described in the Materials and Method section below.

Further, preferred compounds of the present invention according to formula (I) show no significant inhibition of carbonic anhydrase-1 or -2 ($IC_{50}$ values of more than 10 µM) and therefore show an improved side effect profile as compared to those CDK inhibitors described in the prior art containing a sulfonamide group, which inhibit carbonic anhydrase-1 or -2. In context of the present invention, the carbonic anhydrase-1 and -2 inhibition is preferably determined according to Method 4. ("Carbonic anhydrase Assay") described in the Materials and Method section below.

Further, preferred compounds of the present invention show high in vitro metabolic stability in rat hepatocytes, and a long terminal half-life upon intravenous administration in rats in vivo, thus featuring a superior pharmacokinetic profile as compared to compounds described in the prior art. In the context of the present invention, the metabolic stability in rat hepatocytes and the terminal half-life in rats upon intravenous administration in vivo is preferably determined according to methods 5 and 6, respectively, described in the Materials and Method section below.

A further subject matter of the present invention is the use of the compounds of general formula (I) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit the activity or expression of CDK9. Therefore, the compounds of formula (I) are expected to be valuable as therapeutic agents. Accordingly, in another embodiment, the present invention provides a method of treating disorders relating to or mediated by CDK9 activity in a patient in need of such treatment, comprising administering to the patient an effective amount of a compound of formula (I) as defined above. In certain embodiments, the disorders relating to CDK9 activity are hyper-proliferative disorders, virally induced infectious diseases and/or of cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity such as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways.

The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ, and canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, salivary gland cancers, anal gland adenocarcinomas, and mast cell tumors.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, non-melanoma skin cancer, and mast cell tumors.

Head-and-neck cancers include, but are not limited to laryngeal, hypopharyngeal, nasopharyngeal, oropharyngeal cancer, lip and oral cavity cancer, squamous cell cancer, and oral melanoma.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma, malignant histiocytosis, fibrosarcoma, hemangiosarcoma, hemangiopericytoma, and leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

The compounds according to general formula (I) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) according to the invention for the treatment and/or prophylaxis of disorders, in particular of the disorders mentioned above. One aspect of the present invention is the use of (rac)-ethyl[(3-{[4-(2,4-difluorophenyl)-5-fluoropyrimidin-2-yl]amino}benzyl)(methyl)oxido-$\lambda^6$-sulfanylidene]carbamate for the treatment and/or prophylaxis of disorders.

A further subject matter of the present invention are the compounds according to the invention for use in a method for the treatment and/or prophylaxis of the disorders mentioned above. One aspect of the present invention is (rac)-ethyl[(3-{[4-(2,4-difluorophenyl)-5-fluoropyrimidin-2-yl]amino}benzyl)(methyl)oxido-$\lambda^6$-sulfanylidene]carbamate for use in a method for the treatment and/or prophylaxis of the disorders mentioned above.

A further subject matter of the present invention is the use of the compounds of general formula (I) according to the invention for the treatment and/or prophylaxis of disorders, in particular lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia.

A preferred subject matter of the present invention are the compounds according to the invention for the use in a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia.

One aspect of the present invention is (rac)-ethyl[(3-{[4-(2,4-difluorophenyl)-5-fluoropyrimidin-2-yl]amino}benzyl)(methyl)oxido-$\lambda^6$-sulfanylidene]carbamate for the use in a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia.

A further subject matter of the present invention is the use of the compounds according to the invention in the manufacture of a medicament for the treatment and/or prophylaxis of disorders, in particular the disorders mentioned above. One aspect of the present invention is the use of (rac)-ethyl[(3-{[4-(2,4-difluorophenyl)-5-fluoropyrimidin-2-yl]amino}benzyl)(methyl)oxido-$\lambda^6$-sulfanylidene]carbamate in the manufacture of a medicament for the treatment and/or prophylaxis of disorders.

A preferred subject matter of the present invention is the use of the compounds according to the invention in the manufacture of a medicament for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia. One aspect of the present invention is the use of (rac)-ethyl[(3-{[4-(2,4-difluorophenyl)-5-fluoropyrimidin-2-yl]amino}benzyl)(methyl)oxido-$\lambda^6$-sulfanylidene]carbamate in the manufacture of a medicament for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia.

A further subject matter of the present invention is a method for the treatment and/or prophylaxis of disorders, in particular the disorders mentioned above, using an effective amount of the compounds according to the invention. One aspect of the present invention is a method for the treatment and/or prophylaxis of disorders, in particular the disorders mentioned above, using an effective amount of (rac)-ethyl[(3-{[4-(2,4-difluorophenyl)-5-fluoropyrimidin-2-yl]amino}benzyl)(methyl)oxido-$\lambda^6$-sulfanylidene]carbamate.

A preferred subject matter of the present invention is a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia, using an effective amount of the compounds according to the invention. One aspect of the present invention is a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia, using an effective amount of (rac)-ethyl[(3-{[4-(2,4-difluorophenyl)-5-fluoropyrimidin-2-yl]amino}benzyl)(methyl)oxido-$\lambda^6$-sulfanylidene]carbamate.

Another aspect of the present invention relates to pharmaceutical combinations comprising a compound of general formula (I) according to the invention in combination with at least one or more further active ingredients.

As used herein the term "pharmaceutical combination" refers to a combination of at least one compound of general formula (I) according to the invention as active ingredient together with at least one other active ingredient with or without further ingredients, carrier, diluents and/or solvents.

Another aspect of the present invention relates to pharmaceutical compositions comprising a compound of general formula (I) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Compounds of formula (I) may be administered as the sole pharmaceutical agent or in combination with one or more additional therapeutic agents where the combination causes no unacceptable adverse effects. This pharmaceutical combination includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

- Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;
- Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;
- Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and epristeride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;
- Plant-derived anti-tumor substances include, e.g., those selected from mitotic inhibitors, for example epothilones such as sagopilone, ixabepilone and epothilone B, vinblastine, vinflunine, docetaxel, and paclitaxel;
- Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;
- Immunologicals include interferons such as interferon alpha, interferon alpha-2a, interferon alpha-2b, interferon beta, interferon gamma-1a and interferon gamma-nl, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; Merial melanoma vaccine
- Biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, ProMune, and ubenimex;
- Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;
- Antibodies include, but are not limited to, trastuzumab, cetuximab, bevacizumab, rituximab, ticilimumab, ipilimumab, lumiliximab, catumaxomab, atacicept, oregovomab, and alemtuzumab;
- VEGF inhibitors such as, e.g., sorafenib, DAST, bevacizumab, sunitinib, recentin, axitinib, aflibercept, telatinib, brivanib alaninate, vatalanib, pazopanib, and ranibizumab; Palladia
- EGFR (HER1) inhibitors such as, e.g., cetuximab, panitumumab, vectibix, gefitinib, erlotinib, and Zactima;
- HER2 inhibitors such as, e.g., lapatinib, tratuzumab, and pertuzumab;
- mTOR inhibitors such as, e.g., temsirolimus, sirolimus/Rapamycin, and everolimus;
- c-Met inhibitors;
- PI3K and AKT inhibitors;
- CDK inhibitors such as roscovitine and flavopiridol;
- Spindle assembly checkpoints inhibitors and targeted anti-mitotic agents such as PLK inhibitors, Aurora inhibitors (e.g. Hesperadin), checkpoint kinase inhibitors, and KSP inhibitors;
- HDAC inhibitors such as, e.g., panobinostat, vorinostat, MS275, belinostat, and LBH589;
- HSP90 and HSP70 inhibitors;
- Proteasome inhibitors such as bortezomib and carfilzomib;
- Serine/threonine kinase inhibitors including MEK inhibitors (such as e.g. RDEA 119) and Raf inhibitors such as sorafenib;
- Farnesyl transferase inhibitors such as, e.g., tipifarnib;
- Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors; Palladia, masitinib
- Vitamin D receptor agonists;
- Bcl-2 protein inhibitors such as obatoclax, oblimersen sodium, and gossypol;

Cluster of differentiation 20 receptor antagonists such as, e.g., rituximab;
Ribonucleotide reductase inhibitors such as, e.g., gemcitabine;
Tumor necrosis apoptosis inducing ligand receptor 1 agonists such as, e.g., mapatumumab;
5-Hydroxytryptamine receptor antagonists such as, e.g., rEV598, xaliprode, palonosetron hydrochloride, granisetron, Zindol, and AB-1001;
Integrin inhibitors including alpha5-beta1 integrin inhibitors such as, e.g., E7820, JSM 6425, volociximab, and endostatin;
Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;
Aromatase inhibitors such as, e.g., anastrozole, letrozole, testolactone, exemestane, amino-glutethimide, and formestane;
Matrix metalloproteinase inhibitors;
Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

The compounds of the present invention may also be employed in cancer treatment in conjunction with radiation therapy and/or surgical intervention.

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Furthermore, the compounds of formula (I) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds of the invention of general formula (I) and/or the pharmaceutical composition of the present invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological assays one or more times. When tested more than once, data are reported as either average values or as median values, wherein
  the average value, also referred to as the arithmetic mean value, represents the sum of the values obtained divided by the number of times tested, and
  the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro pharmacological properties of the compounds can be determined according to the following assays and methods.

1a. CDK9/CycT1 Kinase Assay:

CDK9/CycT1-inhibitory activity of compounds of the present invention was quantified employing the CDK9/CycT1 TR-FRET assay as described in the following paragraphs:

Recombinant full-length His-tagged human CDK9 and CycT1, expressed in insect cells and purified by Ni-NTA affinity chromatography, were purchased from Invitrogen (Cat. No PV4131). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 µg/ml. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

1b. CDK9/CycT1 High ATP Kinase Assay

CDK9/CycT1-inhibitory activity of compounds of the present invention at a high ATP concentration after preincubation of enzyme and test compounds was quantified employing the CDK9/CycT1 TR-FRET assay as described in the following paragraphs.

Recombinant full-length His-tagged human CDK9 and CycT1, expressed in insect cells and purified by Ni-NTA affinity chromatography, were purchase from Invitrogen (Cat. No PV4131). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 0.5 µg/ml. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

2. CDK2/CycE Kinase Assay:

CDK2/CycE-inhibitory activity of compounds of the present invention was quantified employing the CDK2/CycE TR-FRET assay as described in the following paragraphs:

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.25 µM=>final conc. in the 5 µl assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/ml. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

3. Proliferation Assay:

Cultivated tumour cells (HeLa, human cervical tumour cells, ATCC CCL-2; NCI-H460, human non-small cell lung carcinoma cells, ATCC HTB-177; A2780, human ovarian carcinoma cells, ECACC #93112519; DU 145, hormone-independent human prostate carcinoma cells, ATCC HTB-81; HeLa-MaTu-ADR, multidrug-resistant human cervical carcinoma cells, EPO-GmbH Berlin; Caco-2, human colorectal carcinoma cells, ATCC HTB-37; B16F10, mouse melanoma cells, ATCC CRL-6475) were plated at a density of 5,000 cells/well (DU145, HeLa-MaTu-ADR), 3,000 cells/well (NCI-H460, HeLa), 2,500 cells/well (A2780), 1,500 cells/well (Caco-2), or 1,000 cells/well (B16F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.001-10 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The $IC_{50}$ values (inhibitory concentration at 50% of maximal effect) were determined by means of a 4 parameter fit.

Non-adherent MOLM-13 human acute myeloid leukemia cells (DSMZ ACC 554) were seeded at a density of 5,000 cells/well in a 96-well multititer plate in 100 µL of growth medium supplemented 10% fetal calf serum. After 24 hours, cell viability of one plate (zero-point plate) was determined with the Cell Titre-Glo Luminescent Cell Viability Assay (Promega), while 50 µL of test compound containing medium was added to the wells of the other plates (final concentrations in the range of 0.001-10 µM and DMSO controls; the final concentration of the solvent dimethyl sulfoxide was 0.5%). Cell viability was assessed after 72-hour exposure with the Cell Titre-Glo Luminescent Cell Viability Assay (Promega). $IC_{50}$ values (inhibitory concentration at 50% of maximal effect) were determined by means of a 4 parameter fit on measurement data which were normalized to vehicle (DMSO) treated cells (=100%) and measurement readings taken immediately before compound exposure (=0%).

4. Carbonic Anhydrase Assay

The principle of the assay is based on the hydrolysis of 4-nitrophenyl acetate by carbonic anhydrases (Pocker & Stone, Biochemistry, 1967, 6, 668), with subsequent photometric determination of the dye product 4-nitrophenolate at 400 nm by means of a 96-channel spectral photometer.

2 µL of the test compounds, dissolved in DMSO (100-fold final concentration), in a concentration range of 0.03-10 µmol/L (final), was pipetted as quadruplicates into the wells of a 96-hole microtiter plate. Wells that contained the solvent without test compounds were used as reference values (1. Wells without carbonic anhydrase for correction of the non-enzymatic hydrolysis of the substrate, and 2. Wells with carbonic anhydrase for determining the activity of the non-inhibited enzyme).

188 µL of assay buffer (10 mmol/L of Tris/HCl, pH 7.4, 80 mmol/L of NaCl), with or without 3 units/well of carbonic anhydrase-1 [=human carbonic anhydrase-1 (Sigma, #C4396)] in order to determine carbonic anhydrase-1 inhibition or 3 units/well of carbonic anhydrase-2 [=human carbonic anhydrase-2 (Sigma, #C6165)] for measuring carbonic anhydrase-2 inhibition, was pipetted into the wells of the microtiter plate. The enzymatic reaction was started by the addition of 10 microL of the substrate solution (1 mmol/L of 4-nitrophenyl acetate (Fluka #4602), dissolved in anhydrous acetonitrile (final substrate concentration: 50 µmol/L). The plate was incubated at room temperature for 15 minutes. Absorption was measured by photometry at a wavelength of 400 nm. The enzyme inhibition was calculated after the measured values were normalized to the absorption of the reactions in the wells without enzyme (=100% inhibition) and to the absorption of reactions in the wells with non-inhibited enzyme (=0% inhibition). $IC_{50}$ values were determined by means of a 4 parameter fit using the company's own software.

5. Investigation of In Vitro Metabolic Stability in Rat Hepatocytes

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold Williams medium E (purchased from Sigma Aldrich Life Science, St Louis, Mo.). The resulting cell suspension was filtered through sterile gaze in 50 ml falcon tubes and centrifuged at 50×g for 3 min at room temperature. The cell pellet was resuspended in 30 ml WME and centrifuged through a Percoll® gradient for 2 times at 100×g. The hepatocytes were washed again with Williams' medium E (WMA) and resuspended in medium containing 5% Fetal calf serum (FCS, purchased from Invitrogen, Auckland, NZ). Cell viability was determined by trypan blue exclusion.

For the metabolic stability assay liver cells were distributed in WME containing 5% FCS to glass vials at a density of $1.0×10^6$ vital cells/ml. The test compound was added to a final concentration of 1 µM. During incubation, the hepatocyte suspensions were continuously shaken and aliquots were taken at 2, 8, 16, 30, 45 and 90 min, to which equal volumes of cold acetonitrile were immediately added. Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The maximal oral bioavailability (Fmax) was calculated using the following scaling parameters: Liver blood flow (rat)—4.2 L/h/kg; specific liver weight—32 g/kg rat body weight; liver cells in vivo— $1.1×10^8$ cells/g liver, liver cells in vitro—$0.5×10^6$/ml.

6. In Vivo Pharmacokinetics in Rats

For in vivo pharmacokinetic experiments test compounds were administered to male Wistar rats intravenously at doses of 0.3 to 1 mg/kg formulated as solutions using either rat plasma or solubilizers such as PEG400 in well-tolerated amounts.

For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparin tubes (Monovetten®, Sarstedt) and centrifuged for 15 min at 3000 rpm. An aliquot of 100 µL from the supernatant (plasma) was taken and precipitated by addition of 400 µL icecold acetonitril and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood, AUCnorm: Area under the concentration-time curve from t=0 h to infinity (extrapolated) divided by the administered dose (in kg*h/L); t½: terminal half-life (in h).

PREPARATIVE EXAMPLES

Syntheses of Compounds

The syntheses of the compounds of the present invention can preferably be carried out according to Schemes 1-6 below.

In addition to said routes described below, also other routes may be used to synthesise the target compounds, in accordance with common general knowledge of a person skilled in the art of organic synthesis. The order of transformations exemplified in the following Schemes is therefore not intended to be limiting, and suitable synthesis steps from various schemes can be combined to form additional synthesis sequences. In addition, interconversion of any of the substituents $R^1$, $R^2$, $R^3$, $R^4$ and/or $R^5$ can be achieved before and/or after the exemplified transformations. These modifications can be such as the introduction of protective groups, cleavage of protective groups, reduction or oxidation of functional groups, halogenation, metallation, metal catalysed coupling reactions, substitution or other reactions known to a person skilled in the art. These transformations include those which introduce a functionality allowing for further interconversion of substituents. Appropriate protective groups and their introduction and cleavage are well-known to a person skilled in the art (see for example T. W. Greene and P. G. M. Wuts in Protective Groups in Organic Synthesis, 3$^{rd}$ edition, Wiley 1999). Specific examples are described in the subsequent paragraphs. Further, it is possible that two or more successive steps may be performed without work-up being performed between said steps, e.g. a "one-pot" reaction, as it is well-known to a person skilled in the art.

The geometry of the sulfoximine moiety renders the compounds of the general formula (I), including its sub-compartments (5), (6) and (16), chiral. Separation of racemic sulfoximines into their enantiomers can be achieved by methods known to the person skilled in the art, preferably by means of preparative HPLC on chiral stationary phase.

Scheme 1, wherein $R^1$, $R^2$, $R^3$, $R^4$ and $R^5$ are as defined for the compound of general formula (I) according to the present invention, outlines the preparation of compounds of the general formula (I) from 2,4-dichloro-5-fluoropyrimidine (CAS #2927-71-1, 1). Said starting material (1) is reacted with a boronic acid derivative of formula (2) to give a compound of formula (3). The boronic acid derivative (2) may be a boronic acid (R=—H) or an ester of the boronic acid, e.g. its isopropyl ester (R=—CH(CH$_3$)$_2$), preferably an ester derived from pinacol in which the boronic acid intermediate forms a 2-aryl-4,4,5,5-tetramethyl-1,3,2-dioxaborolane (R—R=—C(CH$_3$)$_2$—C(CH$_3$)$_2$—). Boronic acids and their esters are commercially available and well-known to the person skilled in the art; see e.g. D. G. Hall, Boronic Acids, 2005 WILEY-VCH Verlag GmbH & Co. KGaA, Weinheim, ISBN 3-527-30991-8 and references cited therein.

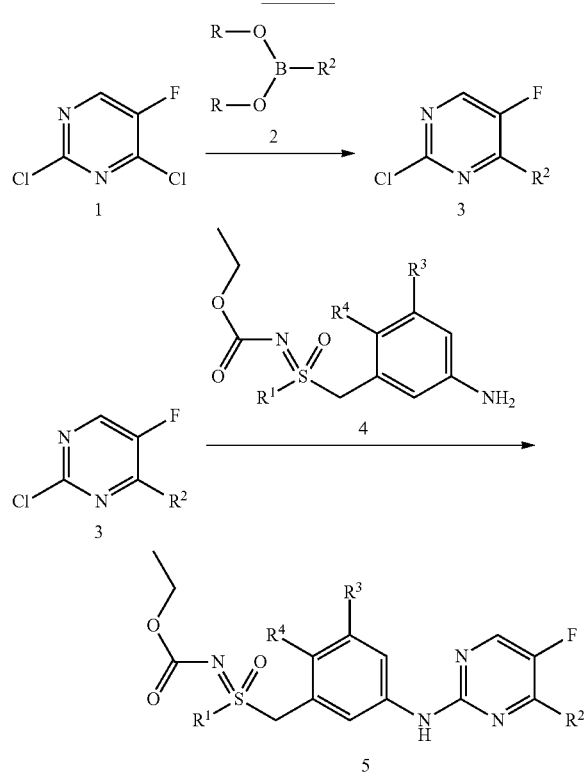

Scheme 1

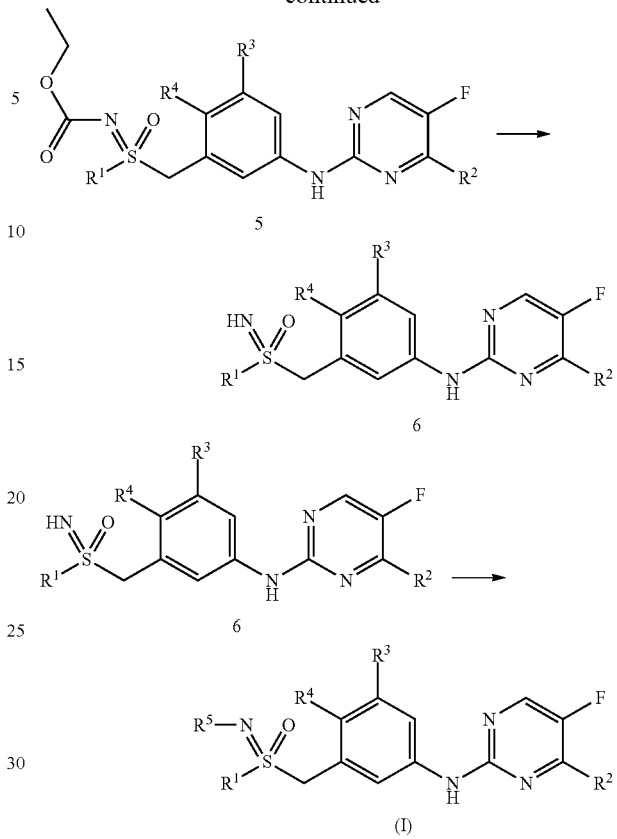

The coupling reaction is catalyzed by Pd catalysts, e.g. by Pd(0) catalysts like tetrakis(triphenylphosphine)palladium (0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride [Pd(dppf)Cl$_2$].

The reaction is preferably carried out in a mixture of a solvent like 1,2-dimethoxyethane, dioxane, DMF, DME, THF, or isopropanol with water and in the presence of a base like aqueous potassium carbonate, aqueous sodium bicarbonate or potassium phosphate.

The reaction is performed at temperatures ranging from room temperature (=20° C.) to the boiling point of the solvent. Further on, the reaction can be performed at temperatures above the boiling point using pressure tubes and a microwave oven. (review: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

In the second step, a compound of formula (3) is reacted with a suitable aniline of formula (4) to give the corresponding cross-coupling product of formula (5). The compounds of formula (5) can be prepared by Palladium-catalyzed C—N cross-coupling reactions (for a review on C—N cross-coupling reactions see for example: a) L. Jiang, S. L. Buchwald in 'Metal-Catalyzed Cross-Coupling Reactions', 2$^{nd}$ ed.: A. de Meijere, F. Diederich, Eds.: Wiley-VCH: Weinheim, Germany, 2004).

Preferred is the use of suitable palladium precatalysts based upon biarylmonphosphines that are easily activated and ensure the formation of the active mono-ligated Pd(0)

complex (see for examples a) S. L. Buchwald et al, J. Am. Chem. Soc. 2008, 130, 6686; b) S. L. Buchwald et al, J. Am. Chem. Soc. 2008, 130, 13552). The reactions are run in the presence of a weak base at elevated temperatures (see for example: a) S. L: Buchwald et al, Tet. Lett. 2009, 50, 3672). Most preferred is the herein described use of chloro(2-dicyclohexylphosphino-2',4',6'-tri-iso-propy 1,1'-biphenyl) [2-(2-aminoethyl)phenyl]palladium(II) methyl-tert-butylether adduct, 2-dicyclohexylphosphino-2',4',6'-triisopropyl-biphenyl and potassium phosphate in toluene and 1-methylpyrrolidin-2-one. The reactions are preferably run under an atmosphere of argon for 3 hours at 130° C. in a microwave oven or in an oil bath.

Deprotection of compounds of formula (5), which constitutes a sub-compartment of general formula (I), gives the corresponding N-unprotected sulfoximines of formula (6), constituting a sub-compartment of formula (I) as well. The deprotection is preferably carried out with sodium ethanolate in ethanol at 60° C. (see for example: U. Lücking et al, WO2005/37800).

N-unprotected sulfoximines of formula (6) may be reacted to give N-functionalized derivatives of formula (I). There are multiple methods for the preparation of N-functionalized sulfoximines by functionalization of the nitrogen of the sulfoximine group:

Alkylation: see for example: a) U. Lücking et al, US 2007/0232632; b) C. R. Johnson, J. Org. Chem. 1993, 58, 1922; c) C. Bolm et al, Synthesis 2009, 10, 1601.

Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.

Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C. Bolm et al, J. Org. Chem. 2005, 70, 2346; e) U. Lücking et al, WO2007/71455.

Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.

Reaction with sulfonylchlorides: see for example: a) D. J. Cram et al, J. Am. Chem. Soc. 1970, 92, 7369; b) C. R. Johnson et al, J. Org. Chem. 1978, 43, 4136; c) A. C. Barnes, J. Med. Chem. 1979, 22, 418; d) D. Craig et al, Tet. 1995, 51, 6071; e) U. Lücking et al, US2007/191393.

Reaction with chloroformiates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800.

Anilines of formula (4) can be prepared as described in scheme 2, wherein $R^1$, $R^3$ and $R^4$ are as defined for the compound of general formula (I) according to the present invention, and wherein LG represents a leaving group, preferably chloro or bromo:

Scheme 2

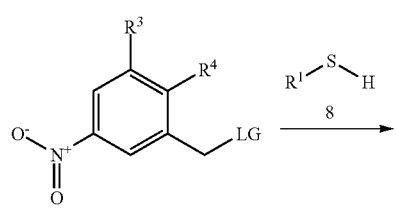

7

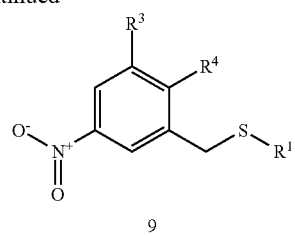

9

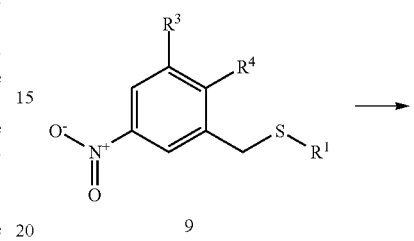

9

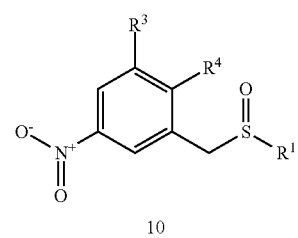

10

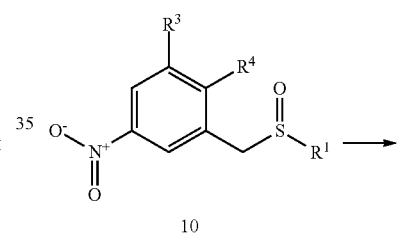

10

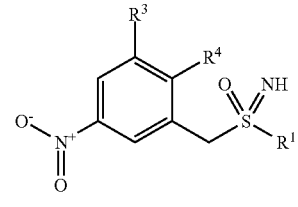

11

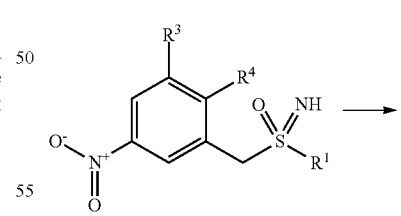

11

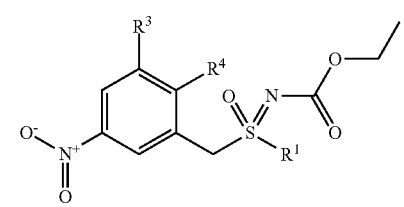

12

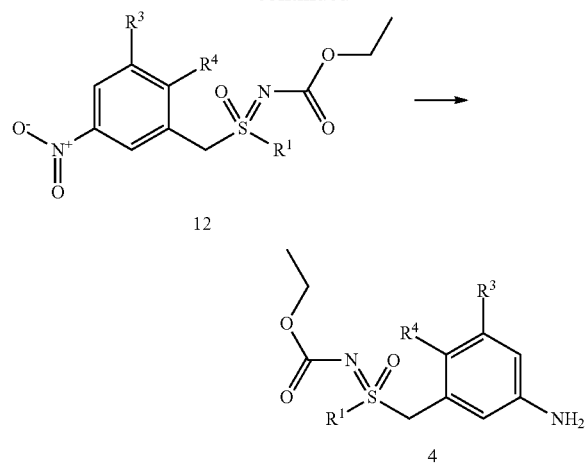

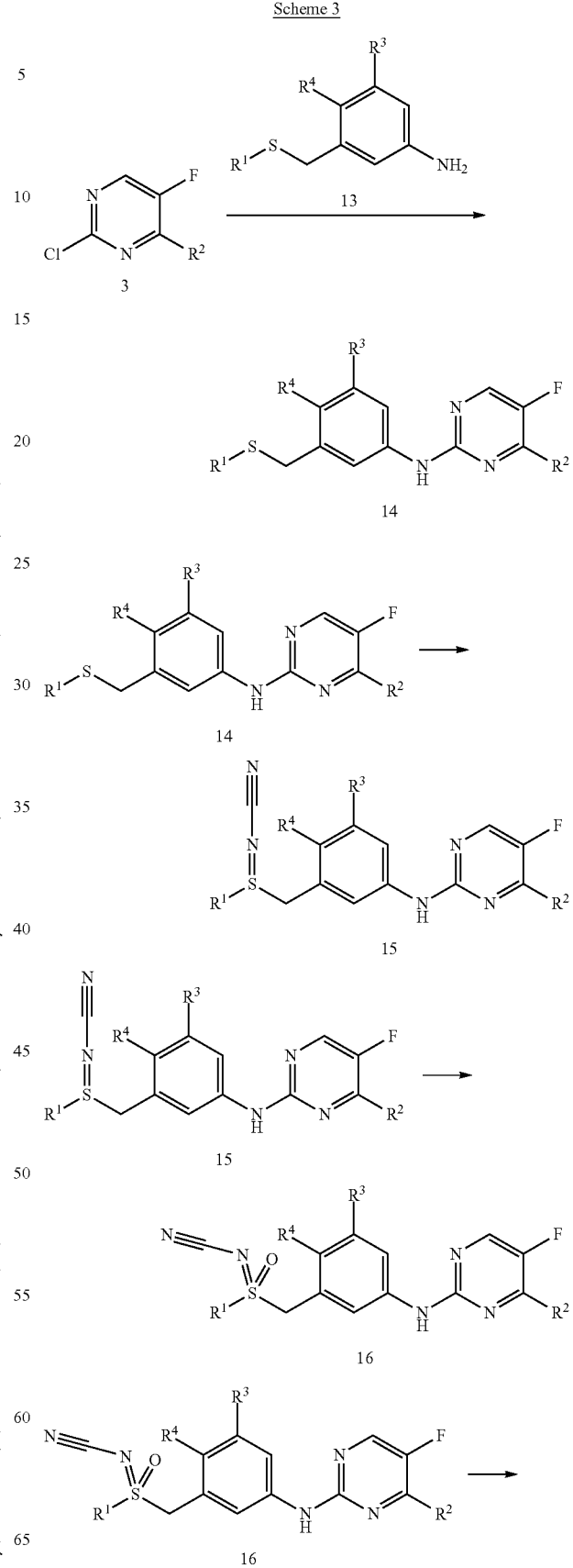

Reaction of suitable compounds of formula (7) with suitable thiols of formula (8) under basic conditions yields the corresponding thioethers of formula (9) (see for example: Sammond et al, Bioorg. Med. Chem. Lett. 2005, 15, 3519). Starting materials of formulas (7) and (8) are commercially available in broad variety, or can be prepared by methods known to the person skilled in the art (e.g. from the corresponding benzylic alcohols for compounds of formula (7)).

Oxidation of thioethers of formula (9) gives the corresponding sulfoxides of formula (10). The oxidation can be performed analogously to known processes (see for example: (a) M. H. Ali et al, Synthesis 1997, 764; (b) M. C. Carreno, Chem. Rev. 1995, 95, 1717; (c) I. Patel et al, Org. Proc. Res. Dev. 2002, 6, 225; (d) N. Khiar et al, Chem. Rev. 2003, 103, 3651). Preferred is the herein described use of periodic acid und iron(III)chloride.

Rhodium-catalyzed imination of the sulfoxides of formula (10) followed by deprotection gives the corresponding N-unprotected sulfoximines of formula (11) (see for example: Bolm et al, Org. Lett. 2004, 6, 1305).

Introduction of a suitable protecting group leads to N-protected sulfoximines, such as compounds of formula (12) (see for example: Lücking et al, WO 2005/037800).

Reduction of the nitro group finally gives the desired anilines of formula (4). The reduction can be prepared analogously to known processes (see for example: (a) Sammond et al; Bioorg. Med. Chem. Lett. 2005, 15, 3519; (b) R. C. Larock, Comprehensive Organic Transformations, VCH, New York, 1989, 411-415).

An alternative synthesis approach to compounds of general formula (I) according to the present invention is shown in Scheme 3 wherein $R^1$, $R^2$, $R^3$, $R^4$ and $R^5$ are as defined for the compound of general formula (I) according to the present invention.

In the first step a compound of formula (3) is reacted with a suitable aniline of formula (13) to give a compound of formula (14).

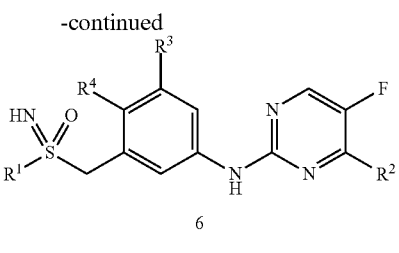

This coupling reaction can be carried out in an alcohol like 1-butanol or in an inert solvent like DMF, THF, DME, dioxane or mixtures of such solvents in the presence of an acid like hydrogen chloride or 4-methylbenzenesulfonic acid. Preferably, the reaction is carried out at an elevated temperature, for example 140° C.

Alternatively, Palladium-catalyzed C—N cross-coupling reactions as described above in context of Scheme 1 can be employed.

In the second step, a compound of formula (14) is reacted with cyanamide, or sodium hyrogencyanamide, as a nitrogen source to give the corresponding N-cyanosulfilimine of formula (15).

The reaction can be carried out using NBS and potassium tert-butoxide in methanol at room temperature (see for example: a) C. Bolm et al, Org. Lett. 2007, 9, 3809). Instead of NBS, iodine or iodobenzene diacetate (PhI(OAc)$_2$) can be employed (see for example: a) C. Bolm et al, Org. Lett. 2007, 9, 3809; b) C. Bolm et al, Bioorg. Med. Chem. Lett. 2011, 21, 4888; c) J. M. Babcock, US 2009/0023782). Particularly preferred is the herein described use of iodobenzene diacetate and a halogenated aliphatic hydrocarbon, preferably DCM, as a solvent. An also particularly preferred alternative method is the herein described use of sodium hydrogencyanamide as a nitrogen source and 1,3-dibromo-5,5-dimethylhydantoin in an aliphatic alcohol $C_1$-$C_4$-alkyl-OH, preferably methanol.

Finally, the N-cyanosulfilimine of formula (15) is oxidized to the corresponding N-cyanosulfoximine of formula (16), constituting another sub-compartment of formula (I) in which $R^5$ is cyano. There are multiple methods for the oxidation of N-cyanosulfilimines of formula (15) to N-cyanosulfoximines of formula (16) (see for example: a) C. Bolm et al, Org. Lett. 2007, 9, 3809; b) J. E. G. Kemp et al, Tet. Lett. 1979, 39, 3785; c) M. R. Loso et al, US patent application US2007/0203191; d) J. M. Babcock, US patent application US2009/0023782; e) C. Bolm et al, Adv. Synth. Catal. 2010, 352, 309). The reaction can be performed using an alkali salt of permanganic acid in an aliphatic ketone of the formula $C_1$-$C_2$-alkyl-C(=O)—$C_1$-$C_2$-alkyl. Most preferred is the herein described use of potassium permanganate in acetone.

N-cyanosulfoximines of formula (16) can be converted to the corresponding N-unprotected sulfoximines of formula (6). The reaction is preferably carried out using trifluoroacetic anhydride (TFAA) in DCM followed by the reaction with potassium carbonate in methanol (see for example: a) C. Bolm et al, Org. Lett. 2007, 9, 3809).

Anilines of formula (13) can be prepared as described in scheme 4, wherein $R^1$, $R^3$ and $R^4$ are as defined for the compound of general formula (I) according to the present invention:

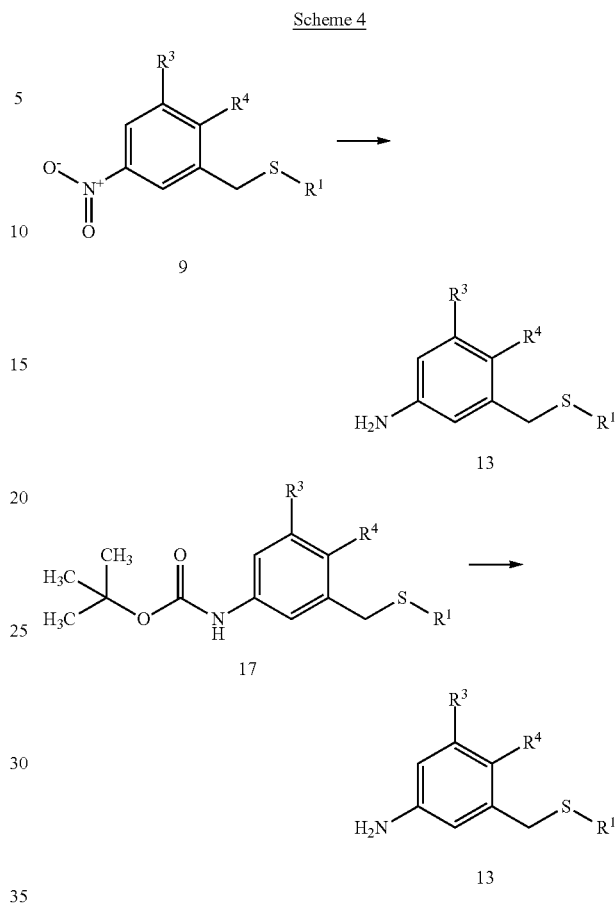

Reduction of the nitro group of a compound of formula (9), which can be prepared as shown in Scheme 2, gives the desired anilines of formula (13). The reduction can be performed analogously to known processes (see for example: (a) Sammond et al; Bioorg. Med. Chem. Lett. 2005, 15, 3519; (b) R. C. Larock, Comprehensive Organic Transformations, VCH, New York, 1989, 411-415). Alternatively, appropriately N-protected precursors can be employed such as the respective tert-butoxy carbonyl (Boc) derivatives of formula (17). Protective groups for amino groups present in analogues and methods for their introduction and removal are well known to the person skilled in the art, see e.g. T. W. Greene and P. G. M. Wuts in: Protective Groups in Organic Synthesis, 3$^{rd}$ edition, Wiley (1999). More specifically, Boc protecting groups as in compounds of formula (17) are readily removed by exposure to acidic reagents, such as trifluoroacetic acid or hydrogen chloride, in a suitable solvent, such as dichloromethane or 1,4-dioxane, respectively. The thioether moiety present in compounds of the formula (17) can be e.g. introduced in analogy to the method outlined in Scheme 2.

An alternative synthesis approach to compounds of general formula (14) is shown in Scheme 5 wherein $R^1$, $R^2$, $R^3$, $R^4$ and $R^5$ are as defined for the compound of general formula (I) according to the present invention. The compounds of general formula (14) can be converted to compounds of formulae (16) and (6), which constitute sub-compartments of general formula (I) according to the present invention, using the methodology that is described in scheme 3.

Scheme 5

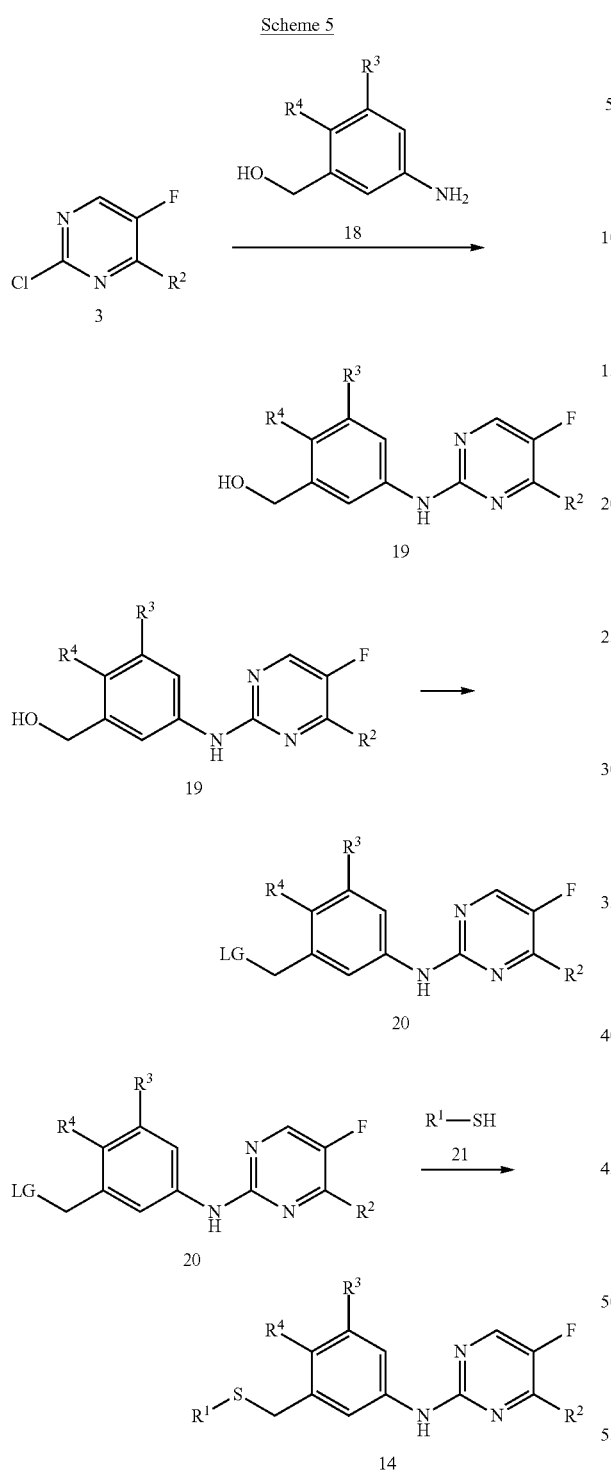

In the first step a compound of formula (3) is reacted with a suitable aniline of formula (18) to give a compound of formula (19).

This coupling reaction can be carried out in an alcohol like 1-butanol or in an inert solvent like DMF, THF, DME, dioxane or mixtures of such solvents in the presence of an acid like hydrogen chloride or 4-methylbenzenesulfonic acid. Preferably, the reaction is carried out at an elevated temperature, for example 140° C.

Alternatively, Palladium-catalyzed C—N cross-coupling reactions as described above in context of Scheme 1 can be employed.

In the second step, a compound of formula (19), in which $R^2$, $R^3$ and $R^4$ are as defined for the compound of general formula (I), is converted to a compound of formula (20), in which $R^2$, $R^3$ and $R^4$ are as defined for the compound of general formula (I) and in which LG represents a leaving group, preferably chloro or bromo. Preferred is the herein described use of thionylchloride in NMP or DMF and DCM for the formation of benzylchloride derivatives (LG=Cl). A possibility for the formation of benzylbromide derivatives (LG=Br) is the use of tetrabromomethane and triphenylphosphane in DCM (see for example: Polla et al, Bioorganic and Medicinal Chemistry, 2004, 12, 1151).

In the third step, a compound of formula (20) is converted to a thioether of formula (14), in which $R^1$, $R^2$, $R^3$ and $R^4$ are as defined for the compound of general formula (I), by reaction with suitable thiols of formula (21), in which $R^1$ is as defined for the compound of formula (I), under basic conditions, yielding the corresponding thioethers of formula (14) (see for example: Sammond et al, Bioorg. Med. Chem. Lett. 2005, 15, 3519). Thiols of formula (21), and likewise anilines of formula (18), are known to the person skilled in the art and are commercially available in considerable variety.

A further alternative synthesis to compounds of general formula (I) according to the present invention is shown in Scheme 6 wherein $R^1$, $R^2$, $R^3$, $R^4$ and $R^5$ are as defined for the compound of general formula (I) according to the present invention.

Scheme 6

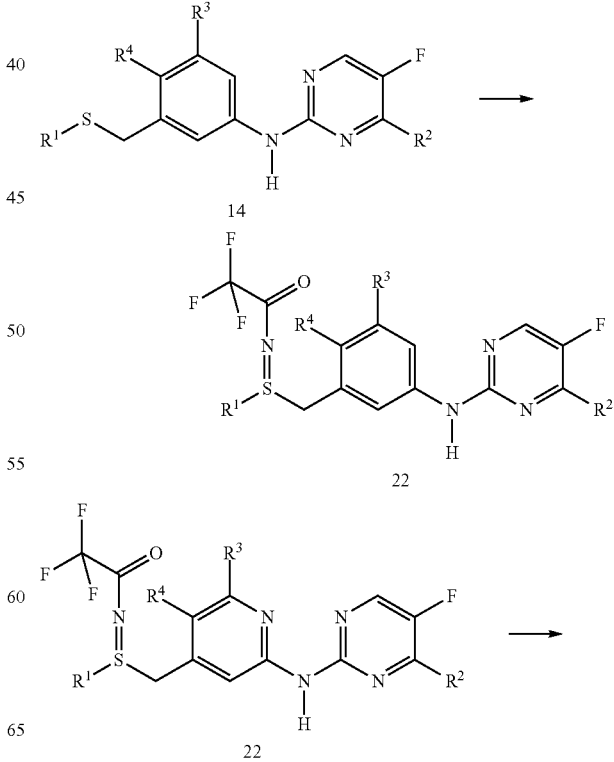

-continued

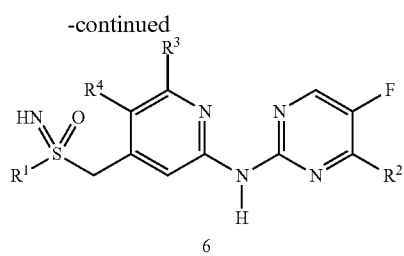

In the first step, imination of a compound of formula (14) gives the corresponding sulfilimine of formula (22) (see for examples: a) C. Bolm et al, Organic Letters, 2004, 6, 1305; b) J. Krüger et al, WO 2012/038411). Said imination is preferably performed by reacting a compound of the formula (14) with trifluoroacetamide and a suitable oxidant, such as 1,3-dibromo-5,5-dimethylhydantoin, in the presence of a base, such as sodium tert.-butoxide, in a cyclic ether such as tetrahydrofuran or dioxane, or mixtures thereof.

Oxidation of the sulfilimine of formula (22) followed by deprotection of the trifluoroacetyl group gives the N-unprotected sulfoximine of formula (I) ($R^5$=H) (see for examples: a) A. Plant et al, WO 2006/037945; b) J. Krüger et al, WO 2012/038411). Said oxidation is preferably performed by reacting compounds of formula (22) with an alkali salt of permanganic acid in an aliphatic ketone of the formula $C_1$-$C_2$-alkyl-C(=O)—$C_1$-$C_2$-alkyl. Most preferred is the herein described use of potassium permanganate in acetone. Unless the trifluoroacetyl group present in the compounds of formula (22) has been cleaved off during the abovementioned oxidation process, it can be removed by treatment of the resulting intermediate with a suitable base, such as a carbonate of an alkali or earth alkali metal, preferably potassium carbonate, in a suitable alcohol, such as an aliphatic alcohol of the formula $C_1$-$C_6$-alkyl-OH, preferably methanol. Alternatively, the oxidation can be performed by reacting compounds of formula (17) with a peroxomonosulfate based oxidant, such as Oxone® (CAS No. 37222-66-5), in a suitable solvent mixture, such as methanol/water and as the circumstances require additional DMF, while controlling the pH of the reaction mixture with aqueous potassium hydroxide solution. Said methods both result in the formation of N-unprotected sulfoximines of formula (6), which constitutes a sub-compartment of the general formula (I) ($R^5$=H).

Preparation of Compounds:

ABBREVIATIONS USED IN THE DESCRIPTION OF THE CHEMISTRY AND IN THE EXAMPLES THAT FOLLOW ARE approx. (approximately); br (broad); $CDCl_3$ (deuterated chloroform); cHex (cyclohexane); d (doublet); dd (doublet of doublets); ddd (doublet of doublets of doublets); DCM (dichloromethane); DME (1,2-dimethoxyethane); DIPEA (di-iso-propylethylamine); DMF (dimethylformamide); DMSO (dimethyl sulfoxide); eq (equivalent); ES (electrospray); EtOAc (ethyl acetate); EtOH (ethanol); iPrOH (iso-propanol); mCPBA (meta-chloroperoxybenzoic acid); MeCN (acetonitrile), MeOH (methanol); MS (mass spectrometry); NBS (N-bromosuccinimide), NMR (nuclear magnetic resonance); p (pentet); $Pd(dppf)Cl_2$ ([1,1'-bis(diphenylphosphino)ferrocene]dichloro palladium(II) complex with dichloromethane); iPrOH (iso-propanol); q (quartet); RT (room temperature); s (singlet); sat. aq. (saturated aqueous); $SiO_2$ (silica gel); TFA (trifluoroacetic acid); TFAA (trifluoroacetic anhydride), THF (tetrahydrofuran); trd (triplet of doublets); tr (triplet).

The IUPAC names of the examples were generated using the program 'ACD/Name batch version 12.01' from ACD LABS.

Example 1

(rac)-{[3-{[4-(2,4-Difluorophenyl)-5-fluoropyrimidin-2-yl]amino}-5-(trifluoromethyl)benzyl](methyl) oxido-$\lambda^6$-sulfanylidene}cyanamide

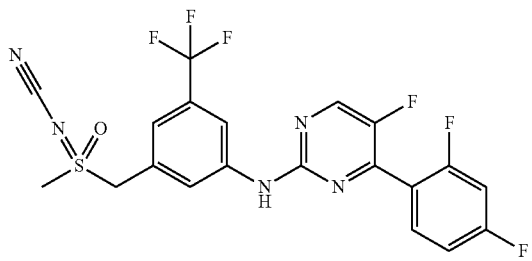 [SMILES: CS(=O)(Cc1cc(Nc2ncc(F)c(-c3ccc(F)cc3F)n2)cc(C(F)(F)F)c1)=NC#N]

Preparation of Intermediate 1.1:

2-Chloro-4-(2,4-difluorophenyl)-5-fluoropyrimidine

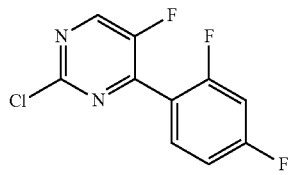 [SMILES: Fc1ccc(-c2nc(Cl)ncc2F)c(F)c1]

Under an atmosphere of argon, a mixture of 2,4-dichloro-5-fluoropyrimidine (19.3 g; 115.5 mmol, Aldrich Chemical Company Inc.), (2,4-difluorophenyl)boronic acid (20.0 g; 127.0 mmol; Aldrich Chemical Company Inc.) and [1,1'-bis (diphenylphosphino)ferrocene]dichloropalladium(II) (9.4 g; 11.5 mmol; Aldrich Chemical Company Inc.) in a 2M aqueous solution of potassium carbonate (173 mL) and 1,2-dimethoxyethane (496 mL) was stirred for 90 minutes at 90° C. After cooling, the batch was diluted with ethyl acetate and washed with diluted aqueous sodium chloride solution. The organic phase was filtered using a Whatman filter and concentrated. The residue was first purified by chromatography (hexane/ethyl acetate 20% to 50%) and then digested with hexane to give the desired product (15.0 g; 61.2 mmol).

$^1$H NMR (400 MHz, $CDCl_3$, 300K) δ=8.56 (m, 1H), 7.73 (m, 1H), 7.07 (m, 1H), 6.95 (m, 1H).

Preparation of Intermediate 1.2:

tert-Butyl {3-[(methylsulfanyl)methyl]-5-(trifluoromethyl)phenyl}carbamate

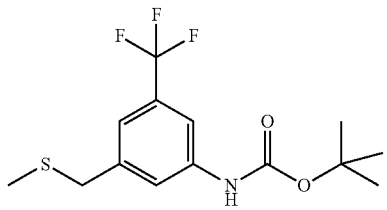 [SMILES: CSCc1cc(NC(=O)OC(C)(C)C)cc(C(F)(F)F)c1]

Sodium methanethiolate (2.32 g; 30.0 mmol) was added in two portions to a stirred solution of tert-butyl [3-(chloromethyl)-5-(trifluoromethyl)phenyl]carbamate (9.7 g; 30.0 mmol; Enamine) in ethanol (185 mL) at −40° C. The cooling bath was removed and the batch was stirred at room temperature for 2 hours. Additional sodium methanethiolate (0.46 g; 5.9 mmol) was added and the mixture was stirred for 2 hours at room temperature. The batch was diluted with saturated aqueous sodium chloride solution and extracted with ethyl acetate (2×). The combined organic phases were washed with water, dried (sodium sulfate), filtered and concentrated to give the desired product (10.0 g) that was used without further purification.

$^1$H NMR (400 MHz, CDCl$_3$, 300K) δ=7.57 (s, 1H), 7.51 (s, 1H), 7.23 (s, 1H), 6.59 (s, 1H), 3.67 (s, 2H), 2.00 (s, 3H), 1.53 (s, 9H).

Preparation of Intermediate 1.3:

3-[(Methylsulfanyl)methyl]-5-(trifluoromethyl)aniline

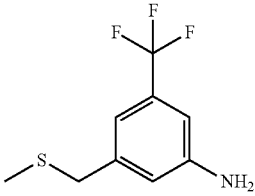

TFA (2.5 mL) was added to a stirred solution of tert-butyl {3-[(methylsulfanyl)methyl]-5-(tri-fluoromethyl) phenyl}carbamate (502 mg; 1.56 mmol) in DCM (5 mL) at 0° C. The ice bath was removed and the mixture was stirred for 45 min at RT. The batch was concentrated and saturated aqueous sodium bicarbonate solution was added. The batch was extracted with ethyl acetate (2×). The combined organic phases were dried (sodium sulfate), filtered and concentrated to give the crude product (336 mg) that was used without further purification.

$^1$H NMR (400 MHz, CDCl$_3$, 300K) δ=6.92 (s, 1H), 6.80 (s, 1H), 6.78 (s, 1H), 3.83 (br, 2H), 3.61 (s, 3H), 2.01 (s, 2H).

Preparation of Intermediate 1.4:

4-(2,4-Difluorophenyl)-5-fluoro-N-{3-[(methylsulfanyl)methyl]-5-(trifluoromethyl)phenyl}pyrimidin-2-amine

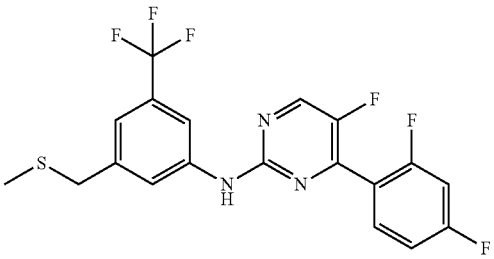 [SMILES: CSCc1cc(Nc2ncc(F)c(-c3ccc(F)cc3F)n2)cc(C(F)(F)F)c1]

A 4N solution of hydrogen chloride in dioxane (0.63 mL; 2.52 mmol) was added to a mixture of 2-chloro-4-(2,4-difluorophenyl)-5-fluoropyrimidine (618 mg; 2.53 mmol) and 3-[(methylsulfanyl)methyl]-5-(trifluoromethyl)aniline (658 mg; 2.53 mmol) in 1-butanol (7.5 mL) at room temperature. The batch was stirred at 140° C. for 3 days. After cooling, the batch was concentrated and the residue was purified by chromatography (hexane/ethyl acetate 7% to 60%) to give the desired product (711 mg; 1.54 mmol).

$^1$H NMR (400 MHz, CDCl$_3$, 300K) δ=8.41 (m, 1H), 7.98 (s, 1H), 7.73 (m, 1H), 7.71 (s, 1H), 7.29 (s, 1H), 7.22 (s, 1H), 7.06 (m, 1H), 6.98 (m, 1H), 3.70 (s, 2H), 2.02 (s, 3H).

Preparation of Intermediate 1.5:

(rac)-{[3-{[4-(2,4-Difluorophenyl)-5-fluoropyrimidin-2-yl]amino}-5-(trifluoromethyl)benzyl](methyl)-$\lambda^4$-sulfanylidene}cyanamide

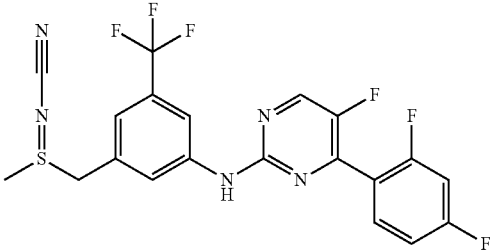 [SMILES: CS(Cc1cc(Nc2ncc(F)c(-c3ccc(F)cc3F)n2)cc(C(F)(F)F)c1)=NC#N]

Iodobenzene diacetate (228 mg; 0.69 mmol) was added to a stirred solution of 4-(2,4-difluorophenyl)-5-fluoro-N-{3-[(methylsulfanyl)methyl]-5-(trifluoromethyl) phenyl}pyrimidin-2-amine (304 mg; 0.63 mmol) and cyanamide (54 mg; 1.26 mmol) in DCM (4 mL) at 0° C. The batch was stirred for 40 minutes at 0° C. and 30 minutes at room temperature before it was purified by chromatography (DCM/EtOH 95:5) to give the pure product (297 mg; 0.63 mmol).

$^1$H NMR (400 MHz, d$_6$-DMSO, 300K) δ=10.41 (s, 1H), 8.75 (m, 1H), 8.28 (s, 1H), 8.03 (s, 1H), 7.85 (m, 1H), 7.46 (m, 1H), 7.34 (m, 2H), 4.57 (d, 1H), 4.35 (d, 1H), 2.88 (s, 3H).

Preparation of End Product:

Potassium permanganate (146 mg; 0.91 mmol) was added to a stirred solution of (rac)-{[3-{[4-(2,4-difluorophenyl)-5-fluoropyrimidin-2-yl]amino}-5-(trifluoromethyl)benzyl](methyl)-$\lambda^4$-sulfanylidene}cyanamide (304 mg; 0.45 mmol) in acetone (8.5 mL) at room temperature. The batch was stirred at 40° C. for 30 minutes. The batch was concentrated and the residue was purified by chromatography (DCM/EtOH 95:5) to give the desired product (210 mg; 0.39 mmol).

$^1$H NMR (400 MHz, d$_6$-DMSO, 300K) δ=10.43 (s, 1H), 8.77 (m, 1H), 8.32 (s, 1H), 8.09 (s, 1H), 7.84 (m, 1H), 7.50 (m, 1H), 7.41 (s, 1H), 7.33 (m, 1H), 5.10 (m, 2H), 3.41 (s, 3H).

Examples 2 and 3

Enantiomers of {[3-{[4-(2,4-Difluorophenyl)-5-fluoropyrimidin-2-yl]amino}-5-(trifluoromethyl)benzyl](methyl)oxido-λ$^6$-sulfanylidene}cyanamide

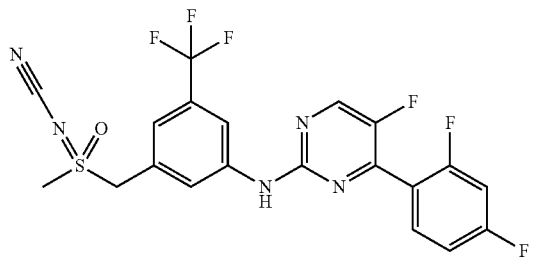 [SMILES: CS(=O)(Cc1cc(Nc2ncc(F)c(-c3ccc(F)cc3F)n2)cc(C(F)(F)F)c1)=NC#N]

(rac)-{[3-{[4-(2,4-Difluorophenyl)-5-fluoropyrimidin-2-yl]amino}-5-(trifluoromethyl)benzyl](methyl)oxido-λ$^6$-sulfanylidene}cyanamide was separated into the enantiomers by preparative HPLC.

| System: | Agilent: Prep 1200, 2xPrep Pump G1361A, DLA G2258A, MWD G1365D, Prep FC G1364B |
|---|---|
| Column: | Chiralpak IC 5 μm 250 × 20 mm |
| Solvent: | Hexan/IPA 80/20 (v/v) |
| Flow: | 30 mL/min |
| Temperature: | RT |
| Solution: | 134 mg/0.8 ml DMF |
| Injection: | 8 × 100 μl |
| Detection: | UV 280 nm |

| | Retention time in min | purity in % |
|---|---|---|
| Example 2 Enantiomer 1 | 6.8-7.5 | 98.4 |
| Example 3 Enantiomer 2 | 7.7-8.3 | >99 |

Example 4

(rac)-4-(2,4-Difluorophenyl)-5-fluoro-N-{3-[(S-methylsulfonimidoyl)methyl]-5-(trifluoromethyl)phenyl}pyrimidin-2-amine

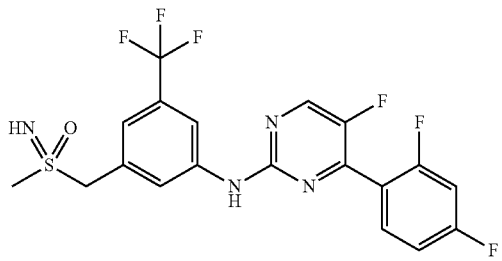 [SMILES: CS(=N)(=O)Cc1cc(Nc2ncc(F)c(-c3ccc(F)cc3F)n2)cc(C(F)(F)F)c1]

TFAA (0.043 mL; 0.31 mmol) was added to a stirred solution of (rac)-{[3-{[4-(2,4-difluorophenyl)-5-fluoropyrimidin-2-yl]amino}-5-(trifluoromethyl)benzyl](methyl)oxido-λ$^6$-sulfanylidene}cyanamide (69 mg; 0.13 mmol) in DCM (1.8 mL) at 0° C. The mixture was allowed to react at RT for 5 hours. Additional TFAA (0.086 mL; 0.62 mmol) was added and the mixture was stirred for 2 hours at RT. The reaction mixture was concentrated, redissolved in MeOH (0.9 mL) and treated with potassium carbonate (89 mg; 0.64 mmol). The mixture was allowed to react at RT for 100 minutes. The reaction mixture was diluted with ethyl acetate and THF and washed with saturated aqueous sodium chloride solution. The organic phase was filtered using a Whatman filter and concentrated. The residue was purified by chromatography (DCM/EtOH 92:8) to give the desired product (13 mg; 0.03 mmol).

$^1$H NMR (400 MHz, CDCl$_3$, 300K) δ=8.40 (m, 1H), 8.14 (s, 1H), 7.86 (s, 1H), 7.72 (m, 1H), 7.47 (s, 1H), 7.28 (s, 1H), 7.06 (m, 1H), 6.98 (m, 1H), 4.41 (d, 1H), 4.27 (d, 1H), 2.98 (s, 3H).

Example 5

4-(2,4-Difluorophenyl)-5-fluoro-N-{3-[(S-methylsulfonimidoyl)methyl]-5-(trifluoromethyl)phenyl}pyrimidin-2-amine; enantiomer 1

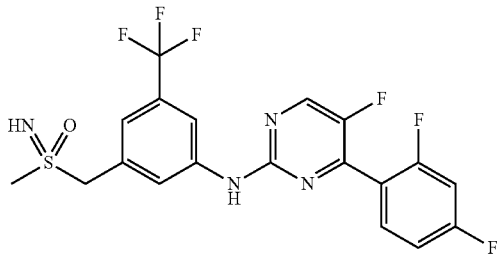

Example 5 was prepared under similar conditions as described in the preparation of Example 4 using {[3-{[4-(2,4-difluorophenyl)-5-fluoropyrimidin-2-yl]amino}-5-(trifluoromethyl)benzyl](methyl)oxido-λ$^6$-sulfanylidene}cyanamide, enantiomer 1.

Optical rotation index: 15.3°+/−0.12° (c=1.0000 g/100 mL DMSO; T=20° C.; wavelength: 589 nm)

Example 6

4-(2,4-Difluorophenyl)-5-fluoro-N-{3-[(S-methylsulfonimidoyl)methyl]-5-(trifluoromethyl)phenyl}pyrimidin-2-amine; enantiomer 2

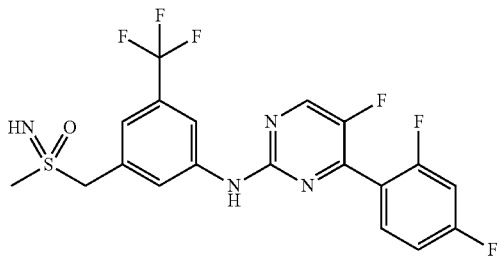

Example 6 was prepared under similar conditions as described in the preparation of Example 4 using {[3-{[4-(2,4-difluorophenyl)-5-fluoropyrimidin-2-yl]amino}-5-(trifluoromethyl)benzyl](methyl)oxido-λ⁶-sulfanylidene}cyanamide, enantiomer 2.

Optical rotation index: −18.2°+/−0.13° (c=1.0000 g/100 mL DMSO; T=20° C.; wavelength: 589 nm)

Example 7

(rac)-1-{[3-{[4-(2,4-Difluorophenyl)-5-fluoropyrimidin-2-yl]amino}-5-(trifluoromethyl)benzyl](methyl)oxido-λ⁶-sulfanylidene}urea

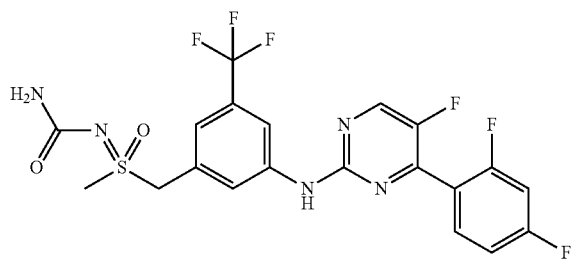 [SMILES: CS(=O)(Cc1cc(Nc2ncc(F)c(-c3ccc(F)cc3F)n2)cc(C(F)(F)F)c1)=NC(N)=O]

TFAA (0.009 mL; 0.063 mmol) was added to a stirred solution of (rac)-{[3-{[4-(2,4-difluorophenyl)-5-fluoropyrimidin-2-yl]amino}-5-(trifluoromethyl)benzyl](methyl)oxido-λ⁶-sulfanylidene}cyanamide (11 mg; 0.021 mmol) in DCM (1.0 mL) at 0° C. The mixture was allowed to react at RT for 17 hours. The reaction mixture was concentrated and the residue was purified by chromatography (DCM/EtOH 93:7) to give the desired product (4.1 mg; 0.01 mmol).

$^1$H NMR (400 MHz, d$_6$-DMSO, 300K) δ=10.30 (s, 1H), 8.74 (m, 1H), 8.17 (s, 1H), 8.04 (s, 1H), 7.82 (m, 1H), 7.47 (m, 1H), 7.36 (s, 1H), 7.30 (m, 1H), 6.24 (br, 1H), 6.06 (br, 1H), 4.87 (m, 2H), 3.00 (s, 3H).

Example 8

(rac)-Ethyl[(3-{[4-(2,4-difluorophenyl)-5-fluoropyrimidin-2-yl]amino}benzyl)(methyl)oxido-λ⁶-sulfanylidene]carbamate

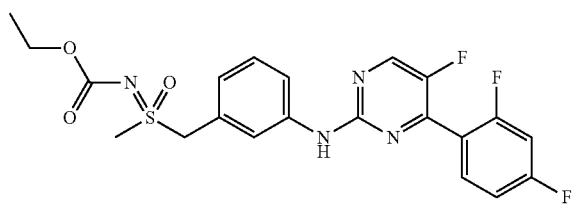 [SMILES: CCOC(=O)N=S(C)(=O)Cc1cccc(Nc2ncc(F)c(-c3ccc(F)cc3F)n2)c1]

Preparation of Intermediate 8.1:

1-[(Methylsulfanyl)methyl]-3-nitrobenzene

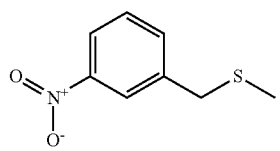

Sodium methanethiolate (13.5 g; 192 mmol) was added in two portions to a stirred solution of 1-(chloromethyl)-3-nitrobenzene (30.0 g; 175 mmol; Aldrich Chemical Company Inc.) in ethanol (360 mL) at −15° C. The cold bath was removed and the batch was stirred at room temperature for 3 hours. The batch was diluted with saturated aqueous sodium chloride solution and extracted with ethyl acetate (2×). The combined organic phases were washed with water, dried (sodium sulfate), filtered and concentrated to give the desired product (32.2 g) that was used without further purification.

$^1$H NMR (400 MHz, CDCl$_3$, 300K) δ=8.18 (m, 1H), 8.11 (m, 1H), 7.66 (m, 1H), 7.50 (m, 1H), 3.75 (s, 2H), 2.01 (s, 3H).

Preparation of Intermediate 8.2:

(rac)-1-[(Methylsulfinyl)methyl]-3-nitrobenzene

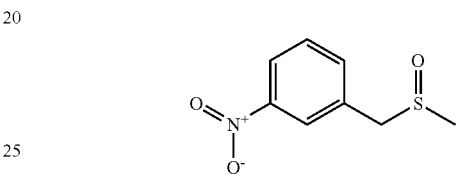

Iron(III)chloride (0.55 g; 3.4 mmol) was added to a solution of 1-[(methylsulfanyl)methyl]-3-nitrobenzene (21.6 g; 117.9 mmol) in MeCN (280 mL) and the batch was stirred at room temperature for 10 minutes. Periodic acid (28.8 g; 126.1 mmol) was added under stirring in one portion and the temperature was kept below 30° C. by cooling. The batch was stirred at room temperature for 90 minutes before it was added to a stirred solution of sodium thiosulfate pentahydrate (163 g; 660 mmol) in ice water (1500 mL). The batch was saturated with solid sodium chloride and extracted with THF (2×).

The combined organic phases were washed with saturated aqueous sodium chloride solution, dried (sodium sulfate), filtered and concentrated. The residue was purified by chromatography (DCM/ethanol 95:5) to give the desired product (16.6 g; 83.1 mmol).

$^1$H NMR (400 MHz, CDCl$_3$, 300K) δ=8.21 (m, 1H), 8.17 (m, 1H), 7.67 (m, 1H), 7.58 (m, 1H), 4.10 (d, 1H), 3.97 (d, 1H), 2.53 (s, 3H).

Preparation of Intermediate 8.3:

(rac)-2,2,2-Trifluoro-N-[methyl(3-nitrobenzyl)oxido-λ⁶-sulfanylidene]acetamide

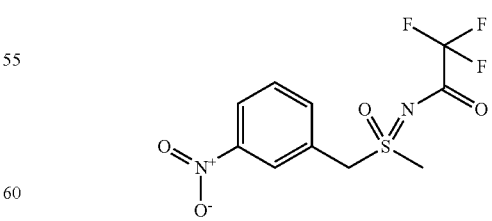

To a suspension of (rac)-1-[(methylsulfinyl)methyl]-3-nitrobenzene (16.6 g; 83.1 mmol), trifluoroacetamide (18.8 g; 166.1 mmol), magnesium oxide (13.4 g; 332.3 mmol) and rhodium(II)-acetate dimer (1.7 g; 8.3 mmol) in DCM (2290 mL) was added iodobenzene diacetate (40.1 g; 124.6 mmol)

at room temperature. The batch was stirred for 16 hours at room temperature, filtered and concentrated. The residue was purified by chromatography (DCM/ethanol 97:3) to give the desired product (25.6 g; 82.4 mmol).

$^1$H NMR (400 MHz, CDCl$_3$, 300K) δ=8.36 (m, 1H), 8.31 (m, 1H), 7.80 (m, 1H), 7.69 (m, 1H), 4.91 (d, 1H), 4.79 (d, 1H), 3.28 (s, 3H).

Preparation of Intermediate 8.4:

(rac)-1-[(S-Methylsulfonimidoyl)methyl]-3-nitrobenzene

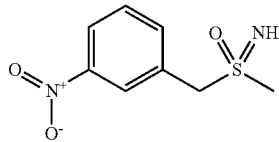

Potassium carbonate (56.9 g; 411.8 mmol) was added to a solution of (rac)-2,2,2-trifluoro-N-[methyl(3-nitrobenzyl)oxido-λ$^6$-sulfanylidene]acetamide (25.6 g; 82.4 mmol) in MeOH (1768 mL) at room temperature. The batch was stirred for 1 hour at room temperature before it was diluted with ethyl acetate and saturated aqueous sodium chloride solution. After extraction with ethyl acetate (2×) the combined organic phases were dried (sodium sulfate), filtered and concentrated to give the desired product (13.9 g; 65.1 mmol).

$^1$H NMR (400 MHz, CDCl$_3$, 300K) δ=8.29 (m, 2H), 7.79 (m, 1H), 7.63 (m, 1H), 4.47 (d, 1H), 4.34 (d, 1H), 2.99 (s, 3H), 2.66 (br, 1H).

Preparation of Intermediate 8.5:

(rac)-Ethyl [methyl(3-nitrobenzyl)oxido-λ$^6$-sulfanylidene]carbamate

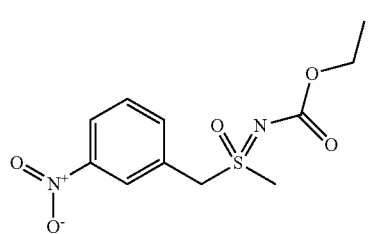 [SMILES: CCOC(=O)N=S(C)(=O)Cc1cccc([N+](=O)[O-])c1]

Ethyl chlorocarbonate (8.1 mL; 84.6 mmol) was added dropwise to a stirred solution of (rac)-1-[(S-methylsulfonimidoyl)methyl]-3-nitrobenzene (13.9 g; 65.1 mmol) in pyridine (615 mL) at 0° C. The batch was slowly warmed to room temperature. After 24 hours the batch was concentrated and the residue was dissolved in ethyl acetate and washed with saturated aqueous sodium chloride solution. The organic phase was filtered using a Whatman filter and concentrated to give the desired product (19.7 g) that was used without further purification.

$^1$H NMR (400 MHz, CDCl$_3$, 300K) δ=8.30 (m, 2H), 7.81 (m, 1H), 7.64 (m, 1H), 4.88 (d, 1H), 4.79 (d, 1H), 4.18 (q, 2H), 3.07 (s, 3H), 1.31 (tr, 3H).

Preparation of Intermediate 8.6:

(rac)-Ethyl [(3-aminobenzyl)(methyl)oxido-λ$^6$-sulfanylidene]carbamate

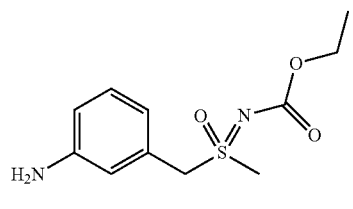 [SMILES: CCOC(=O)N=S(C)(=O)Cc1cccc(N)c1]

Titanium(III)chloride solution (approx. 15% in approx. 10% hydrochloric acid, 118 mL; Merck Schuchardt OHG) was added to a stirred solution of (rac)-ethyl [methyl(3-nitrobenzyl)oxido-λ$^6$-sulfanylidene]carbamate (5.0 g; 17.5 mmol) in THF (220 mL) at room temperature. The batch was stirred for 18 hours. By adding 2N sodium hydroxide solution the pH value of the reaction mixture, that was cooled with an ice bath, was raised to 8. The batch was saturated with solid sodium chloride and extracted with ethyl acetate (3×). The combined organic phases were washed with saturated aqueous sodium chloride solution, dried (sodium sulfate), filtered and concentrated to give the desired product (4.2 g) that was used without further purification.

$^1$H NMR (400 MHz, d$_6$-DMSO, 300K) δ=7.00 (m, 1H), 6.53 (m, 3H), 5.18 (br, 2H), 4.62 (s, 2H), 3.95 (m, 2H), 3.08 (s, 3H). 1.13 (tr, 3H).

Preparation of End Product:

A batch with (rac)-ethyl[(3-aminobenzyl)(methyl)oxido-λ$^6$-sulfanylidene]carbamate (419 mg; 1.64 mmol), 2-chloro-4-(2,4-difluorophenyl)-5-fluoropyrimidine (400 mg; 1.64 mmol), chloro(2-dicyclohexylphosphino-2',4',6'-tri-iso-propyl-1,1'-biphenyl)[2-(2-aminoethyl)phenyl]palladium(II) methyl-tert-butylether adduct (101 mg; 0.12 mmol; ABCR GmbH & CO. KG), 2-dicyclohexylphosphino-2',4',6'-triisopropylbiphenyl (58 mg; 0.12 mmol; Aldrich Chemical Company Inc.) and potassium phosphate (347 mg; 1.63 mmol) in toluene (12.0 ml) and 1-methylpyrrolidin-2-one (2.4 ml) was degassed using argon. The batch was stirred under an atmosphere of argon for 3 hours at 130° C. in a microwave oven. After cooling, the batch was diluted with saturated aqueous sodium chloride solution and extracted with ethyl acetate (2×). The combined organic phases were filtered using a Whatman filter and concentrated. The residue was purified by chromatography (DCM/EtOH 95:5) to give the desired product (430 mg; 0.93 mmol).

$^1$H NMR (400 MHz, CDCl$_3$, 300K) δ=8.39 (m, 1H), 7.90 (m, 1H), 7.72 (m, 1H), 7.56 (m, 1H), 7.37 (m, 1H), 7.31 (s, 1H), 7.07 (m, 2H), 6.98 (m, 1H), 4.71 (m 2H), 4.17 (q, 2H), 2.98 (s, 3H), 1.31 (tr, 3H).

Example 9

(rac)-4-(2,4-Difluorophenyl)-5-fluoro-N-{3-[(S-methylsulfonimidoyl)methyl]phenyl}pyrimidin-2-amine

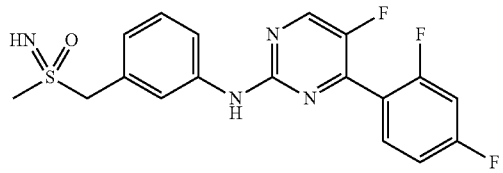 [SMILES: CS(=N)(=O)Cc1cccc(Nc2ncc(F)c(-c3ccc(F)cc3F)n2)c1]

A freshly prepared 2M solution of sodium ethanolate in ethanol (108 μL; 0.22 mmol) was added under argon to a solution of (rac)-ethyl[(3-{[4-(2,4-difluorophenyl)-5-fluoropyrimidin-2-yl]amino}benzyl)(methyl)oxido-λ$^6$-sulfanylidene]carbamate (100 mg; 0.22 mmol) in ethanol (0.5 mL). The batch was stirred at 60° C. for 21 hours. Further 2M solution of sodium ethanolate in ethanol (22 μL; 0.04 mmol) was added and the batch was stirred for additional 23 hours at 60° C. Further 2M solution of sodium ethanolate in ethanol (43 μL; 0.09 mmol) was added and the batch was stirred for additional 28 hours at 60° C. Further 2M solution of sodium ethanolate in ethanol (64 μL; 0.13 mmol) was added and the batch was stirred for additional 90 minutes at 60° C.

After cooling the batch was diluted with an aqueous solution of sodium chloride and extracted with ethyl acetate (3×). The combined organic phases were filtered using a Whatman filter and concentrated. The residue was purified by preparative HPLC to give the desired product (43 mg; 0.11 mmol).

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ = 8.38 (m, 1H), 7.80 (s, 1H), 7.71 (m, 1H), 7.59 (m, 1H), 7.37 (m, 1H), 7.00 (m, 3H), 4.38 (d, 1H), 4.25 (d, 1H), 2.93 (s, 3H), 2.67 (br, 1H).

Example 10

(rac)-[(3-{[4-(2,4-Difluorophenyl)-5-fluoropyrimidin-2-yl]amino}-5-fluorobenzyl)(methyl)oxido-λ$^6$-sulfanylidene]cyanamide

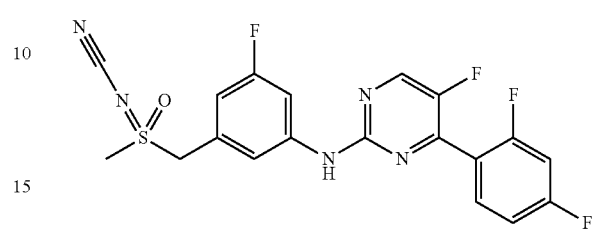

Preparation of Intermediate 10.1:

1-Fluoro-3-[(methylsulfanyl)methyl]-5-nitrobenzene

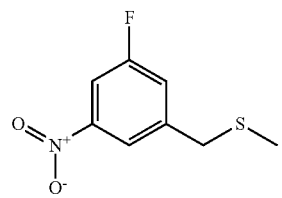

Intermediate 10.1 was prepared under similar conditions as described in the preparation of Intermediate 8.1 using 1-(chloromethyl)-3-fluoro-5-nitrobenzene (Hansa Fine Chemicals GmbH).

$^1$H NMR (400 MHz, CDCl$_3$, 300K) δ=8.00 (m, 1H), 7.82 (m, 1H), 7.44 (m, 1H), 3.74 (s, 2H), 2.03 (s, 3H).

Preparation of Intermediate 10.2:

3-Fluoro-5-[(methylsulfanyl)methyl]aniline

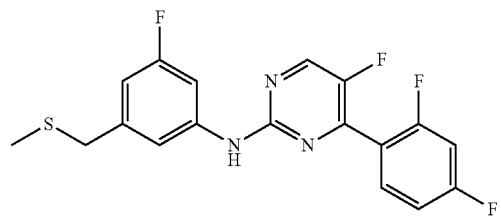

Titanium(III)chloride solution (approx. 15% in approx. 10% hydrochloric acid, 101 mL; Merck Schuchardt OHG) was added to a stirred solution of 1-fluoro-3-[(methylsulfanyl)methyl]-5-nitrobenzene (3.00 g; 14.9 mmol) in THF (150 mL) at RT. The batch was stirred for 17 hours. By adding 2N sodium hydroxide solution the pH value of the reaction mixture, that was cooled with an ice bath, was raised to 8. The aqueous layer was extracted with ethyl acetate (3×). The combined organic phases were filtered using a Whatman filter and concentrated to give the crude product (2.55 g) that was used without further purification.

$^1$H NMR (400 MHz, CDCl$_3$, 300K) δ=6.41 (m, 2H), 6.26 (m, 1H), 3.74 (br, 2H), 3.55 (s, 2H), 2.01 (s, 3H).

Preparation of Intermediate 10.3:

4-(2,4-Difluorophenyl)-5-fluoro-N-{3-fluoro-5-[(methylsulfanyl)methyl]phenyl}pyrimidin-2-amine

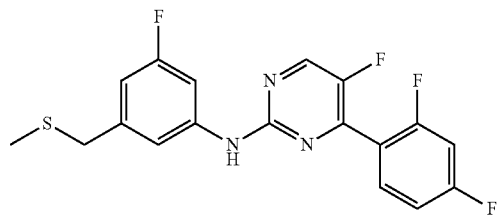 [SMILES: CSCc1cc(F)cc(Nc2ncc(F)c(-c3ccc(F)cc3F)n2)c1]

A batch with 3-fluoro-5-[(methylsulfanyl)methyl]aniline (500 mg; 2.92 mmol), 2-chloro-4-(2,4-difluorophenyl)-5-fluoropyrimidine (928 mg; 3.89 mmol), chloro(2-dicyclohexylphosphino-2',4',6'-tri-iso-propyl-1,1'-biphenyl)[2-(2-aminoethyl)phenyl]palladium(II) methyl-tert-butylether adduct (181 mg; 0.22 mmol; ABCR GmbH & CO. KG), 2-dicyclohexylphosphino-2',4',6'-triisopropylbiphenyl (104 mg; 0.22 mmol; Aldrich Chemical Company Inc.) and potassium phosphate (3098 mg; 14.6 mmol) in toluene (19.5 ml) and 1-methylpyrrolidin-2-one (3.9 ml) was degassed using argon. The batch was stirred under an atmosphere of argon for 3 hours at 130° C. After cooling, the batch was diluted with saturated aqueous sodium chloride solution and extracted with ethyl acetate (2×). The combined organic phases were filtered using a Whatman filter and concentrated. The residue was purified by chromatography (hexane to hexane/ethyl acetate 27%) to give the desired product (747 mg; 1.97 mmol).

$^1$H NMR (400 MHz, CDCl$_3$, 300K) δ=8.39 (m, 1H), 7.71 (m, 1H), 7.56 (m 1H), 7.18 (s, 1H), 7.06 (m, 1H), 6.98 (m, 1H), 6.70 (m, 1H), 3.64 (s, 2H), 2.02 (s, 3H).

Preparation of Intermediate 10.4:

(rac)-[(3-{[4-(2,4-Difluorophenyl)-5-fluoropyrimidin-2-yl]amino}-5-fluorobenzyl)(methyl)-λ$^4$-sulfanylidene]cyanamide

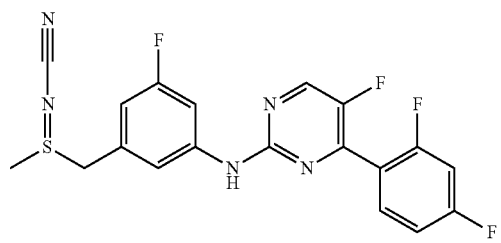 [SMILES: CS(Cc1cc(F)cc(Nc2ncc(F)c(-c3ccc(F)cc3F)n2)c1)=NC#N]

Iodobenzene diacetate (696 mg; 2.16 mmol) was added to a stirred solution of 4-(2,4-difluorophenyl)-5-fluoro-N-{3-fluoro-5-[(methylsulfanyl)methyl]phenyl}pyrimidin-2-amine (745 mg; 1.96 mmol) and cyanamide (165 mg; 3.93 mmol) in DCM (11 mL) at 0° C. The batch was stirred for 4 hours at 0° C. before it was purified by chromatography (hexane/ethyl acetate 35%-100%) to give the pure product (628 mg; 1.50 mmol).

$^1$H NMR (400 MHz, CDCl$_3$, 300K) δ=8.43 (m, 1H), 7.70 (m, 1H), 7.62 (m, 1H), 7.42 (m, 1H), 7.38 (s, 1H), 7.08 (m, 1H), 7.00 (m, 1H), 6.71 (m, 1H), 4.39 (d, 1H), 4.13 (d, 1H), 2.77 (s, 3H).

Preparation of End Product:

Potassium permanganate (467 mg; 2.96 mmol) was added to a stirred solution of ((rac)-[(3-{[4-(2,4-difluorophenyl)-5-fluoropyrimidin-2-yl]amino}-5-fluorobenzyl)(methyl)-λ$^4$-sulfanylidene]cyanamide (620 mg; 1.48 mmol) in acetone (14.7 mL) at RT. The batch was stirred at 50° C. for 1 hour. The batch was concentrated and the residue was purified by chromatography (hexane/ethyl acetate 20%-100%) to give the desired product (398 mg; 0.91 mmol).

$^1$H NMR (400 MHz, CDCl$_3$, 300K) δ=8.43 (m, 1H), 7.69 (m, 2H), 7.55 (s, 1H), 7.44 (s, 1H), 7.08 (m, 1H), 6.99 (m, 1H), 6.79 (m, 1H), 4.58 (m, 2H), 3.07 (s, 3H).

Example 11

(rac)-4-(2,4-Difluorophenyl)-5-fluoro-N-{3-fluoro-5-[(S-methylsulfonimidoyl)methyl]phenyl}pyrimidin-2-amine

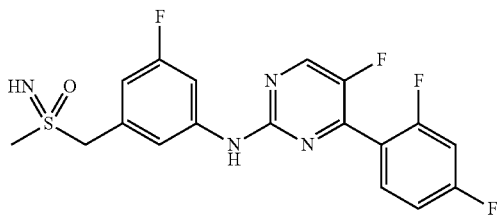

TFAA (0.38 mL; 2.69 mmol) was added to a stirred solution of (rac)-[(3-{[4-(2,4-difluorophenyl)-5-fluoropyrimidin-2-yl]amino}-5-fluorobenzyl)(methyl)oxido-λ$^6$-sulfanylidene]cyanamide (390 mg; 0.90 mmol) in DCM (40.0 mL) at 0° C. The mixture was allowed to react at RT for 2 hours. The reaction mixture was concentrated, re-dissolved in MeOH (6.3 mL) and treated with potassium carbonate (619 mg; 4.48 mmol). The mixture was allowed to react at RT for 2 hours. The reaction mixture was diluted with ethyl acetate and THF and washed with saturated aqueous sodium chloride solution. The organic phase was filtered using a Whatman filter and concentrated. The residue was purified by chromatography (DCM/EtOH 0% to 20%) to give the desired product (121 mg; 0.29 mmol).

$^1$H NMR (400 MHz, CDCl$_3$, 300K) δ=8.39 (m, 1H), 7.69 (m, 2H), 7.39 (s, 1H), 7.35 (s, 1H), 7.06 (m, 1H), 6.98 (m, 1H), 6.78 (m, 1H), 4.34 (d, 1H), 4.30 (d, 1H), 2.96 (s, 3H).

Examples 12 and 13

Enantiomers of 4-(2,4-Difluorophenyl)-5-fluoro-N-{3-fluoro-5-[(S-methylsulfonimidoyl)methyl]phenyl}pyrimidin-2-amine

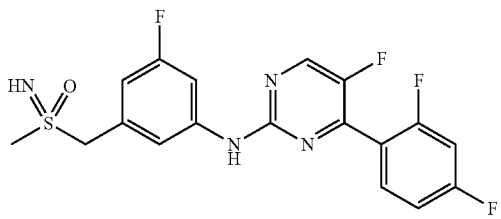

(rac)-4-(2,4-Difluorophenyl)-5-fluoro-N-{3-fluoro-5-[(S-methylsulfonimidoyl)methyl]phenyl}pyrimidin-2-amine was separated into the enantiomers by preparative HPLC.

| System: | Agilent: Prep 1200, 2 × Prep Pump G1361A, DLA G2258A, MWD G1365D, Prep FC G1364B |
|---|---|
| Column: | Chiralpak IA 5 µm 250 × 20 mm |
| Solvent: | EtOH/MeOH 50/50 (v/v) |
| Flow: | 20 mL/min |
| Temperature: | RT |
| Solution: | 116 mg/2.2 mL DMF |
| Injection: | 22 × 100 µl |
| Detection: | UV 254 nm |

| | Retention time in min | purity in % |
|---|---|---|
| Example 12 Enantiomer 1 | 5.4-7.0 | 98.9 |
| Example 13 Enantiomer 2 | 7.4-10.5 | 99.7 |

Example 14

(rac)-[(3-Chloro-5-{[4-(2,4-difluorophenyl)-5-fluoropyrimidin-2-yl]amino}benzyl)(methyl)oxido-λ⁶-sulfanylidene]cyanamide

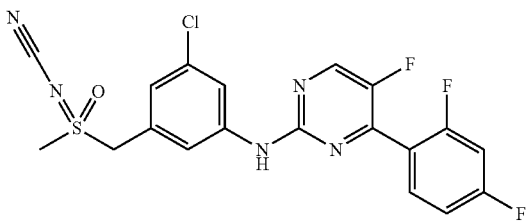

Preparation of Intermediate 14.1:

(3-Chloro-5-nitrophenyl)methanol

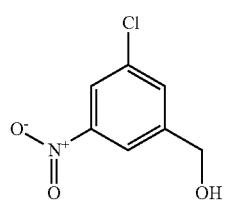 [SMILES: O=[N+]([O-])c1cc(Cl)cc(CO)c1]

To a stirred solution of 3-chloro-5-nitrobenzoic acid (5.00 g; 24.8 mmol; ABCR GmbH & CO. KG) in THF (48 mL) at 0° C. was added a 1M solution of borane-THF complex in THF (99.2 mL; 99.2 mmol). The mixture was allowed to react at RT overnight. Then, MeOH was cautiously added to the stirred mixture while cooling with an ice bath. The batch was diluted with ethyl acetate and washed with aqueous sodium hydroxide solution (1N) and saturated aqueous sodium chloride solution. The organic phase was dried (sodium sulfate), filtered and concentrated. The residue was purified by chromatography hexane/ethyl acetate 50% to 100%) to give the pure product (4.22 g; 22.5 mmol).
¹H NMR (400 MHz, CDCl₃, 300K) δ=8.13 (m, 2H), 7.71 (s, 1H), 4.81 (m, 2H), 2.00 (br, 1H).

Preparation of Intermediate 14.2:

1-Chloro-3-(chloromethyl)-5-nitrobenzene

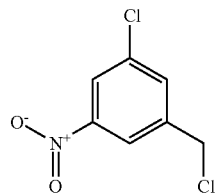 [SMILES: O=[N+]([O-])c1cc(Cl)cc(CCl)c1]

To a stirring solution of (3-chloro-5-nitrophenyl)methanol (4.20 g; 22.4 mmol) in DCM (67 mL) and NMP (9 mL) at RT was added dropwise thionyl chloride (4.1 mL; 60.0 mmol). The mixture was allowed to react at RT overnight. Then, the mixture was poured into aqueous sodium bicarbonate solution/saturated aqueous sodium chloride solution/ ice. The batch was stirred for 15 minutes before it was extracted with ethyl acetate (2×). The combined organic phases were filtered using a Whatman filter and concentrated to give the crude product (6.40 g) that was used without further purification.
¹H NMR (400 MHz, CDCl₃, 300K) δ=8.17 (m, 2H), 7.72 (s, 1H), 4.62 (s, 2H).

Preparation of Intermediate 14.3:

1-Chloro-3-[(methylsulfanyl)methyl]-5-nitrobenzene

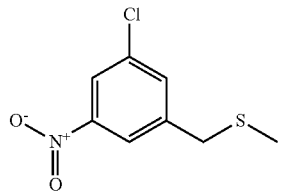

Intermediate 14.3 was prepared under similar conditions as described in the preparation of Intermediate 1.2 using 1-chloro-3-(chloromethyl)-5-nitrobenzene.
¹H NMR (400 MHz, CDCl₃, 300K) δ=8.11 (m, 1H), 8.08 (s, 1H), 7.66 (s, 1H), 3.72 (m, 2H), 2.03 (s, 3H).

Preparation of Intermediate 14.4:

3-Chloro-5-[(methylsulfanyl)methyl]aniline

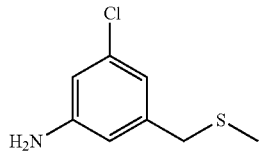

Intermediate 14.4 was prepared under similar conditions as described in the preparation of Intermediate 8.6 using 1-chloro-3-[(methylsulfanyl)methyl]-5-nitrobenzene.
¹H NMR (400 MHz, CDCl₃, 300K) δ=6.68 (m, 1H), 6.56 (m, 1H), 6.52 (m, 1H), 3.73 (br, 2H), 3.53 (s, 2H), 2.01 (s, 3H).

Preparation of Intermediate 14.5:

N-{3-Chloro-5-[(methylsulfanyl)methyl]phenyl}-4-(2,4-difluorophenyl)-5-fluoropyrimidin-2-amine

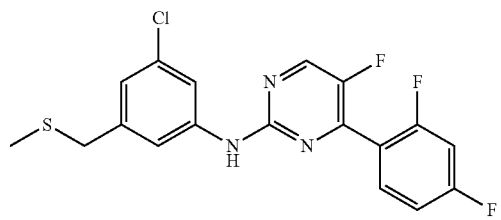 [SMILES: CSCc1cc(Cl)cc(Nc2ncc(F)c(-c3ccc(F)cc3F)n2)c1]

Intermediate 14.5 was prepared under similar conditions as described in the preparation of Intermediate 10.3 using 3-chloro-5-[(methylsulfanyl)methyl]aniline and 2-chloro-4-(2,4-difluorophenyl)-5-fluoropyrimidine.

$^1$H NMR (400 MHz, CDCl$_3$, 300K) δ=8.39 (m, 1H), 7.72 (m, 2H), 7.41 (s, 1H), 7.21 (s, 1H), 7.06 (m, 1H), 6.97 (m, 2H), 3.62 (s, 2H), 2.01 (s, 3H).

Preparation of Intermediate 14.6:

(rac)-[(3-Chloro-5-{[4-(2,4-difluorophenyl)-5-fluoropyrimidin-2-yl]amino}benzyl)(methyl)-λ$^4$-sulfanylidene]cyanamide

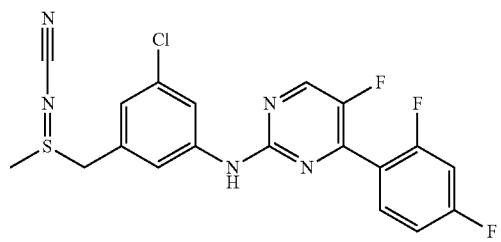 [SMILES: CS(Cc1cc(Cl)cc(Nc2ncc(F)c(-c3ccc(F)cc3F)n2)c1)=NC#N]

Intermediate 14.6 was prepared under similar conditions as described in the preparation of Intermediate 10.4 using N-{3-chloro-5-[(methylsulfanyl)methyl]phenyl}-4-(2,4-difluorophenyl)-5-fluoropyrimidin-2-amine.

$^1$H NMR (400 MHz, CDCl$_3$, 300K) δ=8.43 (m, 1H), 7.75 (m, 1H), 7.70 (m, 1H), 7.66 (m, 1H), 7.34 (s, 1H), 7.08 (m, 1H), 6.99 (m, 2H), 4.37 (d, 1H), 4.13 (d, 1H), 2.77 (s, 3H).

Preparation of End Product:

Example 14 was prepared under similar conditions as described in the preparation of Example 10 using (rac)-[(3-chloro-5-{[4-(2,4-difluorophenyl)-5-fluoropyrimidin-2-yl]amino}benzyl)(methyl)-λ$^4$-sulfanylidene]cyanamide. The batch was purified by chromatography (hexane to hexane/ethyl acetate 75%).

$^1$H NMR (400 MHz, d$_6$-DMSO, 300K) δ=10.24 (s, 1H), 8.71 (m, 1H), 7.95 (m, 1H), 7.79 (m, 2H), 7.46 (m, 1H), 7.30 (m, 1H), 7.08 (m, 1H), 4.96 (m, 2H), 3.36 (s, 3H).

Example 15

(rac)-N-{3-Chloro-5-[(S-methylsulfonimidoyl)methyl]phenyl}-4-(2,4-difluorophenyl)-5-fluoropyrimidin-2-amine

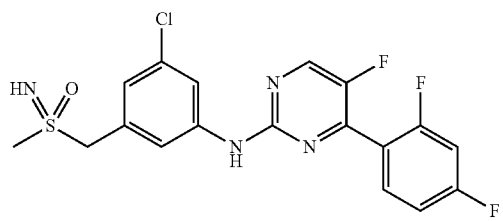

Example 15 was prepared under similar conditions as described in the preparation of Example 11 using (rac)-[(3-Chloro-5-{[4-(2,4-difluorophenyl)-5-fluoropyrimidin-2-yl]amino}benzyl)(methyl)oxido-λ$^6$-sulfanylidene]cyanamide. The batch was purified by chromatography (DCM/EtOH 94:6).

$^1$H NMR (400 MHz, CDCl$_3$, 300K) δ=8.40 (m, 1H), 7.83 (m, 1H), 7.71 (m, 1H), 7.57 (m, 1H), 7.32 (s, 1H), 7.06 (m, 2H), 6.98 (m, 1H), 4.32 (d, 1H), 4.19 (d, 1H), 2.96 (s, 3H), 2.73 (br, 1H).

Example 16

(rac)-[(3-{[4-(2,4-Difluorophenyl)-5-fluoropyrimidin-2-yl]amino}-5-methylbenzyl)(methyl)oxido-λ$^6$-sulfanylidene]cyanamide

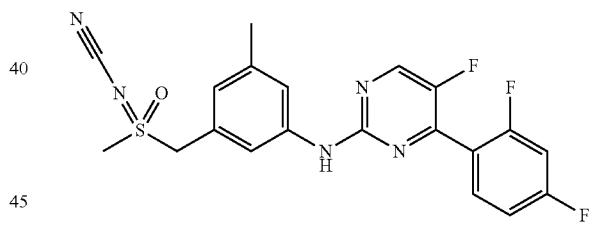

Preparation of Intermediate 16.1:

3-(Chloromethyl)-5-methylaniline

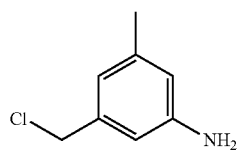

To a solution of (3-amino-5-methylphenyl)methanol (6.98 g; 47.3 mmol; ABCR GmbH & CO. KG) in DCM (155 mL) at 0° C. was added dropwise thionyl chloride (10.3 mL; 141.9 mmol). The mixture was allowed to react at RT overnight. Then, the mixture was evaporated. The resulting material was redissolved in DCM and evaporated again. The resulting solid (9.8 g) was used without further purification.

Preparation of Intermediate 16.2:

3-Methyl-5-[(methylsulfanyl)methyl]aniline

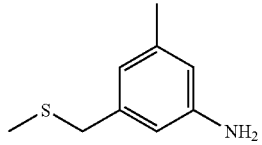

Intermediate 16.2 was prepared under similar conditions as described in the preparation of Intermediate 8.1 using 3-(chloromethyl)-5-methylaniline (Intermediate 16.1).

$^1$H NMR (400 MHz, d$_6$-DMSO, 300 K) δ=6.30 (s, 1H), 6.25 (s, 2H), 4.95 (s, 2H), 3.47 (s, 2H), 2.12 (s, 3H), 1.94 (s, 3H).

Preparation of Intermediate 16.3:

4-(2,4-Difluorophenyl)-5-fluoro-N-{3-methyl-5-[(methylsulfanyl)methyl]phenyl}pyrimidin-2-amine

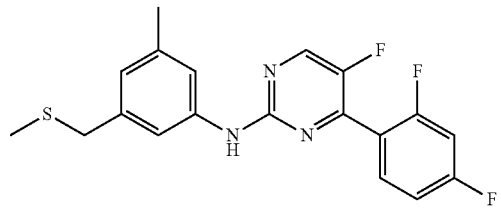 [SMILES: CSCc1cc(C)cc(Nc2ncc(F)c(-c3ccc(F)cc3F)n2)c1]

Intermediate 16.3 was prepared under similar conditions as described in the preparation of Intermediate 10.3 using 3-methyl-5-[(methylsulfanyl)methyl]aniline and 2-chloro-4-(2,4-difluorophenyl)-5-fluoropyrimidine (Intermediate 1.1).

$^1$H NMR (400 MHz, d$_6$-DMSO, 300 K) δ=9.78 (s, 1H), 8.67 (d, 1H), 7.82 (trd, 1H), 7.55 (s, 1H), 7.48 (ddd, 1H), 7.40 (s, 1H), 7.33 (trd, 1H), 6.72 (s, 1H), 3.60 (s, 2H), 2.25 (s, 3H), 1.96 (s, 3H).

Preparation of Intermediate 16.4:

(rac)-(3-{[4-(2,4-Difluorophenyl)-5-fluoropyrimidin-2-yl]amino}-5-methylbenzyl)(methyl)-λ$^4$-sulfanylidene]cyanamide

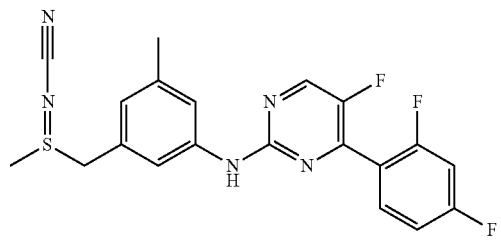 [SMILES: Cc1cc(CS(C)=NC#N)cc(Nc2ncc(F)c(-c3ccc(F)cc3F)n2)c1]

Intermediate 16.4 was prepared under similar conditions as described in the preparation of Intermediate 1.5 using 4-(2,4-difluorophenyl)-5-fluoro-N-{3-methyl-5-[(methylsulfanyl)methyl]phenyl}pyrimidin-2-amine (Intermediate 16.3).

$^1$H NMR (400 MHz, d$_6$-DMSO, 300 K) δ=9.95 (s, 1H), 8.68 (d, 1H), 7.86 (trd, 1H), 7.66 (s, 1H), 7.54 (s, 1H), 7.48 (trd, 1H), 7.34 (trd, 1H), 6.84 (s, 1H), 4.40 (d, 1H), 4.22 (d, 1H), 2.83 (s, 3H), 2.29 (s, 3H).

Preparation of End Product:

Example 16 was prepared under similar conditions as described in the preparation of Example 10 (final step) using (rac)-(3-{[4-(2,4-difluorophenyl)-5-fluoropyrimidin-2-yl]amino}-5-methylbenzyl)(methyl)-λ$^4$-sulfanylidene]cyanamide.

$^1$H NMR (400 MHz, d$_6$-DMSO, 300 K) δ=9.96 (s, 1H), 8.68 (d, 1H), 7.84 (trd, 1H), 7.71 (s, 1H), 7.58 (s, 1H), 7.52-7.43 (m, 1H), 7.32 (trd, 1H), 6.89 (s, 1H), 4.96-4.83 (m, 2H), 3.35 (s, 3H), 2.30 (s, 3H).

Example 17

(rac)-4-(2,4-Difluorophenyl)-5-fluoro-N-{3-methyl-5-[(S-methylsulfonimidoyl)methyl]phenyl}pyrimidin-2-amine

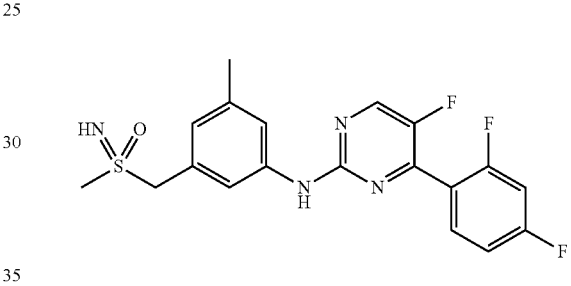

Example 17 was prepared under similar conditions as described in the preparation of Example 11 using (rac)-[(3-{[4-(2,4-difluorophenyl)-5-fluoropyrimidin-2-yl]amino}-5-methylbenzyl)(methyl)oxido-λ$^6$-sulfanylidene]cyanamide. The batch was purified by chromatography (EtOAc/EtOH 9:1).

$^1$H NMR (400 MHz, d$_6$-DMSO, 300 K) δ=9.83 (s, 1H), 8.66 (d, 1H), 7.83 (trd, 1H), 7.60 (s, 1H), 7.52-7.44 (m, 2H), 7.32 (trd, 1H), 6.84 (s, 1H), 4.32-4.21 (m, 2H), 3.52 (s, 1H), 2.79 (s, 3H), 2.28 (s, 3H).

Example 18

(rac)-[(3-Bromo-5-{[4-(2,4-difluorophenyl)-5-fluoropyrimidin-2-yl]amino}benzyl)(methyl)oxido-λ$^6$-sulfanylidene]cyanamide

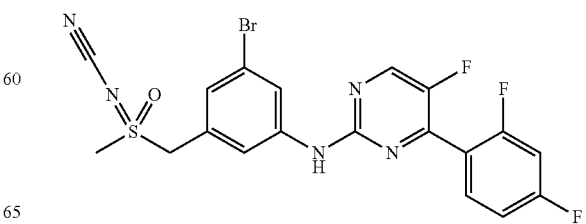

Preparation of Intermediate 18.1:

Bis{3-bromo-5-[(methylsulfanyl)methyl]phenyl}diazene oxide

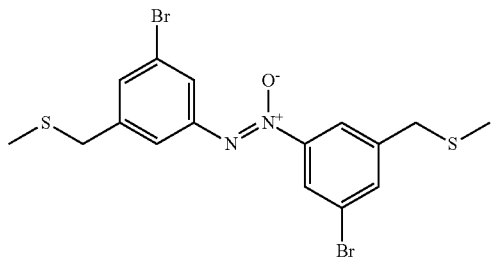

To a stirred solution of (3-bromo-5-nitrophenyl)methanol (5.00 g; 21.5 mmol; Aldlab Chemicals, LLC) in DCM (65 mL) and NMP (9 mL) at RT was added dropwise thionyl chloride (3.9 mL; 53.9 mmol). The mixture was allowed to react at RT overnight. Then, the mixture was poured into aqueous sodium bicarbonate solution/saturated aqueous sodium chloride solution/ice. The batch was stirred for one hour before it was extracted with ethyl acetate (2×). The combined organic phases were filtered using a Whatman filter and concentrated to give crude 1-bromo-3-(chloromethyl)-5-nitrobenzene (10.3 g), that was used without further purification.

The residue was re-dissolved in EtOH (85 mL) and sodium methanethiolate (4.04 g; 57.6 mmol) was added under stirring in three portions at 0° C. The cold bath was removed and the batch was stirred at room temperature overnight. Further sodium methanethiolate (2.03 g; 28.9 mmol) was added under stirring. After 4 hours, the batch was diluted with saturated aqueous sodium chloride solution and extracted with ethyl acetate (2×). The combined organic phases were dried (sodium sulfate), filtered and concentrated. The residue was purified by chromatography (hexane to hexane/ethyl acetate 4:1) to give the product (3.78 g; 7.94 mmol).

$^1$H NMR (400 MHz, CDCl$_3$, 300K) δ=8.35 (m, 1H), 8.32 (m, 1H), 8.19 (m, 1H), 7.99 (m, 1H), 7.69 (m, 1H), 7.53 (m, 1H), 3.73 (s, 2H), 3.70 (s, 2H), 2.04 (m, 6H).

Preparation of Intermediate 18.2:

3-Bromo-5-[(methylsulfanyl)methyl]aniline

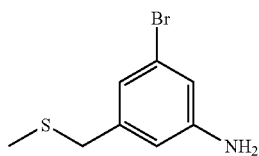

Hydrogen chloride (37.5% aqueous solution; 27.4 mL) was added dropwise over 4 hours to a refluxing mixture of bis {3-bromo-5-[(methylsulfanyl)methyl]phenyl}diazene oxide (3.65 g; 7.7 mmol) and iron powder (6.20 g; 110.9 mmol) in dioxane (60 mL). After cooling, the mixture was diluted with ethyl acetate and water. The mixture was basified using solid sodium bicarbonate and extracted with ethyl acetate (2×). The combined organic phases were washed with water, filtered using a Whatman filter and concentrated. The residue was purified by chromatography (hexane to hexane/ethyl acetate 1:1) to give the desired product (2.50 g; 10.77 mmol).

$^1$H NMR (400 MHz, CDCl$_3$, 300K) δ=6.82 (m, 1H), 6.71 (m, 1H), 6.56 (m 1H), 3.71 (br, 2H), 3.52 (s, 2H), 2.00 (s, 3H).

Preparation of Intermediate 18.3:

N-{3-Bromo-5-[(methylsulfanyl)methyl]phenyl}-4-(2,4-difluorophenyl)-5-fluoropyrimidin-2-amine

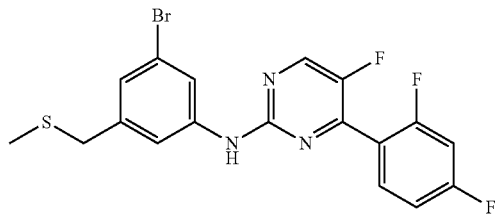 [SMILES: CSCc1cc(Br)cc(Nc2ncc(F)c(-c3ccc(F)cc3F)n2)c1]

Intermediate 18.3 was prepared under similar conditions as described in the preparation of Intermediate 1.4 using 3-bromo-5-[(methylsulfanyl)methyl]aniline (Intermediate 18.2) and 2-chloro-4-(2,4-difluorophenyl)-5-fluoropyrimidine (Intermediate 1.1).

$^1$H NMR (400 MHz, d$_6$-DMSO, 300 K) δ=10.08 (s, 1H), 8.73 (d, 1H), 7.93 (tr, 1H), 7.83 (trd, 1H), 7.70 (s, 1H), 7.55-7.44 (m, 1H), 7.34 (trd, 1H), 7.09 (s, 1H), 3.64 (s, 2H), 1.96 (s, 3H)

Preparation of Intermediate 18.4:

(rac)-[(3-Bromo-5-{[4-(2,4-difluorophenyl)-5-fluoropyrimidin-2-yl]amino}benzyl)(methyl)-λ$^4$-sulfanylidene]cyanamide

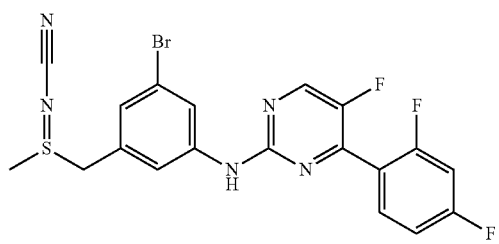 [SMILES: CS(Cc1cc(Br)cc(Nc2ncc(F)c(-c3ccc(F)cc3F)n2)c1)=NC#N]

Intermediate 18.4 was prepared under similar conditions as described in the preparation of Intermediate 1.5 using N-{3-bromo-5-[(methylsulfanyl)methyl]phenyl}-4-(2,4-difluorophenyl)-5-fluoropyrimidin-2-amine (Intermediate 18.3).

$^1$H NMR (400 MHz, d$_6$-DMSO, 300 K) δ=10.25 (s, 1H), 8.74 (d, 1H), 8.08 (tr, 1H), 7.85 (trd, 1H), 7.79 (s, 1H), 7.54-7.46 (m, 1H), 7.35 (trd, 1H), 7.21 (s, 1H), 4.49-4.21 (m, 2H), 2.85 (s, 3H).

Preparation of End Product:

Example 18 was prepared under similar conditions as described in the preparation of Example 10 (final step) using (rac)-[(3-bromo-5-{[4-(2,4-difluorophenyl)-5-fluoropyrimidin-2-yl]amino}benzyl)(methyl)-λ$^4$-sulfanylidene]cyanamide (Intermediate 18.4).

$^1$H NMR (400 MHz, d$_6$-DMSO, 300 K) δ=10.26 (s, 1H), 8.74 (d, 1H), 8.12 (tr, 1H), 7.88-7.79 (m, 2H), 7.55-7.44 (m, 1H), 7.33 (trd, 1H), 7.25 (tr, 1H), 5.05-4.92 (m, 2H), 3.39 (s, 3H).

Example 19

(rac)-N-{3-Bromo-5-[(S-methylsulfonimidoyl) methyl]phenyl}-4-(2,4-difluorophenyl)-5-fluoropyrimidin-2-amine

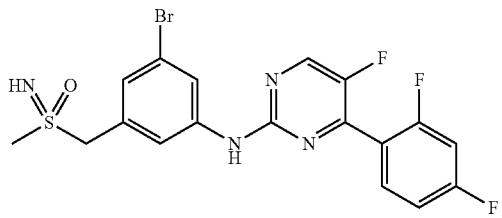

Example 19 was prepared under similar conditions as described in the preparation of Example 11 using (rac)-[(3-bromo-5-{[4-(2,4-difluorophenyl)-5-fluoropyrimidin-2-yl] amino}benzyl)(methyl)oxido-λ$^6$-sulfanylidene]cyanamide (Example 18). The batch was purified by chromatography (EtOAc/EtOH 9:1).

$^1$H NMR (400 MHz, d$_6$-DMSO, 300 K) δ=10.13 (s, 1H), 8.73 (d, 1H), 8.01 (tr, 1H), 7.83 (trd, 1H), 7.75 (d, 1H), 7.49 (ddd, 1H), 7.33 (trd, 1H), 7.22 (tr, 1H), 4.33 (s, 2H), 3.66 (s, 1H), 2.81 (s, 3H).

Example 20

(rac)-[(3-{[4-(2,4-Difluorophenyl)-5-fluoropyrimidin-2-yl]amino}-5-methoxybenzyl)(methyl)oxido-λ$^6$-sulfanylidene]cyanamide

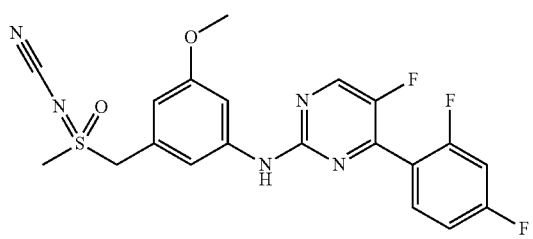 [SMILES: COc1cc(CS(C)(=O)=NC#N)cc(Nc2ncc(F)c(-c3ccc(F)cc3F)n2)c1]

Preparation of Intermediate 20.1:

1-Methoxy-3-[(methylsulfanyl)methyl]-5-nitrobenzene

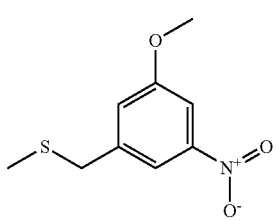

Intermediate 20.1 was prepared under similar conditions as described in the preparation of Intermediate 8.1 using 1-(chloromethyl)-3-methoxy-5-nitrobenzene (FCH Group, Ukraine).

$^1$H NMR (400 MHz, d$_6$-DMSO, 300 K) δ=7.79 (tr, 1H), 7.60 (tr, 1H), 7.39-7.29 (m, 1H), 3.87 (s, 3H), 3.80 (s, 2H), 1.96 (s, 3H).

Preparation of Intermediate 20.2:

3-Methoxy-5-[(methylsulfanyl)methyl]aniline

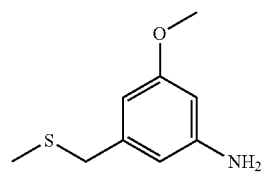

Intermediate 20.2 was prepared under similar conditions as described in the preparation of Intermediate 8.6 using 1-methoxy-3-[(methylsulfanyl)methyl]-5-nitrobenzene (Intermediate 20.1).

$^1$H NMR (400 MHz, d$_6$-DMSO, 300 K) δ=6.10 (tr, 1H), 6.05-5.96 (m, 2H), 5.07 (s, 2H), 3.63 (s, 3H), 3.48 (s, 2H), 1.95 (s, 3H).

Preparation of Intermediate 20.3:

4-(2,4-Difluorophenyl)-5-fluoro-N-{3-methoxy-5-[(methylsulfanyl)methyl]phenyl}pyrimidin-2-amine

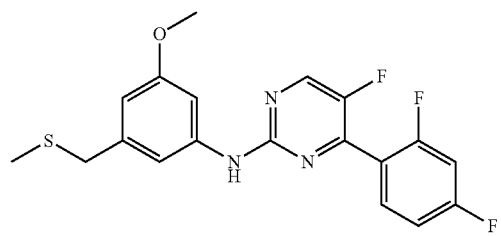 [SMILES: COc1cc(CSC)cc(Nc2ncc(F)c(-c3ccc(F)cc3F)n2)c1]

Intermediate 20.3 was prepared under similar conditions as described in the preparation of Intermediate 1.4 using 3-methoxy-5-[(methylsulfanyl)methyl]aniline (Intermediate 20.2) and 2-chloro-4-(2,4-difluorophenyl)-5-fluoropyrimidine (Intermediate 1.1).

$^1$H NMR (400 MHz, d$_6$-DMSO, 300 K) δ=9.89-9.82 (m, 1H), 8.68 (d, 1H), 7.88-7.79 (m, 1H), 7.54-7.45 (m, 1H), 7.45-7.29 (m, 3H), 7.26 (s, 1H), 6.50 (s, 1H), 3.71 (s, 4H), 3.61 (s, 2H), 1.97 (s, 3H).

Preparation of Intermediate 20.4:

(rac)-[(3-{[4-(2,4-Difluorophenyl)-5-fluoropyrimidin-2-yl]amino}-5-methoxybenzyl)(methyl)-λ⁴-sulfanylidene]cyanamide

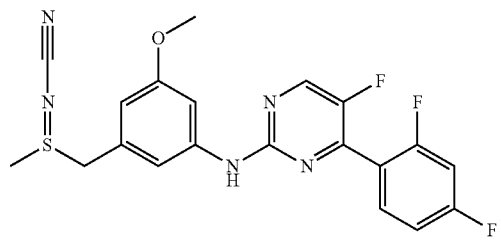 [SMILES: COc1cc(CS(C)=NC#N)cc(Nc2ncc(F)c(-c3ccc(F)cc3F)n2)c1]

Intermediate 20.4 was prepared under similar conditions as described in the preparation of Intermediate 1.5 using 4-(2,4-difluorophenyl)-5-fluoro-N-{3-methoxy-5-[(methylsulfanyl)methyl]phenyl}pyrimidin-2-amine (Intermediate 20.3).

$^1$H NMR (400 MHz, $d_6$-DMSO, 300 K) δ=10.05 (s, 1H), 8.71 (d, 1H), 7.86 (trd, 1H), 7.54-7.46 (m, 2H), 7.38-7.30 (m, 2H), 6.63 (dd, 1H), 4.45-4.16 (m, 2H), 3.74 (s, 3H), 2.84 (s, 3H).

Preparation of End Product:

Example 20 was prepared under similar conditions as described in the preparation of Example 10 (final step) using (rac)-[(3-{[4-(2,4-difluorophenyl)-5-fluoropyrimidin-2-yl]amino}-5-methoxybenzyl)(methyl)-λ⁴-sulfanylidene]cyanamide (Intermediate 20.4).

$^1$H NMR (400 MHz, $d_6$-DMSO, 300 K) δ=10.03 (s, 1H), 8.70 (d, 1H), 7.84 (trd, 1H), 7.56 (tr, 1H), 7.53-7.44 (m, 1H), 7.42 (s, 1H), 7.33 (trd, 1H), 6.71-6.66 (m, 1H), 4.98-4.84 (m, 2H), 3.75 (s, 3H), 3.36 (s, 3H).

Example 21

(rac)-4-(2,4-Difluorophenyl)-5-fluoro-N-{3-methoxy-5-[(S-methylsulfonimidoyl)methyl]phenyl}pyrimidin-2-amine

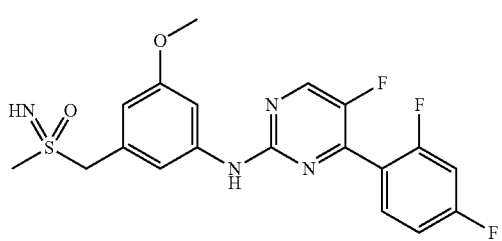 [SMILES: COc1cc(CS(C)(=N)=O)cc(Nc2ncc(F)c(-c3ccc(F)cc3F)n2)c1]

Example 21 was prepared under similar conditions as described in the preparation of Example 11 using (rac)-[(3-{[4-(2,4-Difluorophenyl)-5-fluoropyrimidin-2-yl]amino}-5-methoxybenzyl)(methyl)oxido-λ⁶-sulfanylidene]cyanamide (Example 20). The batch was purified by chromatography (EtOAc/EtOH 9:1).

$^1$H NMR (400 MHz, $d_6$-DMSO, 300 K) δ=9.91 (s, 1H), 8.68 (d, 1H), 7.84 (trd, 1H), 7.57-7.42 (m, 2H), 7.36-7.26 (m, 2H), 6.63 (dd, 1H), 4.33-4.21 (m, 2H), 3.73 (s, 3H), 3.56 (s, 1H), 2.80 (s, 3H).

Example 22

(rac)-{[3-{[4-(2,4-Difluorophenyl)-5-fluoropyrimidin-2-yl]amino}-5-(trifluoromethyl)benzyl](2-methoxyethyl)oxido-λ⁶-sulfanylidene}cyanamide

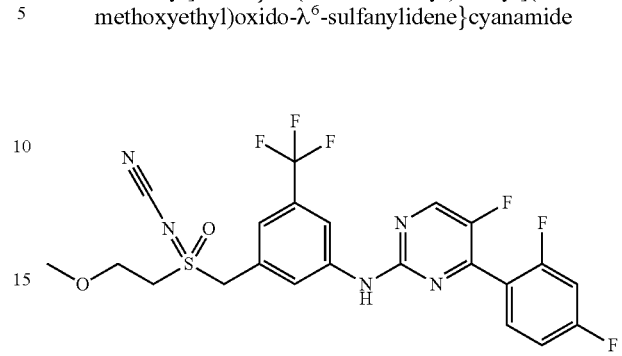

Preparation of Intermediate 22.1:

tert-Butyl-{3-[((2-methoxyethyl)sulfanyl)methyl]-5-(trifluoromethyl)phenyl}carbamate

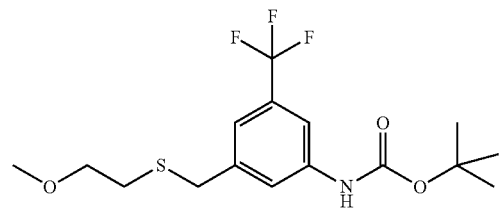 [SMILES: COCCSCc1cc(NC(=O)OC(C)(C)C)cc(C(F)(F)F)c1]

2-Methoxyethanethiole (0.103 g; 1.06 mmol) was added to a stirred solution of tert-butyl [3-(chloromethyl)-5-(trifluoromethyl)phenyl]carbamate (0.326 g; 1.0 mmol; Enamine) in methanol (6.5 mL). Cesium carbonate (0.657 g; 2.0 mmol) was added and the mixture was stirred for 3 hours at RT. The batch was diluted with saturated aqueous sodium chloride solution and extracted with ethyl acetate (2×). The combined organic phases were washed with water, dried (sodium sulfate), filtered and concentrated to give the desired product (0.398 g) that was used without further purification.

$^1$H NMR (400 MHz, CDCl$_3$, 300K) δ=7.59 (s, 1H), 7.50 (s, 1H), 6.58 (br. s., 1H), 3.76 (s, 2H), 3.53 (tr, 2H), 3.34 (s, 3H), 2.61 (tr, 2H), 1.52 (s, 9H).

Preparation of Intermediate 22.2:

3-[((2-Methoxyethyl)sulfanyl)methyl]-5-(trifluoromethyl)aniline

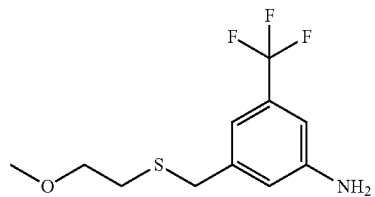 [SMILES: COCCSCc1cc(N)cc(C(F)(F)F)c1]

TFA (2 mL) was added to a stirred solution of tert-butyl {3-[((2-methoxyethyl)sulfanyl)methyl]-5-(tri-fluoromethyl)

phenyl}carbamate (398 mg; 0.98 mmol) in DCM (4 mL) at 0° C. The ice bath was removed and the mixture was stirred for 90 min at RT. The batch was concentrated and saturated aqueous sodium bicarbonate solution was added. The batch was extracted with ethyl acetate (2×). The combined organic phases were dried (sodium sulfate), filtered and concentrated to give the crude product (286 mg) that was used without further purification.

$^1$H NMR (400 MHz, CDCl$_3$, 300K) δ=6.94 (s, 1H), 6.81 (s, 1H), 6.77 (s, 1H), 3.70 (s, 2H), 3.52 (tr, 2H), 3.34 (s, 3H), 2.62 (tr, 2H).

Preparation of Intermediate 22.3:

4-(2,4-Difluorophenyl)-5-fluoro-N-{3-[((2-methoxyethyl)sulfanyl)methyl]-5-(trifluoromethyl)phenyl}pyrimidin-2-amine

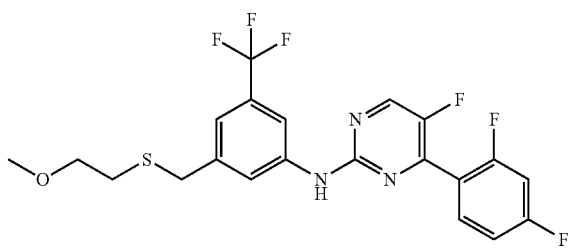 [SMILES: COCCSCc1cc(Nc2ncc(F)c(-c3ccc(F)cc3F)n2)cc(C(F)(F)F)c1]

A 4N solution of hydrogen chloride in dioxane (0.209 mL; 0.836 mmol) was added to a mixture of 2-chloro-4-(2,4-difluorophenyl)-5-fluoropyrimidine (204 mg; 0.833 mmol) and 3-[((2-methoxyethyl)sulfanyl)methyl]-5-(trifluoromethyl)aniline (257 mg; 0.833 mmol) in 1-butanol (0.75 mL) at room temperature. The batch was stirred at 140° C. for 20 hours. After cooling, the batch was concentrated and the residue was purified by chromatography (hexane/ethyl acetate 7% to 45%) to give the desired product (125 mg).

$^1$H NMR (400 MHz, CDCl$_3$, 300K) δ=8.41 (d, 1H), 8.00 (s, 1H), 7.70-7.79 (m, 2H), 7.33 (s, 1H), 7.25 (s, 1H), 7.03-7.10 (m, 1H), 6.94-7.01 (m, 1H), 3.77-3.83 (m, 2H), 3.54 (tr, 2H), 3.34 (s, 3H), 2.65 (tr, 2H).

Preparation of Intermediate 22.4:

(rac)-{[3-{[4-(2,4-Difluorophenyl)-5-fluoropyrimidin-2-yl]amino}-5-(trifluoromethyl)benzyl](2-methoxyethyl)-λ$^4$-sulfanylidene}cyanamide

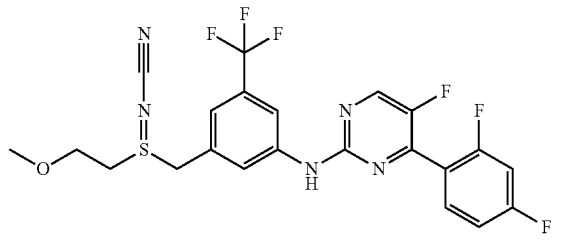 [SMILES: COCCS(Cc1cc(Nc2ncc(F)c(-c3ccc(F)cc3F)n2)cc(C(F)(F)F)c1)=NC#N]

1,3-Dibromo-5,5-dimethylhydantoin (42 mg; 0.145 mmol) was added to a stirred solution of 4-(2,4-difluorophenyl)-5-fluoro-N-{3-[((2-methoxyethylsulfanyl))methyl]-5-(trifluoromethyl)phenyl}pyrimidin-2-amine (109 mg; 0.207 mmol) and sodium hydrogencyanamide (19 mg; 0.29 mmol) in methanol (2.2 mL) at 0° C. The batch was stirred for 60 minutes at 0° C. before it was purified by chromatography (DCM/EtOH, 0-5%) to give the 80% pure product (23 mg).

$^1$H NMR (300 MHz, CDCl$_3$, 300K) δ=8.43 (d, 1H), 8.12 (s, 1H), 7.90 (s, 1H), 7.68-7.79 (m, 1H), 7.65 (s, 1H), 7.22 (s, 1H), 7.03-7.13 (m, 1H), 6.93-7.03 (m, 1H), 4.20-4.46 (m, 2H), 3.79-3.87 (m, 2H), 3.39-3.44 (m, 3H), 3.21-3.30 (m, 2H).

Preparation of End Product:

Potassium permanganate (11 mg; 0.069 mmol) was added to a stirred solution of (rac)-{[3-{[4-(2,4-difluorophenyl)-5-fluoropyrimidin-2-yl]amino}-5-(trifluoromethyl)benzyl](2-methoxyethyl)-λ$^4$-sulfanylidene}cyanamide (22 mg; 80% pure, 0.034 mmol) in acetone (0.5 mL) at room temperature. The batch was stirred at 40° C. for 30 minutes. The batch was concentrated and the residue was purified by chromatography (DCM/EtOH, 0-5%) to give the desired product (11 mg).

$^1$H NMR (300 MHz, CDCl$_3$, 300K) δ=8.44 (d, 1H), 8.19 (s, 1H), 7.95 (s, 1H), 7.68-7.78 (m, 1H), 7.56 (s, 1H), 7.37 (s, 1H), 7.08 (trd, 1H), 6.93-7.03 (m, 1H), 4.72 (s, 2H), 3.90 (tr, 2H), 3.49 (s, 3H), 3.31-3.43 (m, 2H).

Example 23

1-{[3-{[4-(2,4-Difluorophenyl)-5-fluoropyrimidin-2-yl]amino}-5-(trifluoromethyl)benzyl](methyl)oxido-λ$^6$-sulfanylidene}urea; enantiomer 1

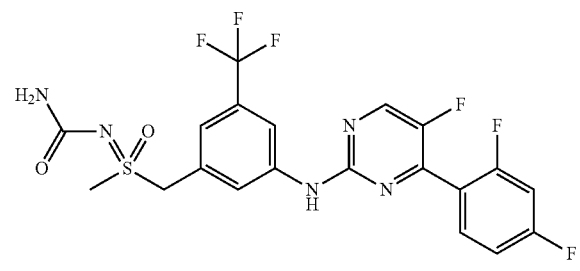 [SMILES: CS(=O)(Cc1cc(Nc2ncc(F)c(-c3ccc(F)cc3F)n2)cc(C(F)(F)F)c1)=NC(N)=O]

Example 23 was prepared under similar conditions as described in the preparation of Example 7 using {[3-{[4-(2,4-difluorophenyl)-5-fluoropyrimidin-2-yl]amino}-5-(trifluoromethyl)benzyl](methyl)oxido-λ$^6$-sulfanylidene}cyanamide, enantiomer 1.

Optical rotation index: 32.9°+/−0.14° (c=1.0000 g/100 mL DMSO; T=20° C.; wavelength: 589 nm)

Example 24

1-{[3-{[4-(2,4-Difluorophenyl)-5-fluoropyrimidin-2-yl]amino}-5-(trifluoromethyl)benzyl](methyl)oxido-λ$^6$-sulfanylidene}urea; enantiomer 2

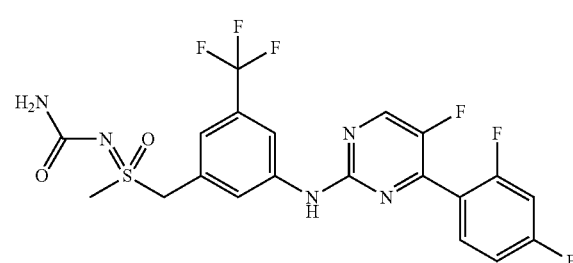

Example 24 was prepared under similar conditions as described in the preparation of Example 7 using {[3-{[4-(2,4-difluorophenyl)-5-fluoropyrimidin-2-yl]amino}-5-(trifluoromethyl)benzyl](methyl)oxido-$\lambda^6$-sulfanylidene}cyanamide, enantiomer 2.

Optical rotation index: −28.3°+/−0.09° (c=1.0000 g/100 mL DMSO; T=20° C.; wavelength: 589 nm)

Example 25

(rac)-N-[3-{[S-(2-Aminoethyl)sulfonimidoyl]methyl}-5-(trifluoromethyl)phenyl]-4-(2,4-difluorophenyl)-5-fluoropyrimidin-2-amine trifluoroacetate

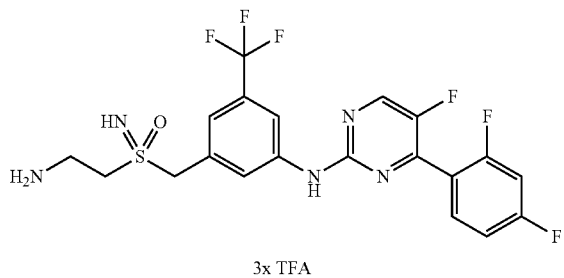 [SMILES: N=S(=O)(CCN)Cc1cc(Nc2ncc(F)c(-c3ccc(F)cc3F)n2)cc(C(F)(F)F)c1]

3x TFA

Preparation of Intermediate 25.1:

[3-{[4-(2,4-Difluorophenyl)-5-fluoropyrimidin-2-yl]amino}-5-(trifluoromethyl)phenyl]methanol

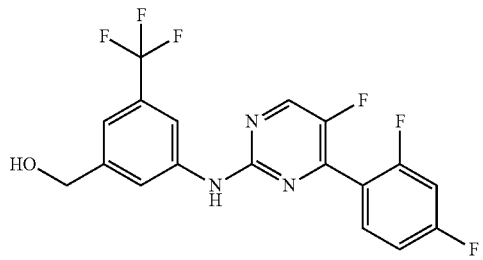 [SMILES: OCc1cc(Nc2ncc(F)c(-c3ccc(F)cc3F)n2)cc(C(F)(F)F)c1]

To a mixture of 2-chloro-4-(2,4-difluorophenyl)-5-fluoropyrimidine (1.00 g; 3.88 mmol) and [3-amino-5-(trifluoromethyl)phenyl]methanol (0.76 g; 3.88 mmol, [CAS-Nr. 537039-44-4]) in 1-butanol (2 mL) trifluoroacetic acid (0.3 mL; 3.88 mmol) was added and the mixture was stirred for 17 hours at 140° C. in a sealed tube. The batch was cooled and concentrated to give the crude product (2.23 g) which was purified by column chromatography on silica gel (10-75% EtOAc in hexane) to give the desired product (773 mg; 1.78 mmol).

$^1$H NMR (400 MHz, DMSO-d$_6$) δ [ppm]=10.22 (s, 1H), 8.75 (d, 1H), 8.16 (s, 1H), 7.92 (s, 1H), 7.80-7.88 (m, 1H), 7.45-7.53 (m, 1H), 7.33 (trd, 1H), 7.23 (s, 1H), 5.36 (tr, 1H), 4.55 (d, 2H).

Preparation of Intermediate 25.2:

N-[3-(chloromethyl)-5-(trifluoromethyl)phenyl]-4-(2,4-difluorophenyl)-5-fluoropyrimidin-2-amine hydrochloride (1:1)

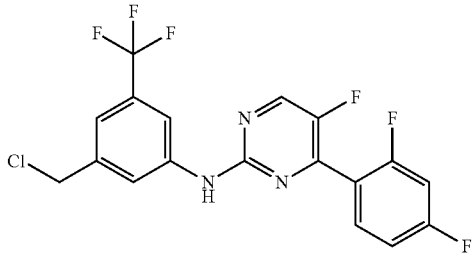 [SMILES: Fc1ccc(-c2nc(Nc3cc(CCl)cc(C(F)(F)F)c3)ncc2F)c(F)c1]

A suspension of [3-{[4-(2,4-difluorophenyl)-5-fluoropyrimidin-2-yl]amino}-5-(trifluoromethyl)phenyl]methanol (1.98 g; 4.6 mmol) in DCM (20 mL) at 0° C. was treated with thionyl chloride (0.68 ml, 9.2 mmol). The mixture was stirred for 7 hours at 0° C. to 25° C. The batch was concentrated to give the crude product (2.15 g) as the hydrochloride which was used without further purification.

$^1$H NMR (300 MHz, DMSO-d$_6$, 300K) δ [ppm]=10.35 (s, 1H), 8.77 (d, 1H), 8.22 (s, 1H), 8.07 (s, 1H), 7.77-7.89 (m, 1H), 7.43-7.56 (m, 1H), 7.36 (s, 1H), 7.33 (d, 1H), 4.81 (s, 2H).

Preparation of Intermediate 25.3:

tert-Butyl (2-{[3-{[4-(2,4-difluorophenyl)-5-fluoropyrimidin-2-yl]amino}-5-(trifluoromethyl)benzyl]sulfanyl}ethyl)carbamate

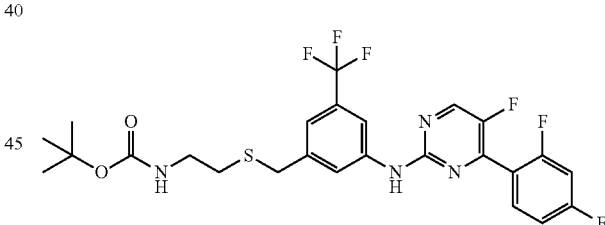

A suspension of N-[3-(chloromethyl)-5-(trifluoromethyl)phenyl]-4-(2,4-difluorophenyl)-5-fluoropyrimidin-2-amine hydrochloride (1:1) (2.11 g; 4.37 mmol) and cesium carbonate (2.65 g, 8 mmol) in ethanol (42 mL) at room temperature was treated with 2-(BOC-amino)ethanethiol (0.75 mL, 6.8 mmol). The batch was stirred for 2 hours and concentrated. The residue was dissolved with water (50 mL) and ethyl acetate (100 mL) and then extracted twice with ethyl acetate. The combined organic layers were washed with an aqueous solution of sodium chloride, dried over sodium sulfate and concentrated. The residue was purified by column chromatography on silica gel (hexane/ethyl acetate 7%-50% to give the desired product (2.36 g).

$^1$H NMR (400 MHz, CDCl$_3$, 300K) δ=10.23 (s, 1H) 8.75 (d, 1H) 8.10 (s, 1H) 7.96 (s, 1H) 7.84 (dd, 1H) 7.44-7.55 (m, 1H) 7.28-7.38 (m, 1H) 7.24 (s, 1H) 6.87-6.95 (m, 1H) 3.78 (s, 2H) 3.09 (d, 2H) 2.44 (s, 2H) 1.34 (s, 9H).

Preparation of Intermediate 25.4:

(rac)-tert-Butyl (2-{S-[3-{[4-(2,4-difluorophenyl)-5-fluoropyrimidin-2-yl]amino}-5-(trifluoromethyl)benzyl]-N-(trifluoroacetyl)sulfinimidoyl}ethyl)carbamate

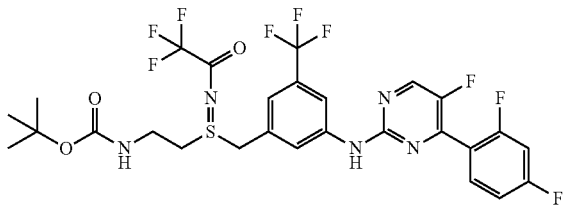 [SMILES: CC(C)(C)OC(=O)NCCS(Cc1cc(Nc2ncc(F)c(-c3ccc(F)cc3F)n2)cc(C(F)(F)F)c1)=NC(=O)C(F)(F)F]

A solution of sodium tert-butylate (345 mg, 3.48 mmol) in THF (7 mL) at 0° C. was treated with a solution of 2,2,2-trifluoracetamide (608 mg; 5.22 mmol) in THF (10 mL). Then, a solution of 1,3-dibromo-5,5-dimethylhydantoin (761 mg; 2.61 mmol) in THF (18 mL) was added and the resulting mixture was stirred for 10 min at 0° C. Then a solution of tert-butyl (2-{[3-{[4-(2,4-difluorophenyl)-5-fluoropyrimidin-2-yl]amino}-5-(trifluoromethyl)benzyl]sulfanyl}ethyl)carbamate (67% pure, 2.9 g; 3.48 mmol) in THF (36 mL) was added and the batch was stirred for 1 h at 10° C. The batch was diluted with toluene (8.0 mL) under cooling and an aqueous solution of sodium sulfite heptahydrate (877 mg; 2.66 mmol in 20.0 mL water) was added under cooling so that the temperature of the mixture remained below 15° C. After 10 minutes the batch was extracted three times with ethyl acetate. The combined organic layers were washed with saturated aqueous sodium chloride solution, dried over sodium sulfate, filtered and concentrated. The residue was purified by column chromatography on silica gel (EtOAc, 7% in hexane to 100% EtOAc) to give the pure product (1.57 g).

$^1$H NMR (300 MHz, CDCl$_3$, 300K) 6 [ppm]=10.35 (s, 1H) 8.74 (d, 1H) 8.20 (s, 1H) 8.01 (s, 1H) 7.84 (dd, 1H) 7.48 (ddd, 1H) 7.29-7.37 (m, 1H) 7.20 (s, 1H) 7.17 (br. s., 1H) 4.75 (d, 1H) 4.50 (d, 1H) 3.32-3.42 (m, 1H) 3.15-3.29 (m, 2H) 3.07 (d, 1H) 1.35 (s, 9H).

Preparation of Intermediate 25.5:

(rac)-tert-Butyl (2-{S-[3-{[4-(2,4-difluorophenyl)-5-fluoropyrimidin-2-yl]amino}-5-(trifluoromethyl)benzyl]-N-(trifluoroacetyl)sulfonimidoyl}ethyl)carbamate

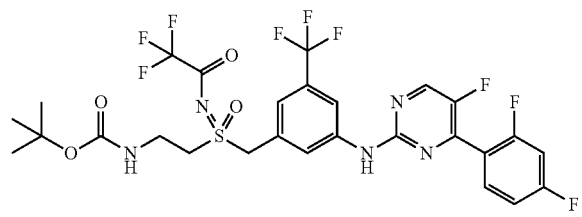 [SMILES: CC(C)(C)OC(=O)NCCS(=O)(Cc1cc(Nc2ncc(F)c(-c3ccc(F)cc3F)n2)cc(C(F)(F)F)c1)=NC(=O)C(F)(F)F]

Potassium permanganate (freshly ground, 2.6 g; 16.4 mmol) was added in four portions to a stirred solution of (rac)-tert-butyl (2-{S-[3-{[4-(2,4-difluorophenyl)-5-fluoropyrimidin-2-yl]amino}-5-(trifluoromethyl)benzyl]-N-(trifluoroacetyl)sulfonimidoyl}ethyl)carbamate (1.57 g; 2.2 mmol) in acetone (32 mL) at room temperature. The batch was stirred at 40° C. for 21 h, concentrated and the residue was purified by column chromatography on silica gel (EtOH 7-100 vol % in hexane) to give the desired product (761 mg).

$^1$H NMR (300 MHz, DMSO-d$_6$, 300K) δ [ppm]=10.42 (s, 1H), 8.74 (d, 1H), 8.29 (s, 1H), 8.08 (s, 1H), 7.84 (m, 1H), 7.42-7.56 (m, 1H), 7.32 (s, 2H), 7.11 (br. s., 1H), 5.13-5.32 (m, 2H), 3.69-3.83 (m, 2H), 3.47 (m, 2H), 1.35 (s, 9H).

Preparation of Intermediate 25.6:

(rac)-tert-Butyl (2-{S-[3-{[4-(2,4-difluorophenyl)-5-fluoropyrimidin-2-yl]amino}-5-(trifluoromethyl)benzyl]sulfonimidoyl}ethyl)carbamate

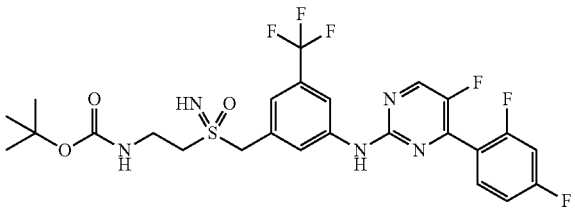 [SMILES: CC(C)(C)OC(=O)NCCS(=N)(=O)Cc1cc(Nc2ncc(F)c(-c3ccc(F)cc3F)n2)cc(C(F)(F)F)c1]

A solution of (rac)-tert-butyl (2-{S-[3-{[4-(2,4-difluorophenyl)-5-fluoropyrimidin-2-yl]amino}-5-(trifluoromethyl)benzyl]-N-(trifluoroacetyl)sulfinimidoyl}ethyl)carbamate (760 mg; 1.05 mmol) in methanol (7.6 mL) at room temperature was treated with potassium carbonate (437 mg, 3.16 mmol). The batch was stirred for 0.5 h, diluted with water (80 mL), extracted three times (3×) with dichloromethane, dried over sodium sulfate and evaporated under reduced pressure to give the desired product (576 mg).

$^1$H NMR (300 MHz, DMSO-d$_6$, 300K) δ [ppm]=10.29 (s, 1H), 8.74 (d, 1H), 8.21 (s, 1H), 7.99 (s, 1H), 7.79-7.90 (m, 1H), 7.44-7.55 (m, 1H), 7.37 (s, 1H), 7.27-7.34 (m, 1H), 6.90-7.00 (m, 1H), 4.37-4.51 (m, 2H), 3.85 (s, 1H), 3.37-3.43 (m, 2H), 3.05 (d, 2H), 1.35 (s, 9H).

Preparation of End Product:

A solution of (rac)-tert-butyl (2-{S-[3-{[4-(2,4-difluorophenyl)-5-fluoropyrimidin-2-yl]amino}-5-(trifluoromethyl)benzyl]sulfonimidoyl}ethyl)carbamate (50 mg, 0.085 mmol) in dichloromethane (0.5 mL) at room temperature was treated with trifluoroacetic acid (0.25 mL). The batch was stirred at 25° C. for 2 h, concentrated under reduced pressure, the residue was treated with sodium bicarbonate solution (5 mL extracted twice (2×) with dichloromethane (7 mL, incl. ethanol (0.5 mL)), the combined organic layers were dried over sodium sulfate and concentrated to give the desired product (25 mg).

$^1$H NMR (300 MHz, DMSO-d$_6$, 300K) δ [ppm]=10.34 (s, 1H), 8.76 (d, 1H), 8.26 (s, 1H), 7.98 (s, 1H), 7.67-7.95 (m, 3H), 7.45-7.56 (m, 1H), 7.39 (s, 1H), 7.25-7.36 (m, 1H), 4.59 (m, 2H), 3.50 (s, 1H), 3.23 (m, 4H).

Examples 26 and 27

Enantiomers of N-[3-{[S-(2-Aminoethyl)sulfonimidoyl]methyl}-5-(trifluoromethyl)phenyl]-4-(2,4-difluorophenyl)-5-fluoropyrimidin-2-amine

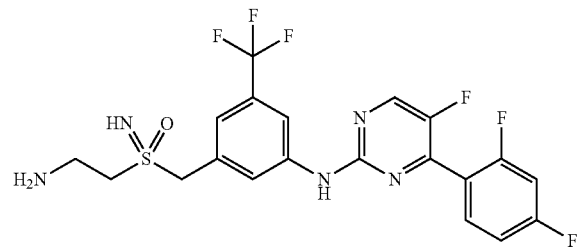 [SMILES: N=S(=O)(CCN)Cc1cc(Nc2ncc(F)c(-c3ccc(F)cc3F)n2)cc(C(F)(F)F)c1]

(rac)-tert-Butyl (2-{S-[3-{[4-(2,4-difluorophenyl)-5-fluoropyrimidin-2-yl]amino}-5-(trifluoromethyl)benzyl]sulfonimidoyl}ethyl)carbamate (Intermediate 25.6) was separated into the enantiomers by chiral preparative HPLC.

| | | | |
|---|---|---|---|
| System: | Agilent: Prep 1200, 2xPrep Pump, DLA, MWD, Prep FC, | | |
| Column: | Chiralpak IC 5 μm 250 × 20 mm | | |
| Solvent: | Hexan/2-Propanol 70:30 (v/v) | | |
| Flow: | 31 mL/min | | |
| Temperature: | RT | | |
| Mobile phase: | 486 mg/5 mL MeOH + 0.1 mL DMSO | | |
| Injection: | 5 × 1 mL | | |
| Detection: | UV 254 nm | | |

| | Rt in min | purity in % | amount [mg] | optical rotation index |
|---|---|---|---|---|
| Enantiomer 1 of Intermediate 25.6 | 3.24-4.82 | 98.76 | 190 | $[\alpha]_D^{20}$ = +12.1° +/− 0.25° (c = 1.0000 g/100 mL DMSO; T = 20° C.; wavelength: 589 nm). |
| Enantiomer 2 of Intermediate 25.6 | 5.86-8.25 | 97.43 | 190 | $[a]_D^{20}$ = −14.0° +/− 0.35° (c = 1.0000 g/100 mL DMSO; T = 20° C.; wavelength: 589 nm). |

Both of these enantiomers were transformed by deprotection with trifluoroacetic acid as described above in example 25 into the desired enantiopure compounds.

Example 26

Enantiomer 1: optical rotation index: $[\alpha]_D^{20}$=+10.4°+/−0.22° (c=1.0000 g/100 mL DMSO; T=20° C.; wavelength: 589 nm).

Example 27

Enantiomer 2: optical rotation index: $[\alpha]_D^{20}$=−7.3°+/−0.37° (c=1.0000 g/100 mL DMSO; T=20° C.; wavelength: 589 nm).

Example 28

(rac)-{[3-{[4-(2,4-Difluorophenyl)-5-fluoropyrimidin-2-yl]amino}-5-(pentafluoro-λ$^6$-sulfanyl)benzyl](methyl)oxido-λ$^6$-sulfanylidene}cyanamide

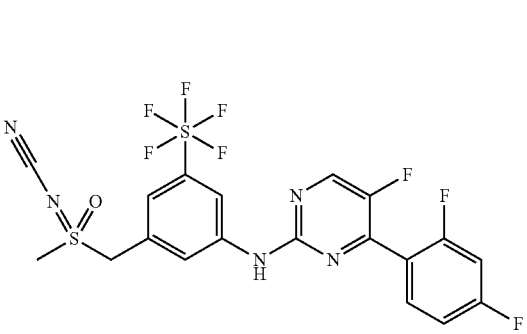 [SMILES: CS(=O)(Cc1cc(Nc2ncc(F)c(-c3ccc(F)cc3F)n2)cc(S(F)(F)(F)(F)F)c1)=NC#N]

Preparation of Intermediate 28.1:

[3-{[4-(2,4-Difluorophenyl)-5-fluoropyrimidin-2-yl]amino}-5-(pentafluoro-λ$^6$-sulfanyl)phenyl]methanol

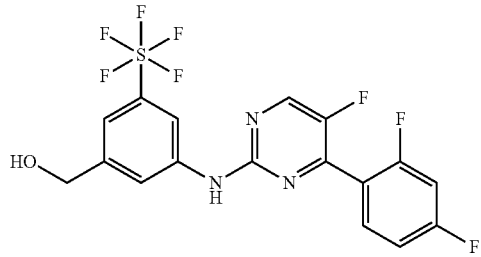 [SMILES: OCc1cc(Nc2ncc(F)c(-c3ccc(F)cc3F)n2)cc(S(F)(F)(F)(F)F)c1]

To a mixture of 2-chloro-4-(2,4-difluorophenyl)-5-fluoropyrimidin (10.0 g; 38.8 mmol) and [3-amino-5-(pentafluoro-λ$^6$-sulfanyl)phenyl]methanol ([CAS-Nr. 1427316-37-7] 10.0 g; 39.3 mmol) in 1-butanol (20 mL) trifluoroacetic acid (3.0 mL; 38.6 mmol) was added and the mixture was stirred for 17 hours at 140° C. in a sealed tube. The batch was cooled and concentrated to give the crude product (25.3 g) which was purified by column chromatography on silica gel (hexane/EtOAc, 10-80%) to give the desired product (10.25 g).

$^1$H NMR (400 MHz, DMSO-$d_6$) δ [ppm]=10.30 (s, 1H), 8.76 (d, 1H), 8.41 (s, 1H), 7.83-7.89 (m, 1H), 7.75-7.83 (m, 1H), 7.45-7.56 (m, 1H), 7.38 (s, 1H), 7.26-7.35 (m, 1H), 5.46 (br. s., 1H), 4.54 (d, 2H).

Preparation of Intermediate 28.2:

N-[3-(Chloromethyl)-5-(pentafluoro-$\lambda^6$-sulfanyl)phenyl]-4-(2,4-difluorophenyl)-5-fluoropyrimidin-2-amine

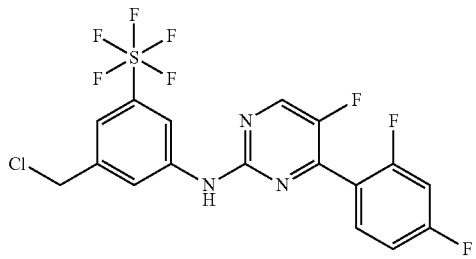 [SMILES: Fc1ccc(-c2nc(Nc3cc(CCl)cc(S(F)(F)(F)(F)F)c3)ncc2F)c(F)c1]

A suspension of [3-{[4-(2,4-difluorophenyl)-5-fluoropyrimidin-2-yl]amino}-5-(pentafluoro-26-sulfanyl)phenyl]methanol (11.42 g; 23.7 mmol) in DCM (60 mL) at 0° C. was treated with thionyl chloride (14 mL, 119 mmol). The mixture was stirred for 3 hours at 0 to 25° C. The batch was concentrated to give the crude product (12.49 g) which was used without further purification.

$^1$H NMR (300 MHz, DMSO-$d_6$, 300K) δ [ppm]=10.40 (s, 1H), 8.78 (d, 1H), 8.46 (s, 1H), 8.04 (s, 1H), 7.76-7.89 (m, 1H), 7.53-7.58 (m, 1H), 7.44-7.52 (m, 1H), 7.27-7.38 (m, 1H), 4.84 (m, 2H).

Preparation of Intermediate 28.3:

4-(2,4-Difluorophenyl)-5-fluoro-N-{3-[(methylsulfanyl)methyl]-5-(pentafluoro-$\lambda^6$-sulfanyl)phenyl}pyrimidin-2-amine

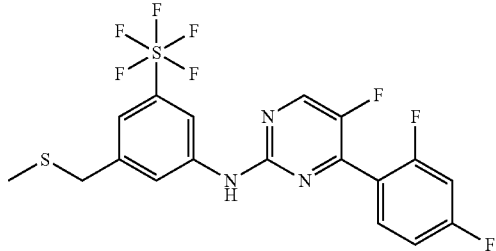 [SMILES: CSCc1cc(Nc2ncc(F)c(-c3ccc(F)cc3F)n2)cc(S(F)(F)(F)(F)F)c1]

Sodium methanethiolate (3.23 g; 41.4 mmol) was added in three portions to a stirred solution of N-[3-(chloromethyl)-5-(pentafluoro-$\lambda^6$-sulfanyl)phenyl]-4-(2,4-difluorophenyl)-5-fluoropyrimidin-2-amine (11.4 g; 21.6 mmol) in ethanol (100 mL) at −15° C. The cold bath was removed and the batch was stirred at room temperature for 7 hours. The batch was diluted with saturated aqueous sodium chloride solution and extracted twice with ethyl acetate. The combined organic layers were washed with water, dried (sodium sulfate), filtered and concentrated to give the desired product (11.38 g) that was used without further purification.

$^1$H NMR (400 MHz, CDCl$_3$, 300K) δ [ppm]=8.45 (s, 1H), 8.29 (s, 1H), 7.71-7.84 (m, 1H), 7.64 (s, 1H), 7.37 (br. s., 2H), 7.09 (t, 1H), 6.91-7.05 (m, 1H), 3.73 (s, 2H), 2.05 (s, 3H).

Preparation of Intermediate 28.4:

(rac)-{[3-{[4-(2,4-Difluorophenyl)-5-fluoropyrimidin-2-yl]amino}-5-(pentafluoro-$\lambda^6$-sulfanyl)benzyl](methyl)-$\lambda^4$-sulfanylidene}cyanamide

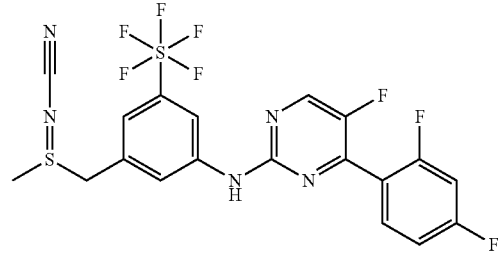 [SMILES: CS(Cc1cc(Nc2ncc(F)c(-c3ccc(F)cc3F)n2)cc(S(F)(F)(F)(F)F)c1)=NC#N]

1,3-Dibromo-5,5-dimethylhydantoin (3.32 g; 11.4 mmol) was added to a stirred solution of 4-(2,4-difluorophenyl)-5-fluoro-N-{3-[(methylsulfanyl)methyl]-5-(pentafluoro-$\lambda^6$-sulfanyl)phenyl}pyrimidin-2-amine (7.47 g; 15.2 mmol) and sodium hydrogencyanamid (1.388 g; 21.2 mmol) in methanol (150 mL) at 0° C. The batch was stirred for 60 minutes at 0° C. and then concentrated before it was diluted with an aqueous solution of sodium thiosulfate and water. The batch was extracted three times with DCM. The combined organic layers were dried (sodium sulfate), filtered and concentrated to give the desired product to give the 80% pure product (8.7 g).

$^1$H NMR (300 MHz, CDCl$_3$, 300K) δ [ppm]=8.45 (d, 1H), 8.36-8.43 (m, 1H), 7.84 (s, 1H), 7.67-7.77 (m, 1H), 7.63 (d, 1H), 7.35 (s, 1H), 7.05-7.12 (m, 1H), 6.95-7.04 (m, 1H), 4.43 (d, 1H), 4.20 (d, 1H), 2.83 (s, 3H).

Preparation of End Product:

Potassium permanganate (freshly ground, 4.2 g; 26.1 mmol) was added to a stirred solution of (rac)-{[3-{[4-(2,4-difluorophenyl)-5-fluoropyrimidin-2-yl]amino}-5-(pentafluoro-$\lambda^6$-sulfanyl)benzyl](methyl)-$\lambda^4$-sulfanylidene}cyanamide (8.71 g; 13 mmol) in acetone (175 mL) at room temperature. The batch was stirred at 40° C. for 1 h, concentrated and the residue was purified by column chromatography on silica gel (EtOH 0-6% in DCM) to give the desired product (5.27 g).

$^1$H NMR (300 MHz, CDCl$_3$, 300K) δ [ppm]=8.45 (d, 1H), 8.40 (s, 1H), 7.96 (s, 1H), 7.67-7.78 (m, 1H), 7.62 (s, 1H), 7.41 (s, 1H), 7.08 (trd, 1H), 6.99 (ddd, 1H), 4.56-4.73 (m, 2H), 3.12 (s, 3H).

Examples 29 and 30

Enantiomers of {[3-{[4-(2,4-Difluorophenyl)-5-fluoropyrimidin-2-yl]amino}-5-(pentafluoro-λ⁶-sulfanyl)benzyl](methyl)oxido-λ⁶-sulfanylidene}cyanamide

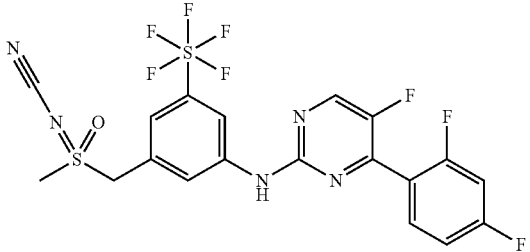 [SMILES: CS(=O)(Cc1cc(Nc2ncc(F)c(-c3ccc(F)cc3F)n2)cc(S(F)(F)(F)(F)F)c1)=NC#N]

(rac)-{[3-{[4-(2,4-difluorophenyl)-5-fluoropyrimidin-2-yl]amino}-5-(pentafluoro-λ⁶-sulfanyl)benzyl](methyl)oxido-λ⁶-sulfanylidene}cyanamide was separated into the enantiomers by chiral preparative HPLC:

| System: | Sepiatec: Prep SFC100, |
|---|---|
| Column: | Chiralpak ID 5 µm 250 × 30 mm |
| Solvent: | CO₂/2-Propanol 85/15 |
| Flow: | 100 mL/min |
| Pressure): | 150 bar |
| Temperature: | 40° C. |
| Mobile phase: | 5220 mg/20 mL Acetone/DMF 3:1 |
| Injection: | 40 × 0.5 mL |
| Detection: | UV 254 nm |

| | Rt in min | purity in % | amount in g |
|---|---|---|---|
| Example 29 Enantiomer 1 | 5.5-6.5 | 97.80 | 1.77 |
| Example 30 Enantiomer 2 | 7.0-8.5 | 99.41 | 1.70 |

Examples 31 and 32

Enantiomers of 4-(2,4-Difluorophenyl)-5-fluoro-N-{3-[(S-methylsulfonimidoyl)methyl]-5-(pentafluoro-λ⁶-sulfanyl)phenyl}pyrimidin-2-amine

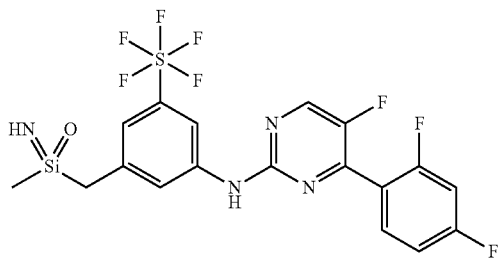

Examples 31 and 32 were prepared under similar conditions as described in the preparation of Example 4 using the single enantiomers of {[3-{[4-(2,4-difluorophenyl)-5-fluoropyrimidin-2-yl]amino}-5-(pentafluoro-λ⁶-sulfanyl)benzyl](methyl)oxido-λ⁶-sulfanylidene}cyanamide (examples 29 and 30)

$^1$H NMR (DMSO-d$_6$) δ [ppm]=10.34 (s, 1H), 8.74 (d, 1H), 8.43-8.49 (m, 1H), 7.96 (s, 1H), 7.78-7.89 (m, 1H), 7.56 (s, 1H), 7.43-7.50 (m, 1H), 7.27-7.35 (m, 1H), 4.47 (s, 2H), 3.70 (s, 1H), 2.83 (s, 3H).

Example 31 optical rotation index: $[α]_D^{20}$=−11.7°+/−0.100 (c=1.0000 g/100 mL DMSO; T=20° C.; wavelength: 589 nm)

Example 32 optical rotation index: $[α]_D^{20}$=+13.3°+/−0.110 (c=1.0000 g/100 mL DMSO; T=20° C.; wavelength: 589 nm)

Examples 33 and 34

Enantiomers of 1-{[3-{[4-(2,4-difluorophenyl)-5-fluoropyrimidin-2-yl]amino}-5-(pentafluoro-λ⁶-sulfanyl)benzyl](methyl)oxido-λ⁶-sulfanylidene}urea

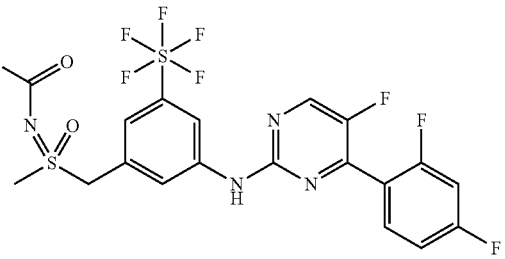

Examples 33 and 34 were prepared under similar conditions as described in the preparation of Example 7 using the single enantiomers of {[3-{[4-(2,4-difluorophenyl)-5-fluoropyrimidin-2-yl]amino}-5-(pentafluoro-λ⁶-sulfanyl)benzyl](methyl)oxido-λ⁶-sulfanylidene}cyanamide (examples 29 and 30).

$^1$H NMR (DMSO-d$_6$) δ [ppm]=10.36 (s, 1H), 8.75 (d, 1H), 8.46 (s, 1H), 8.01-8.07 (m, 1H), 7.78-7.87 (m, 1H), 7.56-7.61 (m, 1H), 7.41-7.51 (m, 1H), 7.27-7.37 (m, 1H), 5.97-6.32 (m, 2H), 4.93 (s, 2H), 3.05 (s, 3H)

Examples 35 and 36

Enantiomers of [(3-{[4-(2,4-difluorophenyl)-5-fluoro-pyrimidin-2-yl]amino}-5-methylbenzyl)-(methyl)oxido-λ⁶-sulfanylidene]cyanamide

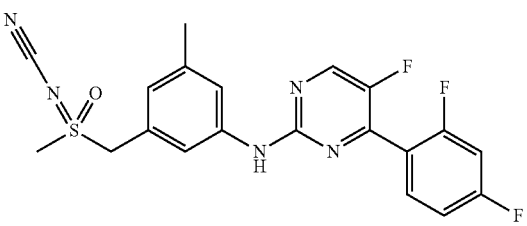 [SMILES: Cc1cc(CS(C)(=O)=NC#N)cc(Nc2ncc(F)c(-c3ccc(F)cc3F)n2)c1]

(rac)-[(3-{[4-(2,4-Difluorophenyl)-5-fluoro-pyrimidin-2-yl]amino}-5-methylbenzyl)-(methyl)oxido-λ⁶-sulfanylidene]cyanamide (Example 16) was separated into the enantiomers by chiral preparative HPLC.

| | | |
|---|---|---|
| System: | Agilent: Prep 1200, 2× Prep Pump, DLA, MWD, Prep FC | |
| Column: | Chiralpak IC 5 μm 250 × 30 mm | |
| Solvent: | Hexane/Ethanol/Diethylamine 70:30:0.1 (v/v/v) | |
| Flow: | 50 mL/min | |
| Temperature: | RT | |
| Solution: | 205 mg/6 mL DCM/MeOH/DMSO | |
| Injection: | 10 × 0.6 mL | |
| Detection: | UV 280 nm | |

| | Retention time in min | purity in % |
|---|---|---|
| Example 35 Enantiomer 1 | 5.4-9.0 | >99.9 |
| Example 36 Enantiomer 2 | 9.0-10.7 | 97.7 |

Examples 37 and 38

Enantiomers of 4-(2,4-Difluorophenyl)-5-fluoro-N-{3-methyl-5-[(S-methylsulfonimidoyl)-methyl]-phenyl}pyrimidin-2-amine

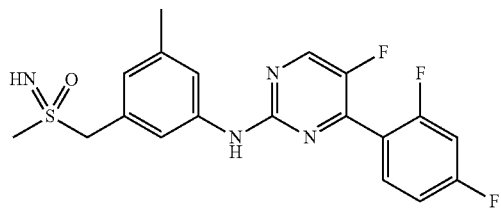 [SMILES: Cc1cc(CS(C)(=N)=O)cc(Nc2ncc(F)c(-c3ccc(F)cc3F)n2)c1]

(rac)-4-(2,4-Difluorophenyl)-5-fluoro-N-{3-methyl-5-[(S-methylsulfonimidoyl)-methyl]-phenyl}pyrimidin-2-amine (Example 17) was separated into the enantiomers by chiral preparative HPLC.

| | | |
|---|---|---|
| System: | Agilent: Prep 1200, 2× Prep Pump, DLA, MWD, Prep FC | |
| Column: | Chiralpak IC 5 μm 250 × 30 mm | |
| Solvent: | Hexane / Ethanol / Diethylamine 70:30:0.1 (v/v/v) | |
| Flow: | 25 mL/min | |
| Temperature: | RT | |
| Solution: | 270 mg/6 mL DCM/MeOH | |
| Injection: | 10 × 0.6 mL | |
| Detection: | UV 280 nm | |

| | Retention time in min | purity in % |
|---|---|---|
| Example 37 Enantiomer 1 | 16.4-18.5 min | >99.9% |
| Example 38 Enantiomer 2 | 19.2-21.8 min | 99.3% |

Examples 39 and 40

Enantiomers of [(3-Bromo-5-{[4-(2,4-difluorophenyl)-5-fluoropyrimidin-2-yl]amino}benzyl)-(methyl)-oxido-$\lambda^6$-sulfanylidene]cyanamide

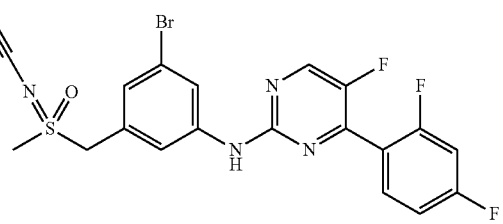

(rac)-[(3-Bromo-5-{[4-(2,4-difluorophenyl)-5-fluoropyrimidin-2-yl]amino}benzyl)(methyl)-oxido-$\lambda^6$-sulfanylidene]cyanamide (Example 18) was separated into the enantiomers by chiral preparative HPLC.

| | | |
|---|---|---|
| System: | Agilent: Prep 1200, 2xPrep Pump, DLA, MWD, Prep FC | |
| Column: | Chiralpak IA 5 μm 250 × 30 mm | |
| Solvent: | Hexane/2-Propanol/Diethylamine 70:30:0.1 (v/v/v) | |
| Flow: | 50 mL/min | |
| Temperature: | RT | |
| Solution: | 101 mg/6 mL DCM/MeOH | |
| Injection: | 2 × 3.0 mL | |
| Detection: | UV 280 nm | |

| | Retention time in min | purity in % |
|---|---|---|
| Example 39 Enantiomer 1 | 9.9-13.9 min | >99.9% |
| Example 40 Enantiomer 2 | 13.9-18.7 min | 96.1% |

Examples 41 and 42

Enantiomers of N-{3-Bromo-5-[(S-methylsulfonimidoyl)methyl]phenyl}-4-(2,4-difluorophenyl)-5-fluoropyrimidin-2-amine

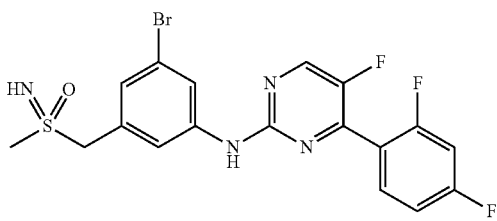

(rac)-[(3-Bromo-5-{[4-(2,4-difluorophenyl)-5-fluoropyrimidin-2-yl]amino}benzyl)(methyl)-oxido-$\lambda^6$-sulfanylidene]cyanamide (Example 19) was separated into the enantiomers by chiral preparative HPLC.

| System: | Agilent: Prep 1200, 2× Prep Pump, DLA, MWD, Prep FC |
|---|---|
| Column: | Chiralpak IA 5 μm 250 × 30 mm |
| Solvent: | Hexane/Ethanol/Diethylamine 70:30:0.1 (v/v/v) |
| Flow: | 20 mL/min |
| Temperature: | RT |
| Solution: | 188 mg/2 mL DCM/MeOH 1:1 |
| Injection: | 6 × 0.33 mL |
| Detection: | UV 254 nm |

-continued

| | Retention time in min | purity in % |
|---|---|---|
| Example 41 Enantiomer 1 | 7.5-11.0 min | >99% |
| Example 42 Enantiomer 2 | 12.5-19.0 min | 98.0% |

The following Table 1 provides an overview on the compounds described in the example section:

TABLE 1

| Example No. | Structure | Name of compound |
|---|---|---|
| 1 | 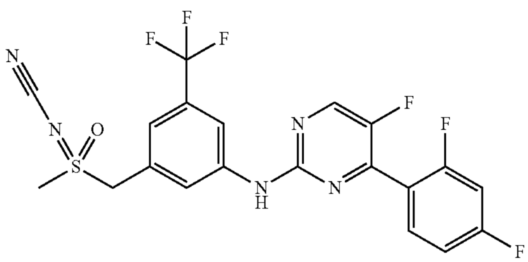 [SMILES: CS(=O)(Cc1cc(Nc2ncc(F)c(-c3ccc(F)cc3F)n2)cc(C(F)(F)F)c1)=NC#N] | (rac)-{[3-{[4-(2,4-Difluorophenyl)-5-fluoropyrimidin-2-yl]amino}-5-(trifluoromethyl)benzyl](methyl)oxido-$\lambda^6$-sulfanylidene}cyanamide |
| 2 | 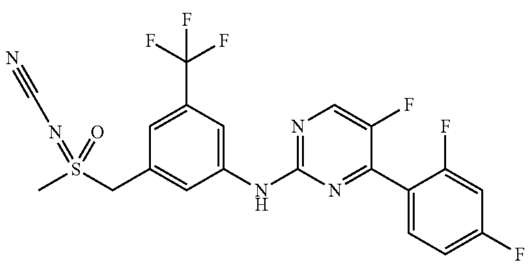 [SMILES: CS(=O)(Cc1cc(Nc2ncc(F)c(-c3ccc(F)cc3F)n2)cc(C(F)(F)F)c1)=NC#N] | {[3-{[4-(2,4-Difluorophenyl)-5-fluoropyrimidin-2-yl]amino}-5-(trifluoromethyl)benzyl](methyl)oxido-$\lambda^6$-sulfanylidene}cyanamide, enantiomer 1 |
| 3 | 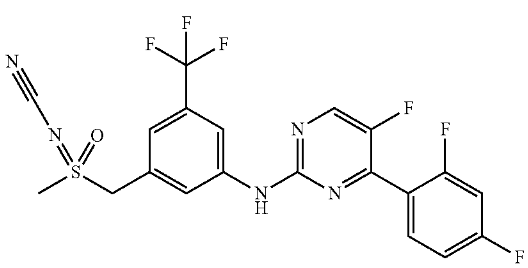 [SMILES: CS(=O)(Cc1cc(Nc2ncc(F)c(-c3ccc(F)cc3F)n2)cc(C(F)(F)F)c1)=NC#N] | {[3-{[4-(2,4-Difluorophenyl)-5-fluoropyrimidin-2-yl]amino}-5-(trifluoromethyl)benzyl](methyl)oxido-$\lambda^6$-sulfanylidene}cyanamide, enantiomer 2 |
| 4 | 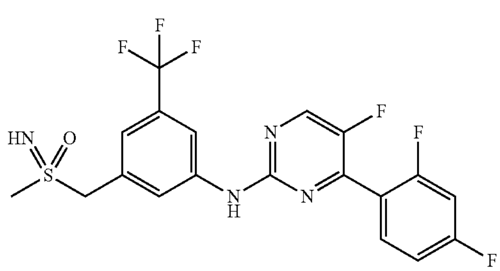 [SMILES: CS(=N)(=O)Cc1cc(Nc2ncc(F)c(-c3ccc(F)cc3F)n2)cc(C(F)(F)F)c1] | (rac)-4-(2,4-Difluorophenyl)-5-fluoro-N-{3-[(S-methylsulfonimidoyl)methyl]-5-(trifluoromethyl)phenyl}pyrimidin-2-amine |

TABLE 1-continued

| Example No. | Structure | Name of compound |
|---|---|---|
| 5 | 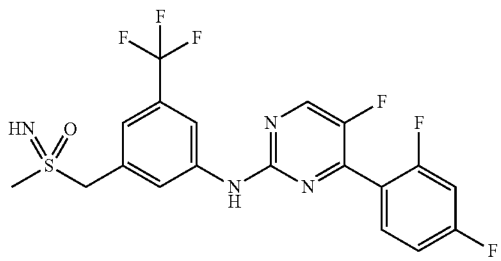 [SMILES: CS(=N)(=O)Cc1cc(Nc2ncc(F)c(-c3ccc(F)cc3F)n2)cc(C(F)(F)F)c1] | 4-(2,4-Difluorophenyl)-5-fluoro-N-{3-[(S-methylsulfonimidoyl)methyl]-5-(trifluoromethyl)phenyl}pyrimidin-2-amine, enantiomer 1 |
| 6 | 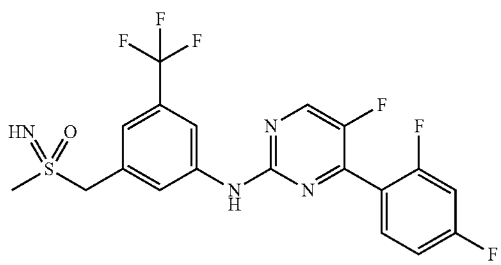 [SMILES: CS(=N)(=O)Cc1cc(Nc2ncc(F)c(-c3ccc(F)cc3F)n2)cc(C(F)(F)F)c1] | 4-(2,4-Difluorophenyl)-5-fluoro-N-{3-[(S-methylsulfonimidoyl)methyl]-5-(trifluoromethyl)phenyl}pyrimidin-2-amine, enantiomer 2 |
| 7 | 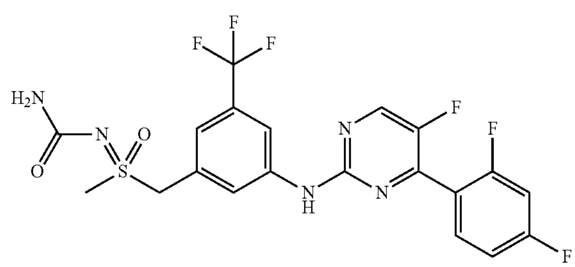 [SMILES: CS(=O)(Cc1cc(Nc2ncc(F)c(-c3ccc(F)cc3F)n2)cc(C(F)(F)F)c1)=NC(N)=O] | (rac)-1-{[3-{[4-(2,4-Difluorophenyl)-5-fluoropyrimidin-2-yl]amino}-5-(trifluoromethyl)benzyl](methyl)oxido-$\lambda^6$-sulfanylidene}urea |
| 8 | 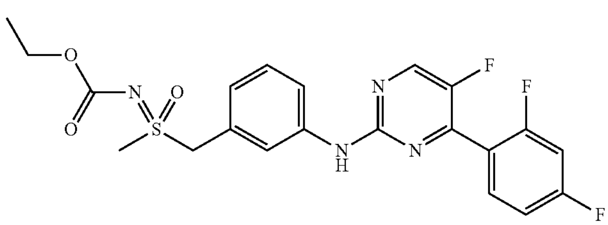 [SMILES: CCOC(=O)N=S(C)(=O)Cc1cccc(Nc2ncc(F)c(-c3ccc(F)cc3F)n2)c1] | (rac)-Ethyl[(3-{[4-(2,4-difluorophenyl)-5-fluoropyrimidin-2-yl]amino}benzyl)(methyl)oxido-$\lambda^6$-sulfanylidene]carbamate |
| 9 | 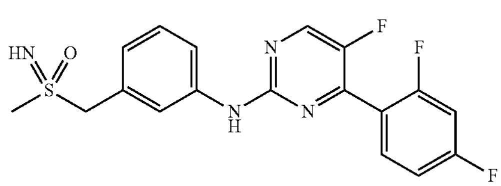 [SMILES: CS(=N)(=O)Cc1cccc(Nc2ncc(F)c(-c3ccc(F)cc3F)n2)c1] | (rac)-4-(2,4-Difluorophenyl)-5-fluoro-N-{3-[(S-methylsulfonimidoyl)methyl]phenyl}pyrimidin-2-amine |
| 10 | 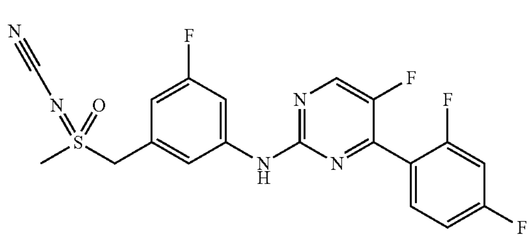 | (rac)-[(3-{[4-(2,4-Difluorophenyl)-5-fluoropyrimidin-2-yl]amino}-5-fluorobenzyl)(methyl)oxido-$\lambda^6$-sulfanylidene]cyanamide |

TABLE 1-continued

| Example No. | Structure | Name of compound |
|---|---|---|
| 11 | 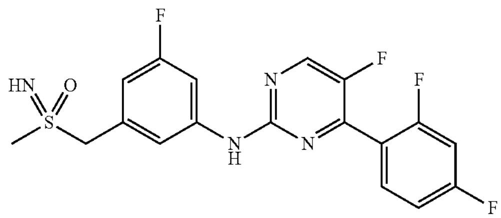 | (rac)-4-(2,4-Difluorophenyl)-5-fluoro-N-{3-fluoro-5-[(S-methylsulfonimidoyl)methyl]phenyl}pyrimidin-2-amine |
| 12 | 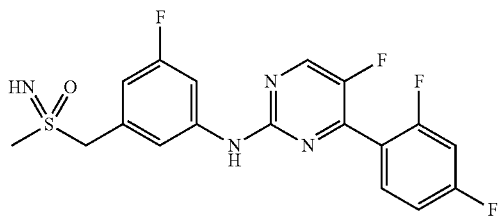 [SMILES: CS(=N)(=O)Cc1cc(F)cc(Nc2ncc(F)c(-c3ccc(F)cc3F)n2)c1] | 4-(2,4-Difluorophenyl)-5-fluoro-N-{3-fluoro-5-[(S-methylsulfonimidoyl)methyl]phenyl}pyrimidin-2-amine; enantiomer 1 |
| 13 | 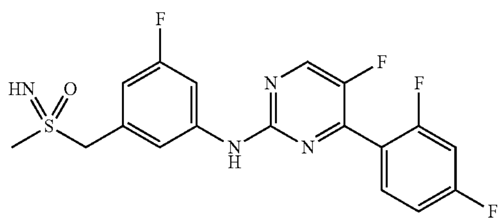 | 4-(2,4-Difluorophenyl)-5-fluoro-N-{3-fluoro-5-[(S-methylsulfonimidoyl)methyl]phenyl}pyrimidin-2-amine; enantiomer 2 |
| 14 | 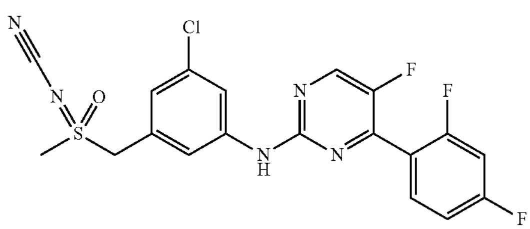 [SMILES: CS(=O)(Cc1cc(Cl)cc(Nc2ncc(F)c(-c3ccc(F)cc3F)n2)c1)=NC#N] | (rac)-[(3-Chloro-5-{[4-(2,4-difluorophenyl)-5-fluoropyrimidin-2-yl]amino}benzyl)(methyl)oxido-$\lambda^6$-sulfanylidene]cyanamide |
| 15 | 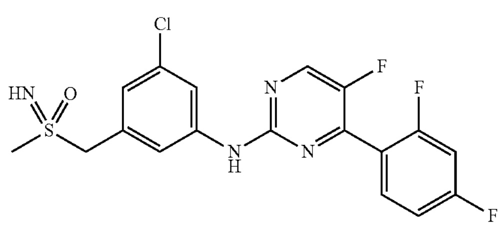 | (rac)-N-{3-Chloro-5-[(S-methylsulfonimidoyl)methyl]phenyl}-4-(2,4-difluorophenyl)-5-fluoropyrimidin-2-amine |
| 16 | 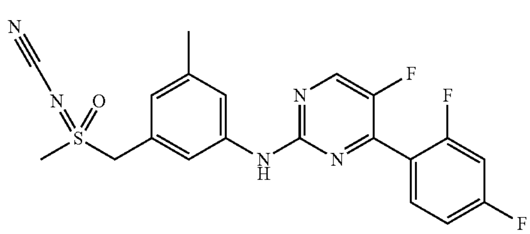 [SMILES: Cc1cc(CS(C)(=O)=NC#N)cc(Nc2ncc(F)c(-c3ccc(F)cc3F)n2)c1] | (rac)-[(3-{[4-(2,4-Difluorophenyl)-5-fluoropyrimidin-2-yl]amino}-5-methylbenzyl)(methyl)oxido-$\lambda^6$-sulfanylidene]cyanamide |
| 17 | 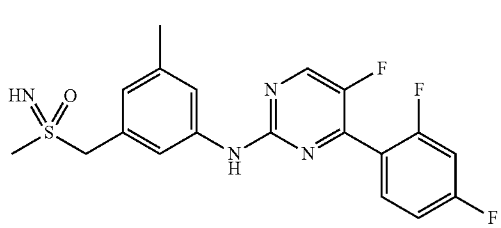 [SMILES: Cc1cc(CS(C)(=N)=O)cc(Nc2ncc(F)c(-c3ccc(F)cc3F)n2)c1] | (rac)-4-(2,4-Difluorophenyl)-5-fluoro-N-{3-methyl-5-[(S-methylsulfonimidoyl)methyl]phenyl}pyrimidin-2-amine |

TABLE 1-continued

| Example No. | Structure | Name of compound |
|---|---|---|
| 18 | 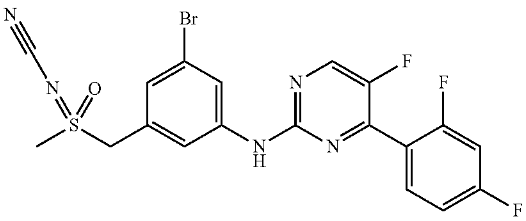 | (rac)-[(3-Bromo-5-{[4-(2,4-difluorophenyl)-5-fluoropyrimidin-2-yl]amino}benzyl)(methyl)oxido-λ⁶-sulfanylidene]cyanamide |
| 19 | 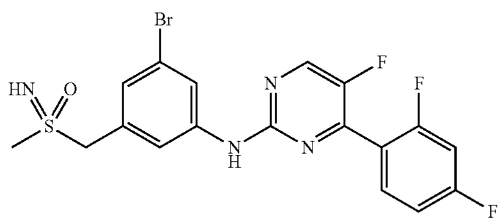 [SMILES: CS(=N)(=O)Cc1cc(Br)cc(Nc2ncc(F)c(-c3ccc(F)cc3F)n2)c1] | (rac)-N-{3-Bromo-5-[(S-methylsulfonimidoyl)methyl]phenyl}-4-(2,4-difluorophenyl)-5-fluoropyrimidin-2-amine |
| 20 | 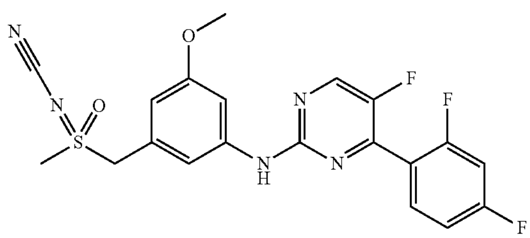 [SMILES: COc1cc(CS(C)(=O)=NC#N)cc(Nc2ncc(F)c(-c3ccc(F)cc3F)n2)c1] | (rac)-[(3-{[4-(2,4-Difluorophenyl)-5-fluoropyrimidin-2-yl]amino}-5-methoxybenzyl)(methyl)oxido-λ⁶-sulfanylidene]cyanamide |
| 21 | 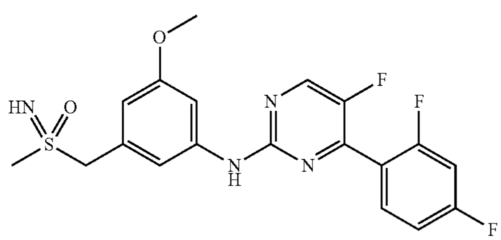 [SMILES: COc1cc(CS(C)(=N)=O)cc(Nc2ncc(F)c(-c3ccc(F)cc3F)n2)c1] | (rac)-4-(2,4-Difluorophenyl)-5-fluoro-N-{3-methoxy-5-[(S-methylsulfonimidoyl)methyl]phenyl}pyrimidin-2-amine |
| 22 | 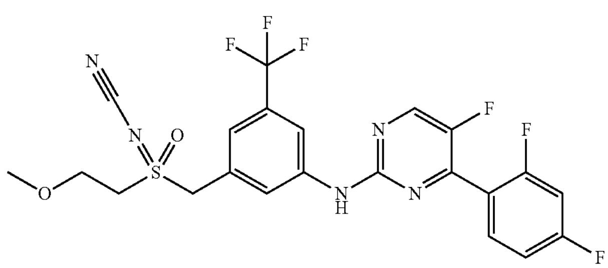 [SMILES: COCCS(=O)(Cc1cc(Nc2ncc(F)c(-c3ccc(F)cc3F)n2)cc(C(F)(F)F)c1)=NC#N] | (rac)-{[3-{[4-(2,4-Difluorophenyl)-5-fluoropyrimidin-2-yl]amino}-5-(trifluoromethyl)benzyl](2-methoxyethyl)oxido-λ⁶-sulfanylidene}cyanamide |
| 23 | 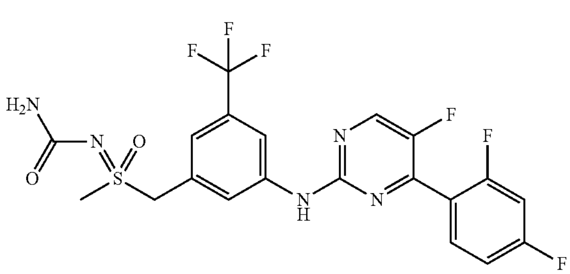 [SMILES: CS(=O)(Cc1cc(Nc2ncc(F)c(-c3ccc(F)cc3F)n2)cc(C(F)(F)F)c1)=NC(N)=O] | 1-{[3-{[4-(2,4-Difluorophenyl)-5-fluoropyrimidin-2-yl]amino}-5-(trifluoromethyl)benzyl](methyl)oxido-λ⁶-sulfanylidene}urea; enantiomer 1 |

TABLE 1-continued

| Example No. | Structure | Name of compound |
|---|---|---|
| 24 | 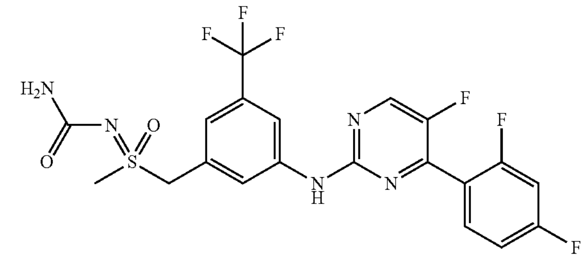 [SMILES: CS(=O)(Cc1cc(Nc2ncc(F)c(-c3ccc(F)cc3F)n2)cc(C(F)(F)F)c1)=NC(N)=O] | 1-{[3-{[4-(2,4-Difluorophenyl)-5-fluoropyrimidin-2-yl]amino}-5-(trifluoromethyl)benzyl](methyl)oxido-$\lambda^6$-sulfanylidene}urea; enantiomer 2 |
| 25 | 3 x TFA | (rac)-N-[3-{[S-(2-Aminoethyl)sulfonimidoyl]methyl}-5-(trifluoromethyl)phenyl]-4-(2,4-difluorophenyl)-5-fluoropyrimidin-2-amine trifluoroacetate |
| 26 | 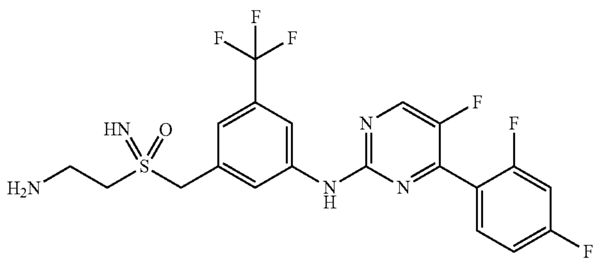 [SMILES: N=S(=O)(CCN)Cc1cc(Nc2ncc(F)c(-c3ccc(F)cc3F)n2)cc(C(F)(F)F)c1] | N-[3-{[S-(2-Aminoethyl)sulfonimidoyl]methyl}-5-(trifluoromethyl)phenyl]-4-(2,4-difluorophenyl)-5-fluoropyrimidin-2-amine enantiomer 1 |
| 27 | 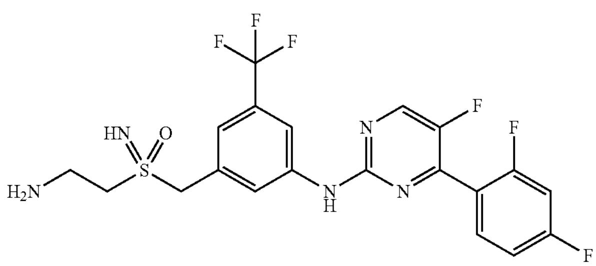 [SMILES: N=S(=O)(CCN)Cc1cc(Nc2ncc(F)c(-c3ccc(F)cc3F)n2)cc(C(F)(F)F)c1] | N-[3-{[S-(2-Aminoethyl)sulfonimidoyl]methyl}-5-(trifluoromethyl)phenyl]-4-(2,4-difluorophenyl)-5-fluoropyrimidin-2-amine; enantiomer 2 |
| 28 | 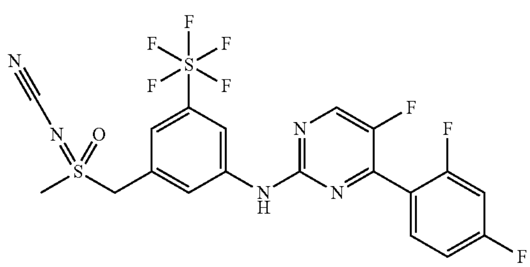 [SMILES: CS(=O)(Cc1cc(Nc2ncc(F)c(-c3ccc(F)cc3F)n2)cc(S(F)(F)(F)(F)F)c1)=NC#N] | (rac)-{[3-{[4-(2,4-Difluorophenyl)-5-fluoropyrimidin-2-yl]amino}-5-(pentafluoro-$\lambda^6$-sulfanyl)benzyl](methyl)oxido-$\lambda^6$-sulfanylidene}cyanamide |
| 29 | 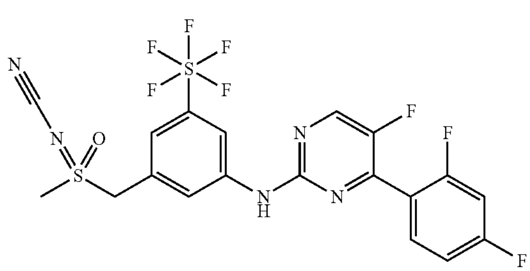 [SMILES: CS(=O)(Cc1cc(Nc2ncc(F)c(-c3ccc(F)cc3F)n2)cc(S(F)(F)(F)(F)F)c1)=NC#N] | {[3-{[4-(2,4-Difluorophenyl)-5-fluoropyrimidin-2-yl]amino}-5-(pentafluoro-$\lambda^6$-sulfanyl)benzyl](methyl)oxido-$\lambda^6$-sulfanylidene}cyanamide; enantiomer 1 |

TABLE 1-continued

| Example No. | Structure | Name of compound |
|---|---|---|
| 30 | 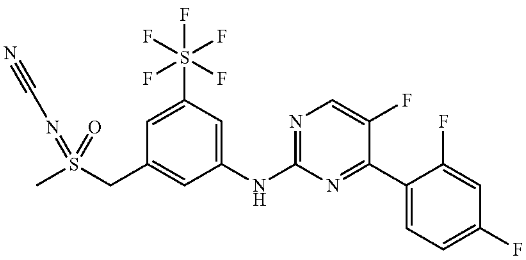 [SMILES: CS(=O)(Cc1cc(Nc2ncc(F)c(-c3ccc(F)cc3F)n2)cc(S(F)(F)(F)(F)F)c1)=NC#N] | {[3-{[4-(2,4-Difluorophenyl)-5-fluoropyrimidin-2-yl]amino}-5-(pentafluoro-$\lambda^6$-sulfanyl)benzyl](methyl)oxido-$\lambda^6$-sulfanylidene}cyanamide; enantiomer 2 |
| 31 | 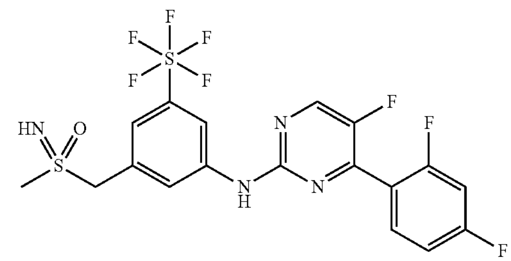 [SMILES: CS(=N)(=O)Cc1cc(Nc2ncc(F)c(-c3ccc(F)cc3F)n2)cc(S(F)(F)(F)(F)F)c1] | 4-(2,4-Difluorophenyl)-5-fluoro-N-{3-[(S-methylsulfonimidoyl)methyl]-5-(pentafluoro-$\lambda^6$-sulfanyl)phenyl}pyrimidin-2-amine; enantiomer 1 |
| 32 | 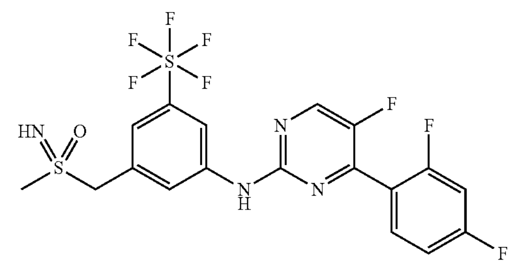 [SMILES: CS(=N)(=O)Cc1cc(Nc2ncc(F)c(-c3ccc(F)cc3F)n2)cc(S(F)(F)(F)(F)F)c1] | 4-(2,4-Difluorophenyl)-5-fluoro-N-{3-[(S-methylsulfonimidoyl)methyl]-5-(pentafluoro-$\lambda^6$-sulfanyl)phenyl}pyrimidin-2-amine; enantiomer 2 |
| 33 | 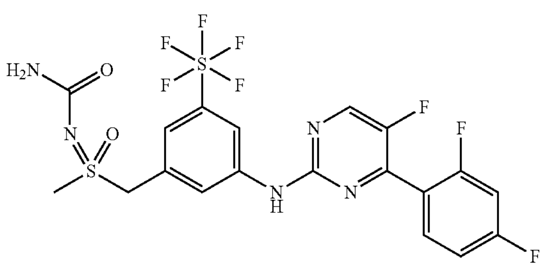 [SMILES: CS(=O)(Cc1cc(Nc2ncc(F)c(-c3ccc(F)cc3F)n2)cc(S(F)(F)(F)(F)F)c1)=NC(N)=O] | 1-{[3-{[4-(2,4-Difluorophenyl)-5-fluoropyrimidin-2-yl]amino}-5-(pentafluoro-$\lambda^6$-sulfanyl)benzyl](methyl)oxido-$\lambda^6$-sulfanylidene}urea; enantiomer 1 |
| 34 | 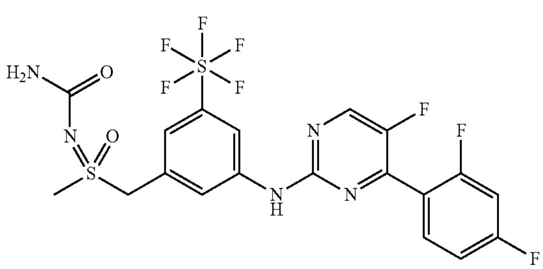 [SMILES: CS(=O)(Cc1cc(Nc2ncc(F)c(-c3ccc(F)cc3F)n2)cc(S(F)(F)(F)(F)F)c1)=NC(N)=O] | 1-{[3-{[4-(2,4-Difluorophenyl)-5-fluoropyrimidin-2-yl]amino}-5-(pentafluoro-$\lambda^6$-sulfanyl)benzyl](methyl)oxido-$\lambda^6$-sulfanylidene}urea; enantiomer 2 |
| 35 | 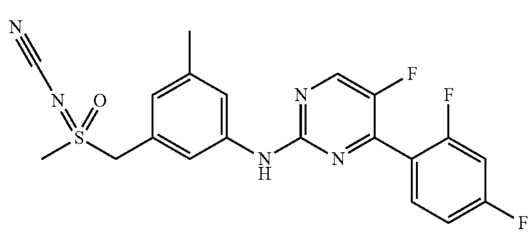 [SMILES: Cc1cc(CS(C)(=O)=NC#N)cc(Nc2ncc(F)c(-c3ccc(F)cc3F)n2)c1] | [(3-{[4-(2,4-Difluorophenyl)-5-fluoropyrimidin-2-yl]amino}-5-methylbenzyl)-(methyl)oxido-$\lambda^6$-sulfanylidene]cyanamide; enantiomer 1 |

TABLE 1-continued

| Example No. | Structure | Name of compound |
|---|---|---|
| 36 | 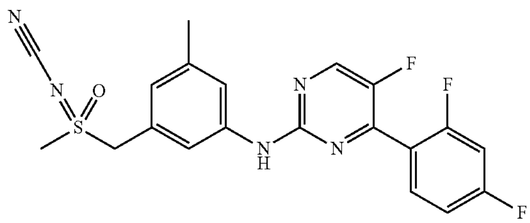 [SMILES: Cc1cc(CS(C)(=O)=NC#N)cc(Nc2ncc(F)c(-c3ccc(F)cc3F)n2)c1] | [(3-{[4-(2,4-Difluorophenyl)-5-fluoro-pyrimidin-2-yl]amino}-5-methylbenzyl)-(methyl)oxido-$\lambda^6$-sulfanylidene]cyanamide; enantiomer 2 |
| 37 | 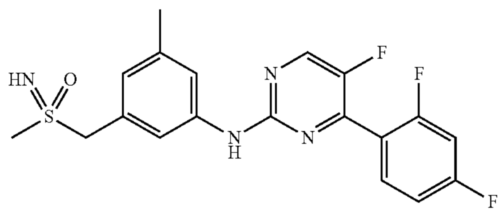 [SMILES: Cc1cc(CS(C)(=N)=O)cc(Nc2ncc(F)c(-c3ccc(F)cc3F)n2)c1] | 4-(2,4-Difluorophenyl)-5-fluoro-N-{3-methyl-5-[(S-methylsulfonimidoyl)methyl]-phenyl}pyrimidin-2-amine; enantiomer 1 |
| 38 | 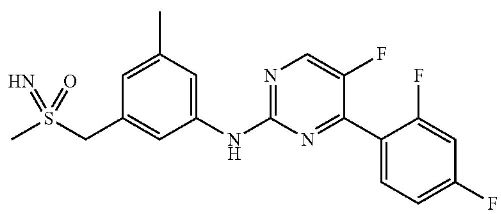 [SMILES: Cc1cc(CS(C)(=N)=O)cc(Nc2ncc(F)c(-c3ccc(F)cc3F)n2)c1] | 4-(2,4-Difluorophenyl)-5-fluoro-N-{3-methyl-5-[(S-methylsulfonimidoyl)methyl]-phenyl}pyrimidin-2-amine; enantiomer 2 |
| 39 | 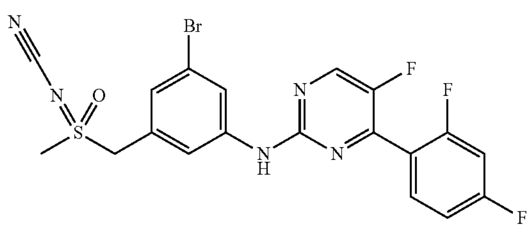 [SMILES: CS(=O)(Cc1cc(Br)cc(Nc2ncc(F)c(-c3ccc(F)cc3F)n2)c1)=NC#N] | [(3-Bromo-5-{[4-(2,4-difluorophenyl)-5-fluoropyrimidin-2-yl]amino}benzyl)(methyl)oxido-$\lambda^6$-sulfanylidene]cyanamide; enantiomer 1 |
| 40 | 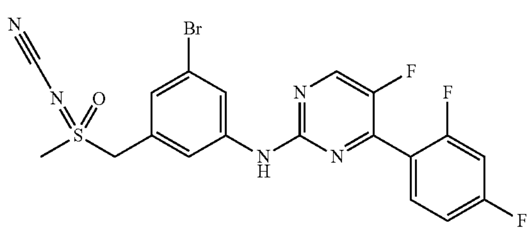 | [(3-Bromo-5-{[4-(2,4-difluorophenyl)-5-fluoropyrimidin-2-yl]amino}benzyl)(methyl)oxido-$\lambda^6$-sulfanylidene]cyanamide; enantiomer 2 |
| 41 | 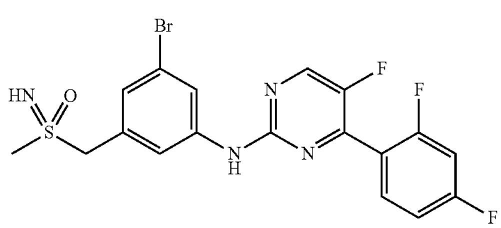 | N-{3-Bromo-5-[(S-methylsulfonimidoyl)methyl]phenyl}-4-(2,4-difluorophenyl)-5-fluoropyrimidin-2-amine; enantiomer 1 |
| 42 | 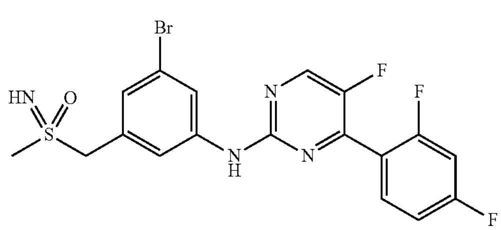 | N-{3-Bromo-5-[(S-methylsulfonimidoyl)methyl]phenyl}-4-(2,4-difluorophenyl)-5-fluoropyrimidin-2-amine; enantiomer 2 |

TABLE 1-continued
| Example No. | Structure | Name of compound |
|---|---|---|
Results:
Table 2: Inhibition for CDK9 and CDK2 of compounds according to the present invention
The IC$_{50}$ (inhibitory concentration at 50% of maximal effect) values are indicated in nM, "n.t." means that the compounds have not been tested in this assay.
TABLE 2
| ① | Structure of compound | ② | ③ | ④ | ⑤ |
|---|---|---|---|---|---|
| 1 | 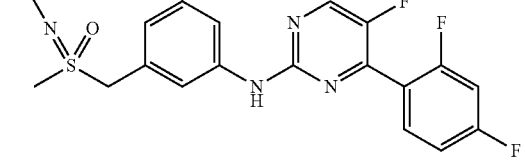 | 13 | 1400 | 39 | 105 |
| 2 | 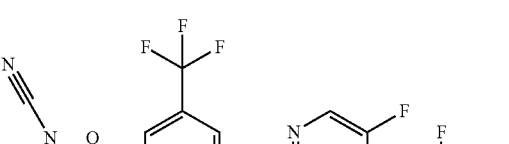 | 7 | 1200 | 29 | 166 |
| 3 | 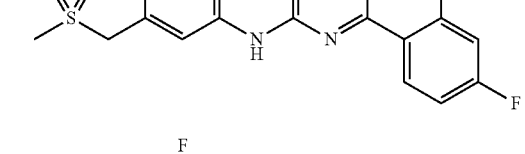 | 8 | 1300 | 32 | 170 |
| 4 | 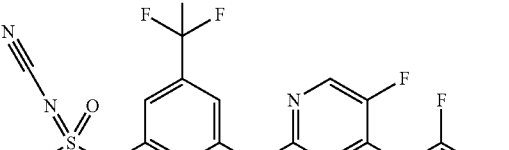 | 10 | 880 | 251 | 88 |
| 5 | 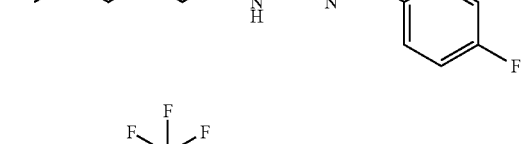 | 11 | 780 | 235 | 72 |

TABLE 2-continued

| ① | Structure of compound | ② | ③ | ④ | ⑤ |
|---|---|---|---|---|---|
| 6 | | 13 | 630 | 231 | 50 |
| 7 | | 12 | 1100 | 105 | 98 |
| 8 | | 25 | 560 | 1500 | 22 |
| 9 | | 42 | 1100 | 2710 | 25 |
| 10 | | 17 | 570 | 289 | 33 |
| 11 | | 33 | 920 | 979 | 28 |
| 12 | | 29 | 1700 | 1090 | 60 |

TABLE 2-continued
| ① | Structure of compound | ② | ③ | ④ | ⑤ |
|---|---|---|---|---|---|
| 13 | 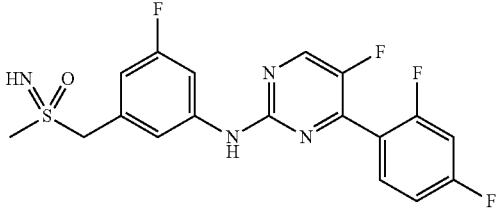 | 25 | 730 | 1160 | 29 |
| 14 | 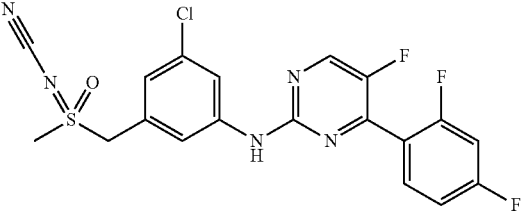 [SMILES: CS(=O)(Cc1cc(Cl)cc(Nc2ncc(F)c(-c3ccc(F)cc3F)n2)c1)=NC#N] | 8 | 530 | 272 | 65 |
| 15 | 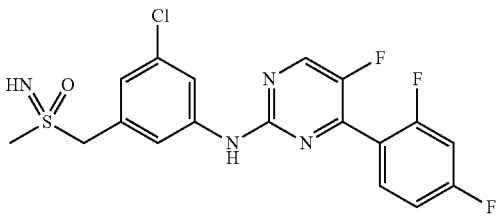 | 24 | 630 | 892 | 26 |
| 16 | 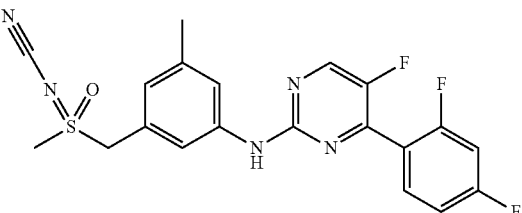 | 6 | 470 | 165 | 73 |
| 17 | 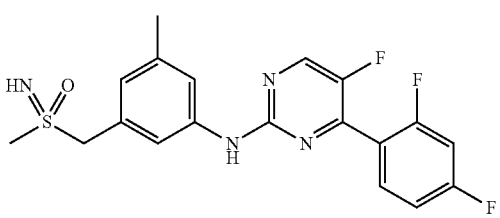 [SMILES: Cc1cc(CS(C)(=N)=O)cc(Nc2ncc(F)c(-c3ccc(F)cc3F)n2)c1] | 26 | 480 | 470 | 19 |
| 18 | 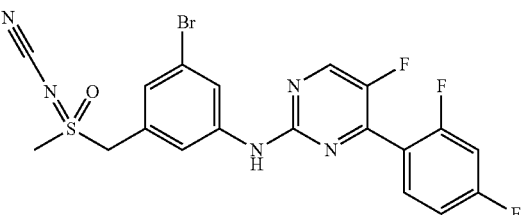 | 11 | 470 | 175 | 44 |
| 19 | 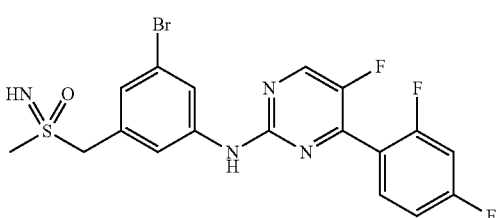 | 13 | 380 | n.t. | 30 |

TABLE 2-continued

| ① | Structure of compound | ② | ③ | ④ | ⑤ |
|---|---|---|---|---|---|
| 20 | (structure) | 3 | 230 | 21 | 93 |
| 21 | (structure) | 26 | 1100 | 1180 | 41 |
| 22 | (structure) | 7 | 1200 | 19 | 183 |
| 23 | (structure) | 4 | 370 | 16 | 88 |
| 24 | (structure) | 10 | 670 | 199 | 66 |
| 25 | (structure, 3 x TFA) | 85 | 3200 | 417 | 38 |

TABLE 2-continued

| ① | Structure of compound | ② | ③ | ④ | ⑤ |
|---|---|---|---|---|---|
| 26 | | n.t. | 1300 | 278 | n.t. |
| 27 | | n.t. | 1100 | 276 | n.t. |
| 28 | | 6 | 1300 | 5 | 210 |
| 29 | | 5 | 940 | 8 | 198 |
| 30 | | 4 | 1500 | 9 | 360 |
| 31 | | 54 | 890 | 7 | 16 |

TABLE 2-continued

| ① | Structure of compound | ② | ③ | ④ | ⑤ |
|---|---|---|---|---|---|
| 32 | | 6 | 1600 | 6 | 263 |
| 33 | | 16 | 1600 | 99 | 98 |
| 34 | | 4 | n.t. | 11 | n.t. |
| 35 | | 5 | 390 | 61 | 73 |
| 36 | | 6 | 400 | 177 | 70 |
| 37 | | 36 | 830 | 6310 | 23 |

TABLE 2-continued

| ① Structure of compound | ② | ③ | ④ | ⑤ |
|---|---|---|---|---|
| 38 | 19 | 720 | 6490 | 38 |
| 39 | 9 | 430 | 177 | 47 |
| 40 | 8 | 102 | n.t. | 105 |
| 41 | 18 | 509 | n.t. | 28 |
| 42 | 15 | 470 | 334 | 30 |

①: Example Number
②: CDK9: CDK9/CycT1 kinase assay as described under Method 1a. of Materials and Methods
③: CDK2: CDK2/CycE kinase assay as described under Method 2. of Materials and Methods
④: high ATP CDK9: CDK9/CycT1 kinase assay as described under Method 1b. of Materials and Methods
⑤: Selectivity CDK9/CDK2 as derived from Methods 1a. and 2. of Materials and Methods Tables 3a and 3b:

Inhibition of proliferation of HeLa, HeLa-MaTu-ADR, A2780, NCI-H460, DU145, Caco-2, B16F10 and MOLM-13 cells by compounds according to the present invention, determined as described above (Method 3. of Materials and Methods section). All IC$_{50}$ (inhibitory concentration at 50% of maximal effect) values are indicated in nM, "n.t." means that the compounds have not been tested in this assay.

TABLE 3a

Indications represented by cell lines

| Cell line | Source | Indication |
|---|---|---|
| HeLa | ATCC | Human cervical tumour |
| NCI-H460 | ATCC | Human non-small cell lung carcinoma |

TABLE 3a-continued

Indications represented by cell lines

| Cell line | Source | Indication |
|---|---|---|
| A2780 | ECACC | Human ovarian carcinoma |
| DU 145 | ATCC | Hormone-independent human prostate carcinoma |
| HeLa-MaTu-ADR | EPO-GmbH Berlin | Multidrug-resistant human cervical carcinoma |
| Caco-2 | ATCC | Human colorectal carcinoma |
| B16F10 | ATCC | Mouse melanoma |
| MOLM-13 | DSMZ | Human acute myeloid leukemia |

TABLE 3b

| ① | Structure of compound | ② | ③ | ④ | ⑤ | ⑥ | ⑦ | ⑧ | ⑨ |
|---|---|---|---|---|---|---|---|---|---|
| 1 | [structure] | 440 | n.t. | n.t. | n.t. | n.t. | n.t. | n.t. | n.t. |
| 2 | [structure] | 350 | 320 | 360 | 310 | 300 | 390 | 130 | n.t. |
| 3 | [structure] | 590 | 200 | 340 | 370 | 300 | 340 | 260 | n.t. |
| 4 | [structure] | 960 | n.t. | n.t. | n.t. | n.t. | n.t. | n.t. | n.t. |

TABLE 3b-continued

| | | Inhibition of proliferation | | | | | | | |
|---|---|---|---|---|---|---|---|---|---|
| ① | Structure of compound | ② | ③ | ④ | ⑤ | ⑥ | ⑦ | ⑧ | ⑨ |
| 5 | | 840 | n.t. | n.t. | n.t. | n.t. | n.t. | 95 | 316 |
| 6 | | 950 | n.t. | n.t. | n.t. | n.t. | n.t. | 300 | 374 |
| 7 | | 470 | n.t. | n.t. | n.t. | n.t. | n.t. | n.t. | n.t. |
| 8 | | 4470 | n.t. | n.t. | n.t. | n.t. | n.t. | n.t. | n.t. |
| 10 | | 1050 | n.t. | n.t. | n.t. | n.t. | n.t. | 430 | n.t. |
| 11 | | 1320 | n.t. | n.t. | n.t. | n.t. | n.t. | 900 | n.t. |

TABLE 3b-continued

| ① | Structure of compound | ② | ③ | ④ | ⑤ | ⑥ | ⑦ | ⑧ | ⑨ |
|---|---|---|---|---|---|---|---|---|---|
| 12 | | 1940 | n.t. | n.t. | n.t. | n.t. | n.t. | >1000 | n.t. |
| 13 | | 1760 | n.t. | n.t. | n.t. | n.t. | n.t. | >1000 | n.t. |
| 14 | | 1020 | n.t. | n.t. | n.t. | n.t. | n.t. | 540 | n.t. |
| 15 | | 2210 | n.t. | n.t. | n.t. | n.t. | n.t. | 110 | n.t. |
| 16 | | 850 | n.t. | n.t. | n.t. | n.t. | n.t. | 300 | n.t. |
| 17 | | 1360 | n.t. | n.t. | n.t. | n.t. | n.t. | 180 | n.t. |
| 18 | | 1050 | n.t. | n.t. | n.t. | n.t. | n.t. | 110 | n.t. |

TABLE 3b-continued
| | | Inhibition of proliferation | | | | | | | |
|---|---|---|---|---|---|---|---|---|---|
| ① | Structure of compound | ② | ③ | ④ | ⑤ | ⑥ | ⑦ | ⑧ | ⑨ |
| 19 | 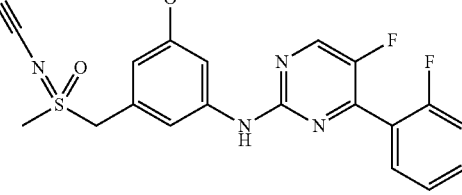 | 1600 | n.t. | n.t. | n.t. | n.t. | n.t. | n.t. | n.t. |
| 20 | 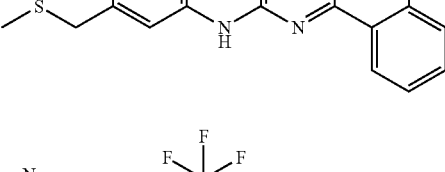 | 320 | 330 | 384 | 340 | 344 | 321 | n.t. | n.t. |
| 21 | 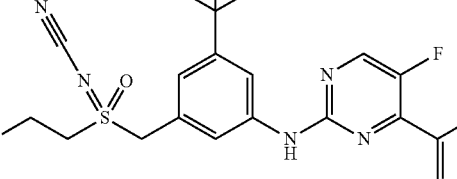 | 780 | n.t. | n.t. | n.t. | n.t. | n.t. | n.t. | n.t. |
| 22 | 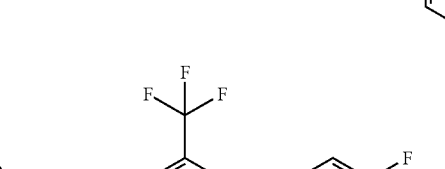 | 900 | n.t. | n.t. | n.t. | n.t. | n.t. | n.t. | n.t. |
| 23 | 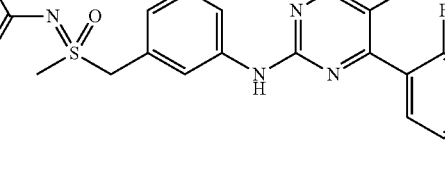 | 290 | 200 | 350 | 250 | 230 | 380 | 970 | n.t. |
| 24 | 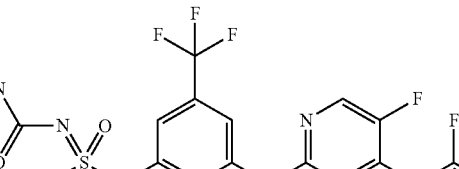 | 910 | n.t. | n.t. | n.t. | n.t. | n.t. | 320 | n.t. |

TABLE 3b-continued

Inhibition of proliferation

| ① | Structure of compound | ② | ③ | ④ | ⑤ | ⑥ | ⑦ | ⑧ | ⑨ |
|---|---|---|---|---|---|---|---|---|---|
| 25 | | 2210 | n.t. | n.t. | n.t. | n.t. | n.t. | n.t. | n.t. |
| 28 | | 262 | 120 | 359 | 311 | 222 | 363 | 185 | 145 |
| 29 | | 178 | n.t. | n.t. | n.t. | n.t. | n.t. | 96 | 92 |
| 30 | | 359 | n.t. | n.t. | n.t. | n.t. | n.t. | 167 | 141 |
| 31 | | 501 | n.t. | n.t. | n.t. | n.t. | n.t. | 279 | 281 |

TABLE 3b-continued

| | | Inhibition of proliferation | | | | | | | |
|---|---|---|---|---|---|---|---|---|---|
| ① | Structure of compound | ② | ③ | ④ | ⑤ | ⑥ | ⑦ | ⑧ | ⑨ |
| 32 | *structure* | 331 | 304 | 483 | 397 | 282 | 406 | 268 | 165 |
| 33 | *structure* | 278 | 495 | 675 | 507 | 716 | 611 | 246 | 200 |
| 34 | *structure* | 172 | 134 | 317 | 142 | 202 | 323 | 99 | 39 |
| 35 | *structure* | 458 | n.t. | n.t. | n.t | n.t | n.t | 327 | n.t |
| 36 | *structure* | 1020 | n.t. | n.t. | n.t. | n.t. | n.t. | 338 | n.t. |
| 37 | *structure* | 1080 | n.t. | n.t. | n.t. | n.t. | n.t. | n.t. | n.t. |

TABLE 3b-continued

Inhibition of proliferation

| ① | Structure of compound | ② | ③ | ④ | ⑤ | ⑥ | ⑦ | ⑧ | ⑨ |
|---|---|---|---|---|---|---|---|---|---|
| 38 | *[structure]* | 649 | n.t. | n.t. | n.t. | n.t. | n.t. | n.t. | n.t. |
| 39 | *[structure]* | 1060 | n.t. | n.t. | n.t. | n.t. | n.t. | 619 | n.t. |
| 40 | *[structure]* | 697 | n.t. | n.t. | n.t. | n.t. | n.t. | 371 | n.t. |
| 42 | *[structure]* | 1060 | n.t. | n.t. | n.t. | n.t. | n.t. | 1000 | 946 |

①: Example Number
②: Inhibition of HeLa cell proliferation
③: Inhibition of HeLa-MaTu-ADR cell proliferation
④: Inhibition of H460 cell proliferation
⑤: Inhibition of DU145 cell proliferation
⑥: Inhibition of Caco-2 cell proliferation
⑦: Inhibition of B16F10 cell proliferation
⑧: Inhibition of A2780 cell proliferation
⑨: Inhibition of MOLM-13 cell proliferation Table 4:
Inhibition of Carbonic anhydrase-1 and Carbonic anhydrase-2 as determined by Method 4.

TABLE 4

| ① | Structure of compound | ② | ③ |
|---|---|---|---|
| 1 | *[structure]* | >10000 | >10000 |

TABLE 4-continued

| ① Compound Number | Structure of compound | ② | ③ |
|---|---|---|---|
| 4 | 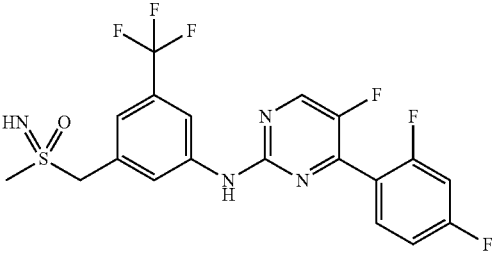 [SMILES: CS(=N)(=O)Cc1cc(Nc2ncc(F)c(-c3ccc(F)cc3F)n2)cc(C(F)(F)F)c1] | >10000 | >10000 |
| 7 | 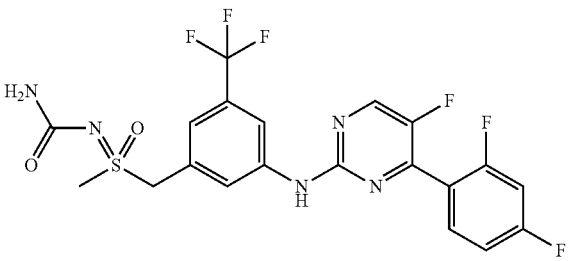 [SMILES: CS(=O)(Cc1cc(Nc2ncc(F)c(-c3ccc(F)cc3F)n2)cc(C(F)(F)F)c1)=NC(N)=O] | >10000 | >10000 |
| 15 | 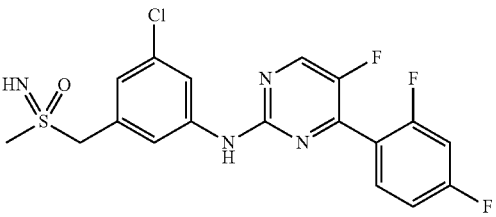 | >10000 | >10000 |
| 18 | 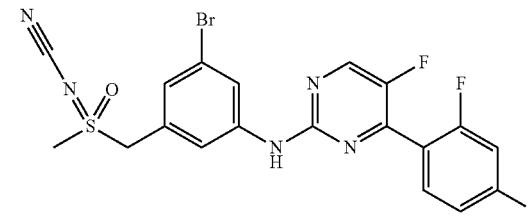 | >10000 | >10000 |

①: Compound Number
②: Inhibition of Carbonic anhydrase-1: the $IC_{50}$ (inhibitory concentration at 50% of maximal effect) values are indicated in nM.
③ Inhibition of Carbonic anhydrase-2: the $IC_{50}$ (inhibitory concentration at 50% of maximal effect) values are indicated in nM.

Table 5:
Stability in rat hepatocytes and $t_{1/2}$ in rats after iv dosing as determined by method 5. and method 6. as described above.

TABLE 5

| ① | Structure of compound | ② | ③ |
|---|---|---|---|
| 1 | 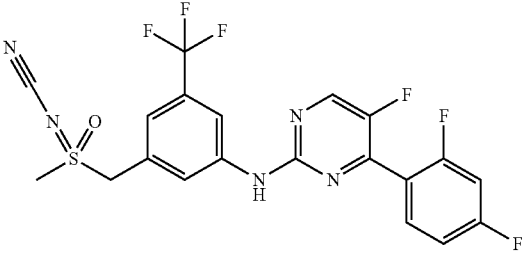 [SMILES: CS(=O)(Cc1cc(Nc2ncc(F)c(-c3ccc(F)cc3F)n2)cc(C(F)(F)F)c1)=NC#N] | 75% | n.d. |

TABLE 5-continued

| ① | Structure of compound | ② | ③ |
|---|---|---|---|
| 2 | | 79% | 4.3 h |
| 3 | | 76% | n.d. |
| 4 | | 91% | 4.5 h |
| 5 | | 77% | n.d. |
| 6 | | 71% | n.d. |
| 7 | | 80% | n.d. |

TABLE 5-continued
| ① | Structure of compound | ② | ③ |
|---|---|---|---|
| 14 | 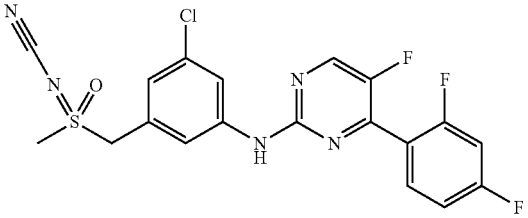 | 75% | n.d. |
| 15 | 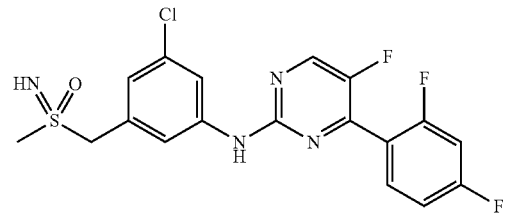 | 79% | n.d. |
| 23 | 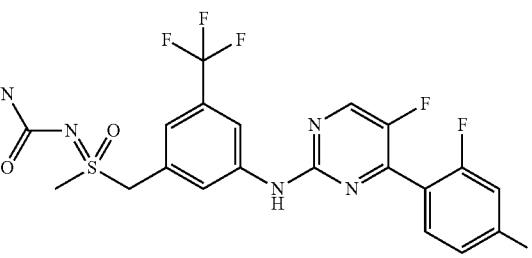 | 93% | n.d. |
| 24 | 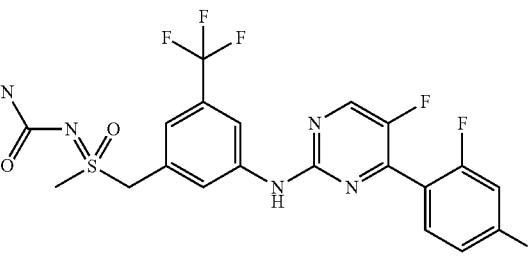 | 82% | n.d. |
| 32 | 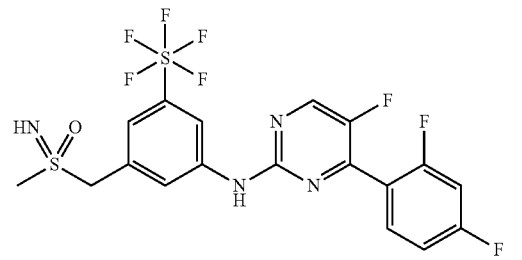 | 91% | 15 h |
| 34 | 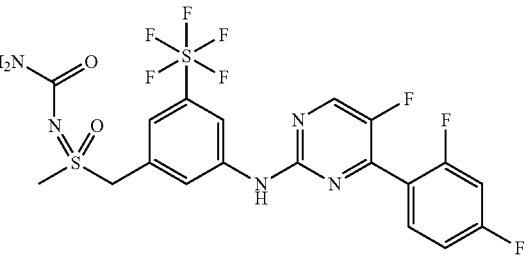 | 90% | n.d. |
①: Compound Number
②: The maximal calculated oral bioavailability (Fmax) based on stability data in rat Hepatocytes.
③: $t_{1/2}$: terminal half-life (in h) from in vivo rat study.

The invention claimed is:

1. A compound of general formula (I)

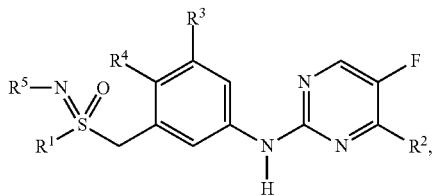

wherein
$R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$;
$R^2$ represents the group

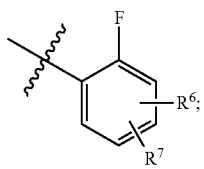

$R^3$, $R^4$ represent, independently from each other, a group selected from a hydrogen atom, halogen atom, cyano, —SF$_5$, $C_1$-$C_3$-alkyl-, $C_1$-$C_3$-alkoxy-, hydroxy, halo-$C_1$-$C_3$-alkyl-, $C_1$-$C_3$-fluoroalkoxy-;
$R^5$ represents a group selected from a hydrogen atom, cyano, —C(O)$R^8$, —C(O)O$R^8$, —S(O)$_2R^8$, —C(O)NR$^9$R$^{10}$, —P(O)(OR$^{11}$)$_2$, —CH$_2$OP(OR$^{11}$)$_2$, $C_1$-$C_6$-alkyl-, $C_3$-$C_7$-cycloalkyl-, heterocyclyl-, phenyl, heteroaryl,
wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;
$R^8$ represents a group selected from $C_1$-$C_6$-alkyl-, $C_3$-$C_7$-cycloalkyl-, heterocyclyl-, phenyl, benzyl or heteroaryl,
wherein said group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^9$, $R^{10}$ represent, independently from each other, a group selected from hydrogen, $C_1$-$C_6$-alkyl-, $C_3$-$C_7$-cycloalkyl-, heterocyclyl-, phenyl, benzyl or heteroaryl,
wherein said $C_1$-$C_6$-alkyl, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or
$R^9$ and $R^{10}$, together with the nitrogen atom they are attached to, form a cyclic amine;
$R^{11}$ represents a group selected from hydrogen, $C_1$-$C_4$-alkyl or benzyl,
or an enantiomers, diastereomers, salts, solvates or salts of solvates thereof,
with the proviso that the compound is not
(rac)-ethyl[(3-{[4-(2,4-difluorophenyl)-5-fluoropyrimidin-2-yl]amino}benzyl)(methyl)oxido-λ$^6$-sulfanylidene]carbamate.

2. The compound of general formula (I) according to claim 1, wherein
$R^1$ represents a group selected from $C_1$-$C_6$-alkyl-, $C_3$-$C_7$-cycloalkyl, phenyl, or phenyl-$C_1$-$C_3$-alkyl-,
wherein said group is optionally substituted with one or two or three substituents, identically or differently, selected from the group of hydroxy, cyano, halogen, halo-$C_1$-$C_3$-alkyl-, $C_1$-$C_3$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$;
$R^2$ represents the group

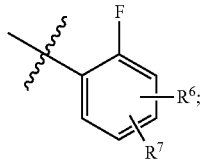

$R^3$, $R^4$ represent, independently from each other, a group selected from a hydrogen atom, halogen atom, —SF$_5$, $C_1$-$C_3$-alkyl-, $C_1$-$C_3$-alkoxy-, halo-$C_1$-$C_3$-alkyl-, $C_1$-$C_3$-fluoroalkoxy-;
$R^5$ represents a group selected from a hydrogen atom, cyano, —C(O)$R^8$, —S(O)$_2R^8$, —C(O)NR$^9$R$^{10}$, —P(O)(OR$^{11}$)$_2$, —CH$_2$OP(OR$^{11}$)$_2$, $C_1$-$C_3$-alkyl-, $C_3$-$C_5$-cycloalkyl-, phenyl,
wherein said $C_1$-$C_3$-alkyl, $C_3$-$C_5$-cycloalkyl- or phenyl group is optionally substituted with one or two substituents, identically or differently, selected from hydroxy, —NH$_2$, alkylamino-, dialkylamino-, cyclic amines;
$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;
$R^8$ represents a group selected from $C_1$-$C_3$-alkyl-, $C_3$-$C_5$-cycloalkyl-, heterocyclyl-, phenyl or benzyl,
wherein said group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^9$, $R^{10}$ represent, independently from each other, a group selected from hydrogen, $C_1$-$C_3$-alkyl-, $C_3$-$C_5$-cycloalkyl-, heterocyclyl-, phenyl or benzyl, wherein said $C_1$-$C_3$-alkyl-, $C_3$-$C_5$-cycloalkyl-, heterocyclyl-, phenyl or benzyl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-; or $R^9$ and $R^{10}$, together with the nitrogen atom they are attached to, form a cyclic amine;

$R^{11}$ represents a group selected from hydrogen or $C_1$-$C_4$-alkyl, or an enantiomer, diastereomer, salt, solvate or salt of a solvate thereof.

3. The compound of general formula (I) according to claim 1, wherein $R^1$ represents a group selected from $C_1$-$C_6$-alkyl-, wherein said group is optionally substituted with one substituent selected from the group of $C_1$-$C_3$-alkoxy, —$NH_2$, alkylamino, dialkylamino, cyclic amines, hydroxy, —$OP(O)(OH)_2$;

$R^2$ represents the group

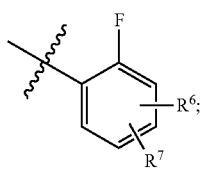

$R^3$ represents a group selected from a hydrogen atom, halogen atom, —$SF_5$, $C_1$-$C_3$-alkyl, $C_1$-$C_3$-alkoxy, or halo-$C_1$-$C_3$-alkyl-;

$R^4$ represents a hydrogen atom or a fluoro atom;

$R^5$ represents a group selected from a hydrogen atom, cyano, —$C(O)NR^9R^{10}$, —$P(O)(OR^{11})_2$, —$CH_2OP(OR^{11})_2$ or $C_1$-$C_3$-alkyl, wherein said $C_1$-$C_3$-alkyl group is optionally substituted with one substituent, selected from —$NH_2$, alkylamino-, dialkylamino-, or cyclic amines;

$R^6$, $R^7$ represent, independently from each other, a group selected from a hydrogen atom, fluoro atom, $C_1$-$C_3$-alkyl-;

$R^9$, $R^{10}$ represent, independently from each other, a group selected from hydrogen, $C_1$-$C_3$-alkyl-, $C_3$-$C_5$-cycloalkyl-, or benzyl, wherein said $C_1$-$C_3$-alkyl-, $C_3$-$C_5$-cycloalkyl- or benzyl group is optionally substituted with one or two substituents, identically or differently, selected from halogen, hydroxy, $C_1$-$C_3$-alkyl-, $C_1$-$C_3$-alkoxy-, —$NH_2$, alkylamino-, dialkylamino-, or $R^9$ and $R^{10}$, together with the nitrogen atom they are attached to, form a cyclic amine;

$R^{11}$ represents a group selected from hydrogen or $C_1$-$C_2$-alkyl, or an enantiomer, diastereomer, salt, solvate or salt of a solvate thereof.

4. The compound of general formula (I) according to claim 1, wherein $R^1$ represents a $C_1$-$C_3$-alkyl group;

wherein said group is optionally substituted with one substituent selected from the group of $C_1$-$C_3$-alkoxy, —$NH_2$, alkylamino-, dialkylamino-, or cyclic amines;

$R^2$ represents the group

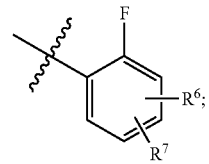

$R^3$ represents a group selected from a halogen atom or a —$SF_5$, $C_1$-$C_3$-alkyl- or fluoro-$C_1$-$C_3$alkyl group;

$R^4$ represents a hydrogen atom;

$R^5$ represents a group selected from a hydrogen atom, cyano, —$C(O)NR^9R^{10}$;

$R^6$, $R^7$ represent, independently from each other, a group selected from a hydrogen atom or a fluoro atom;

$R^9$, $R^{10}$ represent, independently from each other, a group selected from hydrogen or $C_1$-$C_2$-alkyl-;

or an enantiomer, diastereomer, salt, solvate or salt of a solvate thereof.

5. The compound of general formula (I) according to claim 1, wherein $R^1$ represents a methyl, 2-aminoethyl or 2-methoxyethyl group;

$R^2$ represents a 2,4-difluorophenyl group;

$R^3$ represents a group selected from hydrogen, fluoro, chloro, bromo, —$SF_5$, methyl, methoxy or trifluoromethyl;

$R^4$ represents a hydrogen atom;

$R^5$ represents a group selected from a hydrogen atom, cyano, —$C(O)NH_2$;

or an enantiomer, diastereomer, salt, solvate or salt of a solvate thereof.

6. The compound of general formula (I) according to claim 1, wherein $R^1$ represents a methyl, 2-aminoethyl or 2-methoxyethyl group;

$R^2$ represents a 2,4-difluorophenyl group;

$R^3$ represents a group selected from fluoro, chloro, bromo, —$SF_5$, methyl or trifluoromethyl;

$R^4$ represents a hydrogen atom;

$R^5$ represents a group selected from a hydrogen atom, cyano, —$C(O)NH_2$;

or an enantiomer, diastereomer, salt, solvate or salt of a solvate thereof.

7. The compound of general formula (I) according to claim 1, wherein $R^1$ represents a methyl group;

$R^2$ represents a 2,4-difluorophenyl group;

$R^3$ represents a —$SF_5$ or trifluoromethyl group;

$R^4$ represents a hydrogen atom;

$R^5$ represents a group selected from a hydrogen atom, cyano, —$C(O)NH_2$, or an enantiomer, diastereomer, salt, solvate or salt of a solvate thereof.

8. The compound according to claim 1, which is selected from (rac)-{[3-{[4-(2,4-Difluorophenyl)-5-fluoropyrimidin-2-yl]amino}-5-(trifluoromethyl)benzyl](methyl)oxido-$\lambda^6$-sulfanylidene}cyanamide;

{[3-{[4-(2,4-Difluorophenyl)-5-fluoropyrimidin-2-yl]
amino}-5-(trifluoromethyl)benzyl](methyl)oxido-$\lambda^6$-
sulfanylidene}cyanamide, enantiomer 1;

{[3-{[4-(2,4-Difluorophenyl)-5-fluoropyrimidin-2-yl]
amino}-5-(trifluoromethyl)benzyl](methyl)oxido-$\lambda^6$-
sulfanylidene}cyanamide, enantiomer 2;

(rac)-4-(2,4-Difluorophenyl)-5-fluoro-N-{3-[(S-methyl-
sulfonimidoyl)methyl]-5-(trifluoromethyl)
phenyl}pyrimidin-2-amine;

4-(2,4-Difluorophenyl)-5-fluoro-N-{3-[(S-methylsulfon-
imidoyl)methyl]-5-(trifluoromethyl)phenyl}pyrimidin-
2-amine, enantiomer 1;

4-(2,4-Difluorophenyl)-5-fluoro-N-{3-[(S-methylsulfon-
imidoyl)methyl]-5-(trifluoromethyl)phenyl}pyrimidin-
2-amine, enantiomer 2;

(rac)-1-{[3-{[4-(2,4-Difluorophenyl)-5-fluoropyrimidin-
2-yl]amino}-5-(trifluoromethyl)benzyl](methyl)oxido-
$\lambda^6$-sulfanylidene}urea;

(rac)-Ethyl[(3-{[4-(2,4-difluorophenyl)-5-fluoropyrimi-
din-2-yl]amino}benzyl)(methyl)oxido-$\lambda^6$-sulfa-
nylidene]carbamate;

(rac)-4-(2,4-Difluorophenyl)-5-fluoro-N-{3-[(S-methyl-
sulfonimidoyl)methyl]phenyl}pyrimidin-2-amine;

(rac)-[(3-{[4-(2,4-Difluorophenyl)-5-fluoropyrimidin-2-
yl]amino}-5-fluorobenzyl)(methyl)oxido-$\lambda^6$-sulfa-
nylidene]cyanamide;

(rac)-4-(2,4-Difluorophenyl)-5-fluoro-N-{3-fluoro-5-[(S-
methylsulfonimidoyl)methyl]phenyl}pyrimidin-2-
amine;

4-(2,4-Difluorophenyl)-5-fluoro-N-{3-fluoro-5-[(S-
methylsulfonimidoyl)methyl]phenyl}pyrimidin-2-
amine; enantiomer 1;

4-(2,4-Difluorophenyl)-5-fluoro-N-{3-fluoro-5-[(S-
methylsulfonimidoyl)methyl]phenyl}pyrimidin-2-
amine; enantiomer 2;

(rac)-[(3-Chloro-5-{[4-(2,4-difluorophenyl)-5-fluoropy-
rimidin-2-yl]amino}benzyl)(methyl)oxido-$\lambda^6$-sulfa-
nylidene]cyanamide;

(rac)-N-{3-chloro-5-[(S-methylsulfonimidoyl)methyl]
phenyl}-4-(2,4-difluorophenyl)-5-fluoropyrimidin-2-
amine;

(rac)-[(3-{[4-(2,4-Difluorophenyl)-5-fluoropyrimidin-2-
yl]amino}-5-methylbenzyl)(methyl)oxido-$\lambda^6$-sulfa-
nylidene]cyanamide;

(rac)-4-(2,4-Difluorophenyl)-5-fluoro-N-{3-methyl-5-
[(S-methylsulfonimidoyl)methyl]phenyl}pyrimidin-2-
amine;

(rac)-[(3-Bromo-5-{[4-(2,4-difluorophenyl)-5-fluoropy-
rimidin-2-yl]amino}benzyl)(methyl)oxido-$\lambda^6$-sulfa-
nylidene]cyanamide;

(rac)-N-{3-Bromo-5-[(S-methylsulfonimidoyl)methyl]
phenyl}-4-(2,4-difluorophenyl)-5-fluoropyrimidin-2-
amine;

(rac)-[(3-{[4-(2,4-Difluorophenyl)-5-fluoropyrimidin-2-
yl]amino}-5-methoxybenzyl)(methyl)oxido-$\lambda^6$-sulfa-
nylidene]cyanamide;

(rac)-4-(2,4-Difluorophenyl)-5-fluoro-N-{3-methoxy-5-
[(S-methylsulfonimidoyl)methyl]phenyl}pyrimidin-2-
amine;

(rac)-{[3-{[4-(2,4-Difluorophenyl)-5-fluoropyrimidin-2-
yl]amino}-5-(trifluoromethyl)benzyl](2-methoxy-
ethyl)oxido-$\lambda^6$-sulfanylidene}cyanamide;

1-{[3-{[4-(2,4-Difluorophenyl)-5-fluoropyrimidin-2-yl]
amino}-5-(trifluoromethyl)benzyl](methyl)oxido-$\lambda^6$-
sulfanylidene}urea; enantiomer 1;

1-{[3-{[4-(2,4-Difluorophenyl)-5-fluoropyrimidin-2-yl]
amino}-5-(trifluoromethyl)benzyl](methyl)oxido-$\lambda^6$-
sulfanylidene}urea; enantiomer 2;

(rac)-N-[3-{[S-(2-Aminoethyl)sulfonimidoyl]methyl}-5-
(trifluoromethyl)phenyl]-4-(2,4-difluorophenyl)-5-
fluoropyrimidin-2-amine trifluoroacetate;

N-[3-{[S-(2-Aminoethyl)sulfonimidoyl]methyl}-5-(trif-
luoromethyl)phenyl]-4-(2,4-difluorophenyl)-5-fluoro-
pyrimidin-2-amine; enantiomer 1;

N-[3-{[S-(2-Aminoethyl)sulfonimidoyl]methyl}-5-(trif-
luoromethyl)phenyl]-4-(2,4-difluorophenyl)-5-fluoro-
pyrimidin-2-amine; enantiomer 2;

(rac)-{[3-{[4-(2,4-Difluorophenyl)-5-fluoropyrimidin-2-
yl]amino}-5-(pentafluoro-$\lambda^6$-sulfanyl)benzyl](methyl)
oxido-$\lambda^6$-sulfanylidene}cyanamide;

{[3-{[4-(2,4-Difluorophenyl)-5-fluoropyrimidin-2-yl]
amino}-5-(pentafluoro-$\lambda^6$-sulfanyl)benzyl](methyl)
oxido-$\lambda^6$-sulfanylidene}cyanamide; enantiomer 1;

{[3-{[4-(2,4-Difluorophenyl)-5-fluoropyrimidin-2-yl]
amino}-5-(pentafluoro-$\lambda^6$-sulfanyl)benzyl](methyl)
oxido-$\lambda^6$-sulfanylidene}cyanamide; enantiomer 2;

4-(2,4-Difluorophenyl)-5-fluoro-N-{3-[(S-methylsulfon-
imidoyl)methyl]-5-(pentafluoro-$\lambda^6$-sulfanyl)
phenyl}pyrimidin-2-amine; enantiomer 1;

4-(2,4-Difluorophenyl)-5-fluoro-N-{3-[(S-methylsulfon-
imidoyl)methyl]-5-(pentafluoro-$\lambda^6$-sulfanyl)
phenyl}pyrimidin-2-amine; enantiomer 2;

1-{[3-{[4-(2,4-Difluorophenyl)-5-fluoropyrimidin-2-yl]
amino}-5-(pentafluoro-$\lambda^6$-sulfanyl)benzyl](methyl)
oxido-$\lambda^6$-sulfanylidene}urea; enantiomer 1;

1-{[3-{[4-(2,4-Difluorophenyl)-5-fluoropyrimidin-2-yl]
amino}-5-(pentafluoro-$\lambda^6$-sulfanyl)benzyl](methyl)
oxido-$\lambda^6$-sulfanylidene}urea; enantiomer 2;

[(3-{[4-(2,4-Difluorophenyl)-5-fluoro-pyrimidin-2-yl]
amino}-5-methylbenzyl)-(methyl)oxido-$\lambda^6$-sulfa-
nylidene]cyanamide; enantiomer 1;

[(3-{[4-(2,4-Difluorophenyl)-5-fluoro-pyrimidin-2-yl]
amino}-5-methylbenzyl)-(methyl)oxido-$\lambda^6$-sulfa-
nylidene]cyanamide; enantiomer 2;

4-(2,4-Difluorophenyl)-5-fluoro-N-{3-methyl-5-[(S-
methylsulfonimidoyl)methyl]-phenyl}pyrimidin-2-
amine; enantiomer 1;

4-(2,4-Difluorophenyl)-5-fluoro-N-{3-methyl-5-[(S-
methylsulfonimidoyl)methyl]-phenyl}pyrimidin-2-
amine; enantiomer 2;

[(3-Bromo-5-{[4-(2,4-difluorophenyl)-5-fluoropyrimi-
din-2-yl]amino}benzyl)(methyl)oxido-$\lambda^6$-sulfa-
nylidene]cyanamide; enantiomer 1;

[(3-Bromo-5-{[4-(2,4-difluorophenyl)-5-fluoropyrimi-
din-2-yl]amino}benzyl)(methyl)oxido-$\lambda^6$-sulfa-
nylidene]cyanamide; enantiomer 2;

N-{3-Bromo-5-[(S-methylsulfonimidoyl)methyl]phe-
nyl}-4-(2,4-difluorophenyl)-5-fluoropyrimidin-2-
amine; enantiomer 1;

N-{3-Bromo-5-[(S-methylsulfonimidoyl)methyl]phe-
nyl}-4-(2,4-difluorophenyl)-5-fluoropyrimidin-2-
amine; enantiomer 2, and the enantiomers, diastereomers, salts, solvates or salts
of solvates thereof.

9. A pharmaceutical combination comprising a compound according to claim 1 in combination with at least one or more further active ingredients.

10. A pharmaceutical composition comprising a compound according to claim 1 in combination with an inert, nontoxic, pharmaceutically suitable adjuvant.

11. A compound of general formula (15)

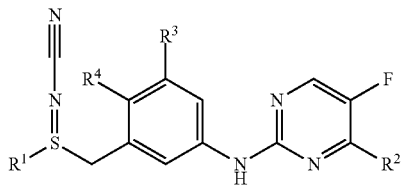

15 wherein $R^1$, $R^2$, $R^3$ and $R^4$ are as defined in claim 1,
or an enantiomer, diastereomer, salt, solvate or salt of a solvate thereof.

12. A method for the preparation of a compound according to claim 1, wherein
$R^5$ is a cyano group, comprising oxidizing a compound of formula (15)

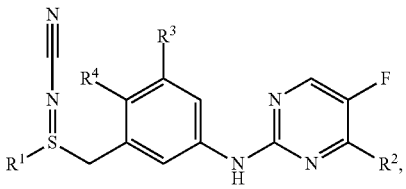

15 in which $R^1$, $R^2$, $R^3$ and $R^4$ are as defined in claim 1 using an alkali salt of permanganic acid in an aliphatic ketone of the formula $C_1$-$C_2$-alkyl-C(=O)—$C_1$-$C_2$-alkyl, to provide a compound according to claim 1 wherein $R^5$ is a cyano group, and optionally reacting the compound according to claim 1 with a solvent, base, or acid to provide a solvate, salt, or solvate of a salt thereof.

13. A method for the preparation of a compound of formula (15)

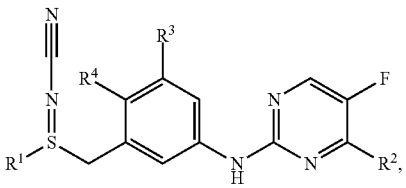

15 wherein $R^1$, $R^2$, $R^3$ and $R^4$ are as defined in claim 1, comprising reacting a compound of formula (14)

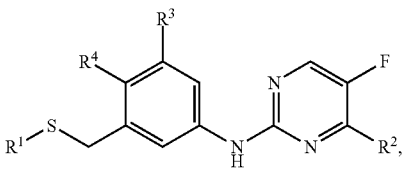

14 wherein $R^1$, $R^2$, $R^3$ and $R^4$ are as defined in claim 1 with
(a) cyanamide in the presence of iodobenzene diacetate in a halogenated aliphatic hydrocarbon as a solvent, or
(b) sodium hydrogencyanamide in the presence of 1,3-dibromo-5,5-dimethylhydantoin in an aliphatic alcohol of the formula $C_1$-$C_4$-alkyl-OH as a solvent, thus providing a compound of formula (15), and optionally reacting the compound of formula (15) with a solvent, base, or acid to provide a solvate, salt, or solvate of a salt thereof.

14. A method for the treatment of lung carcinoma, prostate carcinoma, cervical carcinoma, colorectal carcinoma, melanoma, ovarian carcinoma or leukemia, comprising administering to a patient in need thereof a therapeutically effective amount of a compound according to claim 1.

* * * * *